US006548290B1

(12) United States Patent
McGarry et al.

(10) Patent No.: US 6,548,290 B1
(45) Date of Patent: Apr. 15, 2003

(54) GEMININ GENE AND PROTEIN

(75) Inventors: Thomas J. McGarry, Newton, MA (US); Kristen Kroll, Brookline, MA (US); Marc W. Kirschner, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/096,724

(22) Filed: Jun. 11, 1998

Related U.S. Application Data

(60) Provisional application No. 60/085,371, filed on May 13, 1998.

(51) Int. Cl.[7] ............................................. C12N 15/00
(52) U.S. Cl. ................. 435/252.3; 435/325; 435/320.1; 536/23.2; 536/23.5
(58) Field of Search ............................ 536/23.1, 23.2, 536/23.5; 514/44; 435/320.1, 325, 252.3

(56) References Cited

U.S. PATENT DOCUMENTS

| | | | |
|---|---|---|---|
| 5,399,346 A | 3/1995 | Anderson et al. | ......... 424/93.21 |
| 5,643,873 A | 7/1997 | Barrett et al. | .................. 514/12 |
| 5,654,276 A | 8/1997 | Barrett et al. | .................. 514/13 |

OTHER PUBLICATIONS

Hillier et al, GenBank Accession No. AA447810 Jun. 4, 1997.*
Marra et al, Trends in Genetics, Jan. 1998, vol. 14, No. 1, pages unknown.*
Hudson GenBankâ Accession No. G24505 (1996) ENTREZ Release 24.0, Aug. 15, 1996).*
Hudson, GenBank Accession No. G24504 1996.*
Chitnis, et al., "Neural Induction and Neurogenesis in Amphibian Embryos," *Perspectives on Developmental Neurobiology,* 3(1): 3–15 (1995).
Nieuwkopp, et al., "The Further Development of the Cephalic Ganglia and Nerves." In *Normal Table of Xenopus Laevis* (*Daudin*), P.D. Nieuwkoop, et al., eds. ((Garland Publishing, Inc.) pp. 60–73 (1994).
McGarry, T.J., et al., "Geminin, an Inhibitor of DNA Replication, Is Degraded during Mitosis", *Cell,* 93:1043–1053 (1998).
Kroll, K.L., et al., "Geminin, a neuralizing molecule that demarcates the future neural plate at the onset of gastrulation", *Development,* 125:3247–3258 (1998).
Marushige, Y., et al., "Growth Inhibition of Synchronized Trigeminal Neurinoma Cells by Nerve Growth Factor", *Anticancer Research,* 14:153–156 (1994).
Glotzer, M., et al., "Cyclin is degraded by the ubiquitin pathway", *Nature,* 349:132–138 (1991).
Nucleotide Sequence Database *EMBL,* ID MM1165322, Accession number AA250610, Mar. 15, 1997.

Nucleotide Sequence Database *EMBL,* ID AA544218, Accession number AA44218, Aug. 12, 1997.
Nucleotide Sequence Database *EMBL,* ID HS1221842, Accession number AA393139, May 19, 1997.
Nucleotide Sequence Database *EMBL,* ID HS1247813, Accession number AA447810, Jun. 10, 1997.
Chong, J.P. et al., "Purification of an MCM–containing complex as a component of the DNA replication licensing system," *Nature 375:*418–421 (1995).
Harland, R.M., "Neural induction in Xenopus," in *Molecular and Cellular Approaches to Neural Development,* (eds., W.M. Cowan, T.M. Jessell and S.L. Zipursky), Oxford: Oxford University Press, pp. 1–25 (1997).
Hutchinson, C.J., "The use of cell free extracts of Xenopus eggs for studying DNA replication in vitro," In The cell cycle: a practical approach, P. Fantes and R. Brooks, eds. (Oxford: IRL Press), pp. 177–195 (1993).
Kay, B.K. and Peng, H.B., *Xenopus laevis:* Practical uses in cell and molecular biology, vol. 36, L. Wilson, ed. (San Diego, California: Academic Press) (1991).
Oschwald, R. et al. "Localization of a nervous system–specific class II beta–tubulin gene in *Xenopus laevis* embryos by whole–mount in situ hybridization," *Int J Dev Biol 35:*399–405 (1991).
Schmidt, J.E. et al. "Regulation of dorsal–ventral patterning: the ventralizing effects of the novel Xenopus homobox gene Vox" *Development 122:*1711–21 (1996).
Amon, A. et al., "Closing the cell cycle circle in yeast: G2 cyclin proteolysis initiated at mitosis persists until the activation of G1 cyclins in the next cell cycle," *Cell 77:*1037–1050 (1994).
Aristarkhov, A. et al., E2–C, a cyclin selective ubiquitin carrier protein required for the destruction of mitotic cyclins, Proceedings of the National Academy of Sciences (USA) 93:4294–4299 (1996).
Berger, B. et al., "Predicting coiled coils by use of pairwise residue correlations," Proceedings of the National Academy of Sciences (USA) 92:8259–8263 (1995).
Blow, J.J. and Laskey, R.A., "Initiation of DNA replication in nuclei and purified DNA by a cell–free extract of Xenopus eggs," *Cell 47:*577–587 (1986).

(List continued on next page.)

*Primary Examiner*—James Martinell
(74) *Attorney, Agent, or Firm*—Hamilton, Brook, Smith & Reynolds, P.C.

(57) ABSTRACT

The claimed invention pertains to a novel protein called Geminin which is able to inhibit DNA replication and/or induce neurogenesis. The claimed invention includes the amino acid sequence, the nucleic acid sequence, and various domains thereof. The invention further relates to methods for treating patients with a proliferative disease by administering an effective amount of the Geminin protein and/or nucleic acid. Similarly, the claimed inventions pertains to methods for treating various neurological disorders by administering neuronal cells which were differentiated by exposure to Geminin.

10 Claims, 30 Drawing Sheets

OTHER PUBLICATIONS

Blow, J.J. et al., "A role for the nuclear envelope in controlling DNA replication within the cell cycle," *Nature* 332:546–548 (1998).

Brandeis, M., and Hunt, T., "The Proteolysis of mitotic cyclins in mammalian cells persists from the end of mitosis until the onset of S phase," EMBO Journal 15 (1996).

Brown, K.D. et al., "Cyclin–like accumulation and loss of the putative kinetochore motor CENP–E results from coupling continuous synthesis with specific degradation at the end of mitosis," *The Journal of Cell Biology* 125:1303–1312 (1994).

Carpenter, P.B. et al., "Role for a Xenopus Orc2–related protein in controlling DNA replication," *Nature* 379:357–360 (1996).

Chitnis, A. et al., "Primary neurogenesis in Xenopus embryos regulated by a homolog of the Drosophila neurogenic gene Delta," *Nature* 375:761–766 (1995a).

Cohen–Fix, O. et al., "Anaphase initiation in *Saccharomyces cerevisiae* is controlled by the APC–dependent degradation of the anaphase inhibitor Pds 1 p.", *Genes and Development* 10:3081–3093 (1996).

Coleman, T.R. et al., "The Xenopus Cdc6 protein is essential for the initiation of a single round of DNA replication in cell–free extracts," *Cell* 87:53–63 (1996).

Dahmann, C. et al., "S–phase–promoting cyclin dependent kinases prevent re–replication by inhibiting the transition of replication origins to a pre–replicative state," *Current Biology* 5:1257–1269 (1995).

Ferreiro, B. et al., "XASH genes promote neurogenesis in Xenopus embryos," *Development* 120:3649–3655 (1994).

Funabiki, H. et al., "Cut2 proteolysis required for sister–chromatid separation in fission yeast," Nature 381:438–441 (1996).

Gallant, P. and Nigg, E.A., "Cyclin B2 undergoes cell cycle dependent nuclear translocation and, when expressed as a non–destructible mutant, causes mitotic arrest in HeLa cells," *The Journal of Cell Biology* 117:213–224 (1992).

Ghiara, J.B. et al., "A cyclin B homolog in *S. cerevesiae*: chronic activation of the cdc28 protein kinase prevents exit from mitosis," *Cell* 65:163–174 (1991).

Glotzer, M. et al. "Cyclin is degraded by the ubiquitin pathway," *Nature* 349:132–138 (1991).

Godsave, S.F. and Slack, J.M., "Clonal analysis of mesoderm induction in *Xenopus laevis,*" *Dev Biol.* 134:486–490 (1989).

Gomez–Skarmeta, J.L. et al. "Araucan and caupolican, two members of the novel iroquois complex, encode homeoproteins that control proneural and vein–forming genes," *Cell* 85:95–105 (1996).

Graham, C.F. and Morgan, R.W., "Changes in the cell cycle during amphibian development," *Developmental Biology* 14:439–460 (1996).

Grunz, H. and Tack, L., "Neural differentiation of *Xenopus laevis* Ectoderm takes place after disaggregation and delayed reaggreagation without inducer," *Cell Differ. Dev.* 28:211–217 (1989).

Gurdon, J.B., "The effects of ultraviolet irradiaiton of the uncleaved eggs of *Xenopus laevis,*" *Q.J. Microsc. Sci.* 101:299–312 (1960).

Handeli, S. and Weintraub, H., "The ts41 mutation in Chinese hamster cell leads to successive rounds of S phase in the absence of intervening G2, M, and G1," *Cell* 71:599–611 (1992).

Hansen, C.S. et al. "Direct neural induction and selective inhibition of mesoderm and epidermis inducers by Xnr3," *Development* 124:483–492 (1997).

Harland, R. and Gerhart J., "Formation and function of Spemann's organizer," *Annual Review of Cell and Developmental Biology* 13:611–667 (1997).

Harland, R.M., "In situ hybridization: an improved whole––mount method for Xenopus embryos," *Methods Cell Biol.* 36:685–695 (1991).

Mechali, M et al., "DNA synthesis in a cell–free system from Xenopus eggs: Priming and Elongation on Single Stranded DNA in vitro," *Cell* 30:93–101 (1982).

Heichman, K.A. and Roberts, J.M., "Rules to replicate by," *Cell* 79:557–562 (1994).

Hemmati–Brivanlou, A. and Thomsen, G.H., "Ventral mesodermal patterning in Xenopus embryos: expression patterns and activities of BMP–2 and BMP–4," *Developmental Genetics* 17:78–89 (1995).

Hershko, A. et al. "Methylated ubiquitin inhibits cyclin degradation in clam embryo extracts," *Journal of Biological Chemistry* 266:16376–16379 (1991).

Hirano, T. and Mitchison, T., "Topoisomerase II does not play a scaffolding role in the organization of mitotic chromosomes assembled in Xenopus egg extract," *Journal of Cell Biology* 120:601–612 (1993).

Hirsch, N. and Harris, W.A.,. "Xenopus Pax–6 and retinal development," *Journal of Neurobiology* 3:45–61 (1997).

Hochstrasser, M., "Ubiquitin dependent protein degradation," *Annual Review of Genetics* 30:405–439 (1996).

Holloway, S.L. et al. "Anaphase is initiated by proteolysis rather than by the inactivation of maturation–promoting factor," *Cell* 73:1393–1402 (1993).

Hopwood, N.D. et al. "A Xenopus mRNA related to Drosophila twist is expressed in response to induction in the mesoderm and the neural crest," *Cell* 59:893–903 (1989).

Irniger, S. et al. "Genes involved in sister chromatid separation are needed for B–type cyclin proteolysis in budding yeast," *Cell* 81:269–277 (1995).

Jackson, P.K. et al. "Early events in DNA replication require cyclin E and are blocked by p21cip1," *Journal of Cell Biology* 130:755–769 (1995).

Jonas, E. et al. "Epidermal keratin gene expressed in embryos of *Xenopus laevis,*" *Proc. Natl. Acad. Sci. U.S.A.* 82:5413–5417 (1985).

Jones, C.M. et al. "DVR–4 (bone morphogenetic protein–4) as a posterior–ventralizing factor in Xenopus mesoderm induction," *Development* 115:639–647 (1992).

Juang, Y.–L. et al. "APC–mediated proteolysis of Ase I and the regulation of the mitotic spindle," *Science* 275:1311–1314 (1997).

Kengaku, M. and Okamoto, H., "bFGF as a possible morphogen for the anteroposterior axis of the central nervous system in Xenopus," *Development* 121:3121–3130 (1995).

Kim, P. et al. "XATH–1, a vertebrate homolog of Drosophila atonal, induces a neuronal differentiation within ectodermal progenitors," *Developmental Biology* 187:1–12 (1997).

King, R.W. et al. "How proteolysis drives the cell cycle," *Science* 274:1652–1659 (1996).

King, R.W. et al. "Mutagenic analysis of the destruction signal of mitotic cyclins and structural characterization of ubiquitinated intermediates," *Molecular Biology of Cell* 7:1343–1357 (1996).

King, R.W. et al. "A 20S Complex containing CDC27 and CDC16 catalyzes the mitosis–specific conjugation of ubiquitin to cyclin B," *Cell 81:*279–288 (1994).

Knecht, A.K. et al. "Dorsal–ventral patterning and differentiation of noggin–induced neural tissue in the absence of mesoderm," *Development 121:*1927–1935 (1995).

Krieg, P.A. and Melton, D.A., "In vitro RNA synthesis with SP6 RNA polymerase," *Methods Enzymol 155:*397–415 (1987).

Kroll, K.L. and Amaya, E., "Transgenic Xenopus embryos from sperm nuclear transplantations reveal FGF signaling requirements during gastrulation," *Development 122:*3173–3183 (1996).

Kubota, Y. et al. "Identification of the yeast MCM3–related protein as a component of Xenopus DNA replication licensing factor," *Cell 81:*601–609 (1995).

Ladher, R. et al. "Xom: a Xenopus homeobox gene that mediates the early effects of BMP–4," *Development 122:*2385–2394 (1995).

Lamb, T.M. et al. "Naural induction by the secreted polypeptide noggin," *Science 262:*713–718 (1993).

Lee, J.E., "Basic helix–loop–helix genes in neural development," *Current Opinion in Neurobiology 7:*13–20 (1997).

Lee, J.E. et al. "Conversion of Xenopus ectoderm into neurons by NeuroD, a basic helix–loop–helix protein," *Science 268:*836–844 (1995).

Lemaire, P. et al. "Expression cloning of Siamois, a Xenopus homeobox gene expressed in dorsal–vegetal cells of blastulae and able to induce a complete secondary axis," *Cell 81:*85–94 (1995).

Leno, G.H. et al. "The nuclear membrane prevents replication of human G2 nuclei but not G1 nuclei in Xenopus egg extract," *Cell 69:*151–158 (1992).

Luca, F.C. et al. "Both cyclin AΔ60 and cyclin BΔ97 are stable and arrest cells in M–phase, but only BΔ97 turns on cyclin destruction," *The EMBO Journal 10:*4311–4320 (1991).

Lupas, A. et al. "Predicting Coiled Coils from Protein Sequences," *Science 252:*1162–1164 (1991).

Lusting, K.D. et al. "A Xenopus nodal–related gene that acts in synergy with noggin to induce complete secondary axis and notochord formation," *Development 122:*3275–3282 (1996a).

Lustig, K.D. et al. "Expression cloning of a Xenopus T–related gene (Xombi) involved in mesodermal patterning and blastopore lip formation," *Development 122:*4001–4102 (1996b).

Lustig, K.D. et al. "Small pool expression screening: identification of genes involved in cell cycle control, apoptosis, and early development," *Methods in Enzymology 283,* In the press (1997).

Ma, Q. et al. "Identification of neurogenin, a vertebrate neuronal determination gene," *Cell 87:*43–52 (1996).

Mahbubani, H.M. et al. "Cell cycle regulation of the replication licensing system: involvement of a cdk–dependent inhibitor," *Journal of Cell Biology 136:*125–135 (1997).

Morgan, R. and Sargent, M.G., "The role in neural patterning of translation initiation factor eIF4AII; induction of neural fold genes," *Development 124:*2751–2760 (1997).

Moury, J.D. and Jacobson, A.G., "The origins of neural crest cells in the axolotl," *Developmental Biology 141:*243–253 (1990).

Murray, A., "Cell cycle extracts," *Methods in Cell Biology 36:*581–605 (1991).

Nishimatsu, S. et al. "Genes for bone morphogenetic proteins are differentially transcribed in early amphibian embryos," *Biochem Biophys Res Com 186:*1487–1495 (1992).

Nurse, P., "Iniversal control mechanism regulating the onset of M–phase," *Nature 344:*503–508 (1990).

Pellman, D. et al. "Two microtubule–associated proteins required for anaphase spindle movement in *Saccharomyces cerevesiae,*" *Journal of Cell Biology 130:*1373–1385 (1995).

Piatti, S. et al. "Activation of S–phase–promoting CDKs in late G1 defines a "point of no return" after which Cdc6 synthesis cannot promote DNA replication in yeast," *Genes and Development 10:*1515–1531 (1996).

Piccolo, S. et al. "Dorsoventral patterning in Xenopus: inhibition of ventral signals by direct binding of chordin to BMP–4," *Cell 86:*589–598 (1996).

Rao, P.N. and Johnson, R.T., "Mammalian cell fusion: studies on the regulation of DNA synthesis and mitosis," *Nature 255:*159–164 (1970).

Rao Y., "Conversion of a mesodermalizing molecule, the Xenopus Brachyury gene, into a neuralizing factor," *Genes & Development 8:*939–947 (1994).

Richter, K. et al. "Gene expression in the embryonic nervous system of *Xenopus laevis,*" Proc. Natl. Acad. Sci. U.S.A. 85:8086–8090 (1998).

Rowles, A. and Blow, J.J., "Chromatic proteins involved in the initiation of DNA replication," *Current Opinion in Genetics and Development 7:*152–157 (1997).

Rowles, A. et al. "Interaction between the origin recognition complex and the replication licensing system in Xenopus," *Cell 87:*287–296 (1996).

Sasai, Y. and DeRobertis, E.M., "Ectodermal patterning in vertebrate embryos," *Developmental Biology 182:*5–20 (1997).

Sasai, Y. et al. "Xenopus chordin: a novel dorsalizing factor activated by organizer–specific homeobox genes," *Cell 79:*779–790 (1994).

Selleck, M.A. and Bronner, F.M., "Origins of the avian neural crest: the role of neural plate–epidermal interactions," *Development 121:*525–538 (1995).

Smith, W.C. and Harland, R.M., "injected Xwnt–8 RNA acts early in Xenopus embryos to promote formation of a vegetal dorsalizing center," *Cell 67:*753–765 (1991).

Smith, W.C. and Harland, R.M., "Expression cloning of noggin, a new dorsalizing factor localized to the Spemann organizer in Xenopus embryos," *Cell 70:*829–840 (1992).

Stern, B. and Nurse, P., "A quantitative model for the cdc2 control of S phase and mitosis in fission yeast," *Trends in Genetics 12:*345–350 (1996).

Stillman, B., "Cell cycle control of DNA replication," *Science 274:*1659–1664 (1996).

Sudakin, V. et al. "The cyclosome, a large complex containing cyclin–selective ubiquitin ligase activity, targets cyclins for destruction at the end of mitosis," *Molecular Biology of the Cell 6:*185–198 (1995).

Suzuki, A. et al. "Xenopus msxl mediates epidermal induction and neural inhibition by BMP4," *Development* 124:3037–3044 (1997).

Takebayashi, K. et al. "Conversion of ectoderm into a neural fate by ATH–3, a vertebrate basic helix–loop–helix gene homologous to Drosophila proneural gene atonal," *Embo Journal 16:*384–395 (1997).

Turner, D.L. and Weintraub, H., "Expression of achaete-scute homolog 3 in Xenopus embryos converts ectodermal cells to a neural fate," *Genes & Development* 8:1434–1447 (1994).

Weinsten, D.C. and Hemmati, B.A., "Neural induction in *Xenopus laevis:* evidence for the default model," *Current Opinion in Neurobiology* 7:7–12 (1997).

Wilkinson, D.G., "Whole mount in situ hybridization of vertebrate embryos," In *In situ hybridization: A practical approach,* (D.G. Wilkinson, ed.), Oxford: IRL Press.

Wilson, P.A. and Hemmati, B.A., "Induction of epidermis and inhbition of neural fate by BMP–4," *Nature* 376:331–333 (1995).

Wilson, P.A. and Melton, D.A., "Mesodermal patterning by an inducer gradient depends on secondary cell–cell communication," *Current Biology* 4:676–686 (1994).

Witta, S.E. et al. "XIPOU 2, a noggin–inducible gene, has direct neuralizing activity," *Development* 121:721–730 (1995).

Yamamoto, A. et al. "Pds1p is required for faithful execution of anaphase in the yeast, *Saccharomyces cerevisiae,*" *Journal of Cell Biology* 113:85–97 (1996).

Yamashita, H. et al. "Osteogenic protein–1 binds to activin type II receptors and induces certain activin–like effects," *J. Cell Biol.* 130:217–226 (1995).

Yu, H. et al. "Identification of a novel ubiquitin–conjugating enzyme involved in mitotic cyclin degradation," *Current Biology* 6:455–466 (1996).

Yu, K. et al. "The Drosophila decapentaplegic and short gastrulation genes function antagonistically during adult wing vein development," *Development* 122:4033–4044 (1996).

Zimmerman, K. et al. "XASH–3, a novel Xenopus achaete–scute homolog, provides an early marker of planar neural induction and position along the mediolateral axis of the neural plate," *Development* 119:221–232 (1993).

Zimmerman, L.B. et al. "The Spemann organizer signal noggin binds and inactivates bones morphogenetic protein–4," *Cell* 86:599–606 (1996).

Williams, et al. *Nature* 31:476 (1984).

Dick, et al. *Cell* 42:71 (1985).

Keller, et al. *Nature* 318:149 (1985).

Rueckert, Picornaviridae: The viruses and their replication, *In Fundamental Virology,* Third Edition, B.N. Fields, et al., Eds., Lippincott–Raven Publishers, Philadelphia (1996). pp. 477–522.

Krisky, D.M. et al. *Gene Therapy* 4(*10*):1120–1125 (1997).

Amalfitano, A. et al. *Journal of Virology* 72(*2*):926–933 (1998).

Zufferey, R. et al. *Nature Biotechnology* 15(*9*):871–875 (1997).

Feng, M. et al. *Nature Biotechnology* 15(*9*):866–870 (1997).

Harris W. A. and Hartenstein, V., "Neuronal determination without cell division in Xenopus embryos", *Neuron* 6:499–515 (1991).

Murray, A. et al. "The role of cyclin symthesis and degradation in the control of maturation promoting factor activity", *Nature* 339:280–289 (1989).

Kasid, et al. *Proc. Natl. Acad. Sci. USA* 87:473 (1990).

Rosenberg, et al. *New Engl J. Med* 323:570 (1990).

Lamb, T.M. et al. "Fibroblast growth factor is a direct neural inducer, which combined with noggin generates anterior––posterior neural pattern", *Development* 121:3627–3636.

* cited by examiner

FIG. 1

| | MUTATION | HALF LIFE | % REPLICATION |
|---|---|---|---|
| RRTLKVIQP | WT | 15min | 6 |
| | N30 | 15 | 8 |
| | N45 | >120 | 2 |
| | N60 | ND | 4 |
| | N80 | >120 | 5 |
| | N100 | ND | 119 |
| | N120 | ND | 113 |
| | C200 | 20 | 8 |
| | C180 | 10 | 12 |
| | C160 | ND | 18 |
| | C140 | ND | 93 |
| | C120 | 15 | 89 |
| | DEL | >120 | 5 |
| RRTAKVIQP | L36A | >120 | ND |

```
MNSNMKQRSDVENPSMSIKNYIVDKTNEALAPRRTLKVIQQSASGCLVGR  Xenopus L
MNTNKKQRLDMEKPTMSIKNYFVDKTNESLAPRRTLKVIQPSASGCLVGR  Xenopus H
MNLSMKQKQEGAQ------ENVKNSPVPRRTLKMIQPSADGSLVGR      mouse
MNPSMKQKQEEIK------ENIKNSSVPRRTLKMIQPSASGSLVGR      human TKEPAKNSTKRKLWNDQLTSKKKAKVEVAVDPEHQENKDCPS---EAYDLM  Xenopus L
TKEPVKNSTKRKLWNDQLTSKKKAKVEVAVDPEHRENKDCSS---EAYDLM  Xenopus H
ENELPKGLFKRKLWDDQLASQTSSCG---PEANENKDVGDLTQEAFDLI    mouse
ENELSAGLSKRKHRNDHLTSTTSSPGVIV-PESSENKNLGGVTQESFDLM   human VKETPTCLYWKDVAEERRKALYEALQENEKLHQEIELKDEEIARLKQEND  Xenopus L
VKETPTCLYWKEVAEERRKALYEALQENEKLHKEIELKDEEIARLKQEND  Xenopus H
SKENPSSQYWKEVAEQRRKALYEALKENEKLHKEIEQKDSEIARLRKENK  mouse
IKENPSSQYWKEVAEKRRKALYEALKENEKLHKEIEQKDNEIARLKKENK  human ELMELAGHVQYMANMIERLTGNAPQSLEDLKNLDLEEARFEDEA---ESR  Xenopus L
ELMELAGHVQYMANMIERLTGNAPRSLEDLKDLDLEEARFEDEADMAEAR  Xenopus H
DLAEVAEHVQYMAEVIERLSN-----EPLDNFESPDSQE---FDSEEEAVEYS  mouse
ELAEVAEHVQYMAELIERLNG-----EPLDNFESLDNQE---FDSEEETVEDS  human IEDETDMTQPSSSDQNMDKQT---V.    Xenopus L   (SEQ ID NO: 5)
IEDETDMARPSNSDQNMDAHT---V.    Xenopus H   (SEQ ID NO: 6)
ELEDSGAGTCAEETVSSSTDARPCT.    mouse        (SEQ ID NO: 7)
LVEDSEIGTCAEGTVSSSTDAKPCI.    human        (SEQ ID NO: 8)
```

FIG. 10A

Xenopus Geminin L

```
1/1                                           31/11
ATG AAT AGC AAC ATG AAG CAG AGA TCT GAT GTA GAG AAC CCT TCC ATG TCA ATT AAG AAC
 M   N   S   N   M   K   Q   R   S   D   V   E   N   P   S   M   S   I   K   N

61/21                                         91/31
TAC ATT GTA GAT AAA ACA AAT GAG GCA CTT GCA CCA AGA AGA ACA CTT AAA GTA ATC CAG
 Y   I   V   D   K   T   N   E   A   L   A   P   R   R   T   L   K   V   I   Q

121/41                                        151/51
CAA TCT GCA TCT GGG TGC CTT GTT GGA AGG ACC AAA GAG CCT GCT AAA AAT TCT ACA AAA
 Q   S   A   S   G   C   L   V   G   R   T   K   E   P   A   K   N   S   T   K

181/61                                        211/71
AGA AAA CTA TGG AAT GAT CAA CTG ACT TCA AAA AAG GCT AAA GTT GAA GTG GCT GTT GAT
 R   K   L   W   N   D   Q   L   T   S   K   K   A   K   V   E   V   A   V   D

241/81                                        271/91
CCA GAA CAC CAG GAA AAC AAG GAT TGC CCA TCT GAA GCA TAT GAC CTC ATG GTG AAA GAA
 P   E   H   Q   E   N   K   D   C   P   S   E   A   Y   D   L   M   V   K   E

301/101                                       331/111
ACC CCA ACT TGT CTG TAC TGG AAG GAT GTT GCA GAG GAA AGA AGA AAG GCC CTC TAT GAA
 T   P   T   C   L   Y   W   K   D   V   A   E   E   R   R   K   A   L   Y   E

361/121                                       391/131
GCA TTA CAA GAA AAT GAG AAG CTG CAT CAA GAA ATA GAA CTC AAA GAT GAA GAA ATT GCA
 A   L   Q   E   N   E   K   L   H   Q   E   I   E   L   K   D   E   E   I   A

421/141                                       451/151
CGC TTG AAA CAA GAA AAT GAT GAA TTA ATG GAA CTT GCT GGA CAT GTA CAG TAC ATG GCG
 R   L   K   Q   E   N   D   E   L   M   E   L   A   G   H   V   Q   Y   M   A

481/161                                       511/171
AAT ATG ATT GAA AGG CTC ACT GGA AAT GCA CCA CAA AGT CTT GAA GAT TTA AAG AAT TTG
 N   M   I   E   R   L   T   G   N   A   P   Q   S   L   E   D   L   K   N   L

541/181                                       571/191
GAT TTA GAA GAA GCA AGG TTT GAA GAT GAA GCA GAA TCA AGG ATT GAA GAT GAA ACT GAT
 D   L   E   E   A   R   F   E   D   E   A   E   S   R   I   E   D   E   T   D

601/201                                       631/211
ATG ACT CAG CCC TCA AGT TCA GAT CAG AAC ATG GAT AAA CAA ACT GTC TAG (SEQ ID NO: 1)
 M   T   Q   P   S   S   S   D   Q   N   M   D   K   Q   T   V   *  (SEQ ID NO: 5)
```

FIG. 16

Xenopus Geminin H

```
1/1                                           31/11
ATG AAT ACC AAC AAG AAG CAG AGA TTG GAT ATG GAG AAG CCT ACC ATG TCT ATT AAG AAC
 M   N   T   N   K   K   Q   R   L   D   M   E   K   P   T   M   S   I   K   N

61/21                                         91/31
TAC TTT GTG GAT AAA ACA AAC GAG TCC CTT GCA CCC AGA AGA ACA CTT AAA GTA ATC CAG
 Y   F   V   D   K   T   N   E   S   L   A   P   R   R   T   L   K   V   I   Q

121/41                                        151/51
CCA TCT GCA TCT GGA TGC CTT GTT GGA AGG ACC AAA GAG CCT GTT AAA AAT TCT ACA AAA
 P   S   A   S   G   C   L   V   G   R   T   K   E   P   V   K   N   S   T   K

181/61                                        211/71
AGA AAG CTG TGG AAT GAT CAG CTG ACT TCA AAA AAG GCT AAA GTT GAA GTG GCT GTT GAT
 R   K   L   W   N   D   Q   L   T   S   K   K   A   K   V   E   V   A   V   D

241/81                                        271/91
CCA GAA CAC AGG GAA AAC AAA GAT TGC TCA TCT GAA GCT TAT GAC CTT ATG GTG AAA GAA
 P   E   H   R   E   N   K   D   C   S   S   E   A   Y   D   L   M   V   K   E

301/101                                       331/111
ACA CCA ACT TGC CTT TAC TGG AAG GAG GTT GCA GAG GAA CGA AGA AAG GCC CTC TAT GAA
 T   P   T   C   L   Y   W   K   E   V   A   E   E   R   R   K   A   L   Y   E

361/121                                       391/131
GCA TTA CAG GAA AAT GAG AAG CTG CAT AAA GAA ATA GAA CTC AAA GAT GAA GAA ATT GCA
 A   L   Q   E   N   E   K   L   H   K   E   I   E   L   K   D   E   E   I   A

421/141                                       451/151
CGT TTG AAA CAA GAA AAT GAC GAA TTA ATG GAA CTT GCT GGG CAT GTA CAA TAC ATG GCT
 R   L   K   Q   E   N   D   E   L   M   E   L   A   G   H   V   Q   Y   M   A

481/161                                       511/171
AAT ATG ATT GAA AGG CTC ACT GGA AAT GCT CCA CGA AGT CTT GAA GAC TTA AAG GAT TTG
 N   M   I   E   R   L   T   G   N   A   P   R   S   L   E   D   L   K   D   L

541/181                                       571/191
GAT TTG GAA GAA GCA AGA TTT GAA GAT GAA GCA GAC ATG GCA GAA GCA AGG ATT GAA GAT
 D   L   E   E   A   R   F   E   D   E   A   D   M   A   E   A   R   I   E   D

601/201                                       631/211
GAA ACT GAC ATG GCT CGG CCC TCT AAT TCA GAT CAG AAT ATG GAT GCA CAT ACT GTC TAG  (SEQ ID NO:2)
 E   T   D   M   A   R   P   S   N   S   D   Q   N   M   D   A   H   T   V   *  (SEQ ID NO: 6)
```

FIG. 17

Mouse Geminin

```
1/1                                     31/11
ATG AAT CTC AGT ATG AAG CAG AAG CAG GAG GGA GCC CAA GAG AAT GTG AAG AAT AGT CCT
 M   N   L   S   M   K   Q   K   Q   E   G   A   Q   E   N   V   K   N   S   P

61/21                                   91/31
GTC CCA AGG AGA ACG CTG AAG ATG ATC CAG CCT TCT GCA GAT GGA TCT CTT GTT GGC AGA
 V   P   R   R   T   L   K   M   I   Q   P   S   A   D   G   S   L   V   G   R

121/41                                  151/51
GAA AAT GAG TTG CCA AAA GGC TTG TTC AAA AGG AAG CTT TGG GAT GAC CAG CTA GCA TCT
 E   N   E   L   P   K   G   L   F   K   R   K   L   W   D   D   Q   L   A   S

181/61                                  211/71
CAG ACT TCA AGC TGT GGT CCA GAA GCT AAT GAA AAT AAG GAT GTT GGA GAC CTC ACC CAG
 Q   T   S   S   C   G   P   E   A   N   E   N   K   D   V   G   D   L   T   Q

241/81                                  271/91
GAA GCC TTT GAT CTT ATA AGT AAA GAG AAC CCA TCT TCT CAG TAT TGG AAA GAA GTG GCA
 E   A   F   D   L   I   S   K   E   N   P   S   S   Q   Y   W   K   E   V   A

301/101                                 331/111
GAG CAG CGG AGG AAA GCT CTC TAC GAA GCG CTG AAA GAG AAT GAG AAA CTT CAT AAA GAA
 E   Q   R   R   K   A   L   Y   E   A   L   K   E   N   E   K   L   H   K   E

361/121                                 391/131
ATT GAA CAA AAG GAC AGT GAG ATT GCC CGC CTG AGA AAG GAG AAT AAA GAC TTG GCA GAA
 I   E   Q   K   D   S   E   I   A   R   L   R   K   E   N   K   D   L   A   E

421/141                                 451/151
GTA GCT GAG CAC GTG CAG TAC ATG GCG GAG GTA ATC GAG AGG CTG AGT AAT GAA CCT CTG
 V   A   E   H   V   Q   Y   M   A   E   V   I   E   R   L   S   N   E   P   L

481/161                                 511/171
GAT AAC TTT GAA TCA CCG GAT AGT CAG GAA TTT GAT TCT GAA GAA GAA GCT GTT GAG TAT
 D   N   F   E   S   P   D   S   Q   E   F   D   S   E   E   E   A   V   E   Y

541/181                                 571/191
TCA GAA CTG GAA GAC TCA GGA GCT GGG ACG TGT GCT GAA GAG ACT GTG TCT TCC TCC ACG
 S   E   L   E   D   S   G   A   G   T   C   A   E   E   T   V   S   S   S   T

601/201
GAT GCT AGG CCG TGT ACA TGA (SEQ ID NO: 3)
 D   A   R   P   C   T   *  (SEQ ID NO: 7)
```

FIG. 18

Human Geminin

```
1/1                                            31/11
ATG AAT CCC AGT ATG AAG CAG AAA CAA GAA GAA ATC AAA GAG AAT ATA AAG AAT AGT TCT
 M   N   P   S   M   K   Q   K   Q   E   E   I   K   E   N   I   K   N   S   S

61/21                                          91/31
GTC CCA AGA AGA ACT CTG AAG ATG ATT CAG CCT TCT GCA TCT GGA TCT CTT GTT GGA AGA
 V   P   R   R   T   L   K   M   I   Q   P   S   A   S   G   S   L   V   G   R

121/41                                         151/51
GAA AAT GAG CTG TCC GCA GGC TTG TCC AAA AGG AAA CAT CGG AAT GAC CAC TTA ACA TCT
 E   N   E   L   S   A   G   L   S   K   R   K   H   R   N   D   H   L   T   S

181/61                                         211/71
ACA ACT TCC AGC CCT GGG GTT ATT GTC CCA GAA TCT AGT GAA AAT AAA AAT CTT GGA GGA
 T   T   S   S   P   G   V   I   V   P   E   S   S   E   N   K   N   L   G   G

241/81                                         271/91
GTC ACC CAG GAG TCA TTT GAT CTT ATG ATT AAA GAA AAT CCA TCC TCT CAG TAT TGG AAG
 V   T   Q   E   S   F   D   L   M   I   K   E   N   P   S   S   Q   Y   W   K

301/101                                        331/111
GAA GTG GCA GAA AAA CGG AGA AAG GCG CTG TAT GAA GCA CTT AAG GAA AAT GAG AAA CTT
 E   V   A   E   K   R   R   K   A   L   Y   E   A   L   K   E   N   E   K   L

361/121                                        391/131
CAT AAA GAA ATT GAA CAA AAG GAC AAT GAA ATT GCC CGC CTG AAA AAG GAG AAT AAA GAA
 H   K   E   I   E   Q   K   D   N   E   I   A   R   L   K   K   E   N   K   E

421/141                                        451/151
CTG GCA GAA GTA GCA GAA CAT GTA CAG TAT ATG GCA GAg CTA ATA GAG AGA CTG AAT GGT
 L   A   E   V   A   E   H   V   Q   Y   M   A   E   L   I   E   R   L   N   G

481/161                                        511/171
GAA CCT CTG GAT AAT TTT GAA TCA CTG GAT AAT CAG GAA TTT GAT TCT GAA GAA GAA ACT
 E   P   L   D   N   F   E   S   L   D   N   Q   E   F   D   S   E   E   E   T

541/181                                        571/191
GTT GAG GAT TCT CTA GTG GAA GAC TCA GAA ATT GGC ACG TGT gCT GAA GGA ACT GTA TCT
 V   E   D   S   L   V   E   D   S   E   I   G   T   C   A   E   G   T   V   S

601/201
TCC TCT ACG GAT GCA AAG CCA TGT ATA TGA (SEQ ID NO: 4)
 S   S   T   D   A   K   P   C   I   *   (SEQ ID NO: 8)
```

FIG. 19

Xenopus Geminin L

GGCACGAGCCTGCAGTGGTCTTGTGCGTGAAAAGAGCAGAGGCTTAAG

```
1/1                                             31/11
ATG AAT AGC AAC ATG AAG CAG AGA TCT GAT GTA GAG AAC CCT TCC ATG TCA ATT AAG AAC
 M   N   S   N   M   K   Q   R   S   D   V   E   N   P   S   M   S   I   K   N

61/21                                           91/31
TAC ATT GTA GAT AAA ACA AAT GAG GCA CTT GCA CCA AGA AGA ACA CTT AAA GTA ATC CAG
 Y   I   V   D   K   T   N   E   A   L   A   P   R   R   T   L   K   V   I   Q

121/41                                          151/51
CAA TCT GCA TCT GGG TGC CTT GTT GGA AGG ACC AAA GAG CCT GCT AAA AAT TCT ACA AAA
 Q   S   A   S   G   C   L   V   G   R   T   K   E   P   A   K   N   S   T   K

181/61                                          211/71
AGA AAA CTA TGG AAT GAT CAA CTG ACT TCA AAA AAG GCT AAA GTT GAA GTG GCT GTT GAT
 R   K   L   W   N   D   Q   L   T   S   K   K   A   K   V   E   V   A   V   D

241/81                                          271/91
CCA GAA CAC CAG GAA AAC AAG GAT TGC CCA TCT GAA GCA TAT GAC CTC ATG GTG AAA GAA
 P   E   H   Q   E   N   K   D   C   P   S   E   A   Y   D   L   M   V   K   E

301/101                                         331/111
ACC CCA ACT TGT CTG TAC TGG AAG GAT GTT GCA GAG GAA AGA AGA AAG GCC CTC TAT GAA
 T   P   T   C   L   Y   W   K   D   V   A   E   E   R   R   K   A   L   Y   E

361/121                                         391/131
GCA TTA CAA GAA AAT GAG AAG CTG CAT CAA GAA ATA GAA CTC AAA GAT GAA GAA ATT GCA
 A   L   Q   E   N   E   K   L   H   Q   E   I   E   L   K   D   E   E   I   A

421/141                                         451/151
CGC TTG AAA CAA GAA AAT GAT GAA TTA ATG GAA CTT GCT GGA CAT GTA CAG TAC ATG GCG
 R   L   K   Q   E   N   D   E   L   M   E   L   A   G   H   V   Q   Y   M   A

481/161                                         511/171
AAT ATG ATT GAA AGG CTC ACT GGA AAT GCA CCA CAA AGT CTT GAA GAT TTA AAG AAT TTG
 N   M   I   E   R   L   T   G   N   A   P   Q   S   L   E   D   L   K   N   L

541/181                                         571/191
GAT TTA GAA GAA GCA AGG TTT GAA GAT GAA GCA GAA TCA AGG ATT GAA GAT GAA ACT GAT
 D   L   E   E   A   R   F   E   D   E   A   E   S   R   I   E   D   E   T   D

601/201                                         631/211
ATG ACT CAG CCC TCA AGT TCA GAT CAG AAC ATG GAT AAA CAA ACT GTC TAG
 M   T   Q   P   S   S   S   D   Q   N   M   D   K   Q   T   V   *   (SEQ ID NO: 5)
```

CCTGTGAACTACTGACTTTTTTAAAAAAAAATTTTTTAAAGTGGCCGGTAACATTTCGAAAGATCTTCTGCTCAATGGAAGCTGAA
AAAGTAACATTTTATTAGTCCGTAATGTTGAAGGGTTTAAGTTCAGTAAGACCTTTAACTGCGAAGCTTGACATCTGATTAAGGAA
GTTTTAGAATTTGCTAACTCAATATTTTAAGTTGGGTCACTTGTCTAACAAATACTATGTATTTATTGTAAATGGGGTTCTTTTTT
TAATTTCCAGCCTTTATGTGAGGTGATTGTACATACTTGAATAAACTTCAGTTTTAAGTATTAAAAAAAACAAAAAAAAAAAAAAAA
AAAA (SEQ ID NO: 17)

FIG. 20

Xenopus Geminin H

GGCTCGAGGGAAGGTTTTGTGTTTGAGAGGAGCGGCAGGCACCAGGTTTAAT

```
1/1                                      31/11
ATG AAT ACC AAC AAG AAG CAG AGA TTG GAT  ATG GAG AAG CCT ACC ATG TCT ATT AAG AAC
 M   N   T   N   K   K   Q   R   L   D    M   E   K   P   T   M   S   I   K   N

61/21                                    91/31
TAC TTT GTG GAT AAA ACA AAC GAG TCC CTT  GCA CCC AGA AGA ACA CTT AAA GTA ATC CAG
 Y   F   V   D   K   T   N   E   S   L    A   P   R   R   T   L   K   V   I   Q

121/41                                   151/51
CCA TCT GCA TCT GGA TGC CTT GTT GGA AGG  ACC AAA GAG CCT GTT AAA AAT TCT ACA AAA
 P   S   A   S   G   C   L   V   G   R    T   K   E   P   V   K   N   S   T   K

181/61                                   211/71
AGA AAG CTG TGG AAT GAT CAG CTG ACT TCA  AAA AAG GCT AAA GTT GAA GTG GCT GTT GAT
 R   K   L   W   N   D   Q   L   T   S    K   K   A   K   V   E   V   A   V   D

241/81                                   271/91
CCA GAA CAC AGG GAA AAC AAA GAT TGC TCA  TCT GAA GCT TAT GAC CTT ATG GTG AAA GAA
 P   E   H   R   E   N   K   D   C   S    S   E   A   Y   D   L   M   V   K   E

301/101                                  331/111
ACA CCA ACT TGC CTT TAC TGG AAG GAG GTT  GCA GAG GAA CGA AGA AAG GCC CTC TAT GAA
 T   P   T   C   L   Y   W   K   E   V    A   E   E   R   R   K   A   L   Y   E

361/121                                  391/131
GCA TTA CAG GAA AAT GAG AAG CTG CAT AAA  GAA ATA GAA CTC AAA GAT GAA GAA ATT GCA
 A   L   Q   E   N   E   K   L   H   K    E   I   E   L   K   D   E   E   I   A

421/141                                  451/151
CGT TTG AAA CAA GAA AAT GAC GAA TTA ATG  GAA CTT GCT GGG CAT GTA CAA TAC ATG GCT
 R   L   K   Q   E   N   D   E   L   M    E   L   A   G   H   V   Q   Y   M   A

481/161                                  511/171
AAT ATG ATT GAA AGG CTC ACT GGA AAT GCT  CCA CGA AGT CTT GAA GAC TTA AAG GAT TTG
 N   M   I   E   R   L   T   G   N   A    P   R   S   L   E   D   L   K   D   L

541/181                                  571/191
GAT TTG GAA GAA GCA AGA TTT GAA GAT GAA  GCA GAC ATG GCA GAA GCA AGG ATT GAA GAT
 D   L   E   E   A   R   F   E   D   E    A   D   M   A   E   A   R   I   E   D

601/201                                  631/211
GAA ACT GAC ATG GCT CGG CCC TCT AAT TCA  GAT CAG AAT ATG GAT GCA CAT ACT GTC TAG
 E   T   D   M   A   R   P   S   N   S    D   Q   N   M   D   A   H   T   V   *    (SEQ ID NO: 6)
```

GCTGTGAATTGACCACATGAGACTTAAAGTGGCCTGAAACATATTTAAAGATGTCATGGTCAGTGGAGGGTGGAAACATGCCATTT
TGTAATTGTCCAATGTTTTGGGAAGGGTTTAATTTCGGTGAAACTGACCTTAAACTACAGAACTTGCCATCTGAAAGTTTTTATCT
GCTAAATATTTAAGTTGGTCACTTGACAGACAAATACTATGTATTTCTTTATTGTAAATAGGTTTTTTTTAATGTTCCAGCCTTTAT
GTGAGGTGATTGTACATACTTGAATAAACTTCAGTTTTGAACGTGTTCTAAACAAAAAAAAAAAAAAAAAAAAAAAAAAAAAAAA
AAAAAAAA (SEQ ID NO: 18)

FIG. 21

Mouse Geminin

```
CATTGTGCGGCTCTCACGCTCGCCGGGAACTGAGCATTGCTGTCTGTGAGTCCGAGGGCGCGGGAGACCGAGGGCGGGGC
GAGTGCAACTCCGGCCGCGGGATCGCGGGCTGGCCCGAATGCCCGGCCTGCTTCTCAGCCACGGGGAGCCGGCCTGGGAG
GCGACGATTTGAAGGGTCTGCAGGTTCGGGTCGTTCTGGCGTCGTTGAATCCGGTGTGGTGCCAGGGCCTTGTGCGGCTC
TCACGCTCGCCGGGAACTGAGCATTGCTGTCTCTGAAAA
```

```
1/1                                          31/11
ATG AAT CTC AGT ATG AAG CAG AAG CAG GAG GGA GCC CAA GAG AAT GTG AAG AAT AGT CCT
 M   N   L   S   M   K   Q   K   Q   E   G   A   Q   E   N   V   K   N   S   P

61/21                                        91/31
GTC CCA AGG AGA ACG CTG AAG ATG ATC CAG CCT TCT GCA GAT GGA TCT CTT GTT GGC AGA
 V   P   R   R   T   L   K   M   I   Q   P   S   A   D   G   S   L   V   G   R

121/41                                       151/51
GAA AAT GAG TTG CCA AAA GGC TTG TTC AAA AGG AAG CTT TGG GAT GAC CAG CTA GCA TCT
 E   N   E   L   P   K   G   L   F   K   R   K   L   W   D   D   Q   L   A   S

181/61                                       211/71
CAG ACT TCA AGC TGT GGT CCA GAA GCT AAT GAA AAT AAG GAT GTT GGA GAC CTC ACC CAG
 Q   T   S   S   C   G   P   E   A   N   E   N   K   D   V   G   D   L   T   Q

241/81                                       271/91
GAA GCC TTT GAT CTT ATA AGT AAA GAG AAC CCA TCT TCT CAG TAT TGG AAA GAA GTG GCA
 E   A   F   D   L   I   S   K   E   N   P   S   S   Q   Y   W   K   E   V   A

301/101                                      331/111
GAG CAG CGG AGG AAA GCT CTC TAC GAA GCG CTG AAA GAG AAT GAG AAA CTT CAT AAA GAA
 E   Q   R   R   K   A   L   Y   E   A   L   K   E   N   E   K   L   H   K   E

361/121                                      391/131
ATT GAA CAA AAG GAC AGT GAG ATT GCC CGC CTG AGA AAG GAG AAT AAA GAC TTG GCA GAA
 I   E   Q   K   D   S   E   I   A   R   L   R   K   E   N   K   D   L   A   E

421/141                                      451/151
GTA GCT GAG CAC GTG CAG TAC ATG GCG GAG GTA ATC GAG AGG CTG AGT AAT GAA CCT CTG
 V   A   E   H   V   Q   Y   M   A   E   V   I   E   R   L   S   N   E   P   L

481/161                                      511/171
GAT AAC TTT GAA TCA CCG GAT AGT CAG GAA TTT GAT TCT GAA GAA GAA GCT GTT GAG TAT
 D   N   F   E   S   P   D   S   Q   E   F   D   S   E   E   E   A   V   E   Y

541/181                                      571/191
TCA GAA CTG GAA GAC TCA GGA GCT GGG ACG TGT GCT GAA GAG ACT GTG TCT TCC TCC ACG
 S   E   L   E   D   S   G   A   G   T   C   A   E   E   T   V   S   S   S   T

601/201
GAT GCT AGG CCG TGT ACA TGA
 D   A   R   P   C   T   *   (SEQ ID NO: 7)
```

```
GGTGTGGGACGCACTGCCAGCGTTGCCCTTTAGTATAGCTCTTGGTAAACTAACTACACGGTGCAAGTGCTGGAAGCCAG
GTTTGAATCCTGGGGCTATCACTATGTTAAAATACAGATAGTGTGTATTTTTAATCCGTTTTATGTAAATAGCATTTTCA
TTTTTGTCAGTGTCAGATATAAACTGTATATTAAATAAACTTCAATTTCCTGTTGAACATT (SEQ ID NO: 19)
```

FIG. 22

Human Geminin

TCTTCTGTGCTTCACCATCTACATA

```
1/1                                            31/11
ATG AAT CCC AGT ATG AAG CAG AAA CAA GAA GAA ATC AAA GAG AAT ATA AAG AAT AGT TCT
 M   N   P   S   M   K   Q   K   Q   E   E   I   K   E   N   I   K   N   S   S

61/21                                          91/31
GTC CCA AGA AGA ACT CTG AAG ATG ATT CAG CCT TCT GCA TCT GGA TCT CTT GTT GGA AGA
 V   P   R   R   T   L   K   M   I   Q   P   S   A   S   G   S   L   V   G   R

121/41                                         151/51
GAA AAT GAG CTG TCC GCA GGC TTG TCC AAA AGG AAA CAT CGG AAT GAC CAC TTA ACA TCT
 E   N   E   L   S   A   G   L   S   K   R   K   H   R   N   D   H   L   T   S

181/61                                         211/71
ACA ACT TCC AGC CCT GGG GTT ATT GTC CCA GAA TCT AGT GAA AAT AAA AAT CTT GGA GGA
 T   T   S   S   P   G   V   I   V   P   E   S   S   E   N   K   N   L   G   G

241/81                                         271/91
GTC ACC CAG GAG TCA TTT GAT CTT ATG ATT AAA GAA AAT CCA TCC TCT CAG TAT TGG AAG
 V   T   Q   E   S   F   D   L   M   I   K   E   N   P   S   S   Q   Y   W   K

301/101                                        331/111
GAA GTG GCA GAA AAA CGG AGA AAG GCG CTG TAT GAA GCA CTT AAG GAA AAT GAG AAA CTT
 E   V   A   E   K   R   R   K   A   L   Y   E   A   L   K   E   N   E   K   L

361/121                                        391/131
CAT AAA GAA ATT GAA CAA AAG GAC AAT GAA ATT GCC CGC CTG AAA AAG GAG AAT AAA GAA
 H   K   E   I   E   Q   K   D   N   E   I   A   R   L   K   K   E   N   K   E

421/141                                        451/151
CTG GCA GAA GTA GCA GAA CAT GTA CAG TAT ATG GCA GAg CTA ATA GAG AGA CTG AAT GGT
 L   A   E   V   A   E   H   V   Q   Y   M   A   E   L   I   E   R   L   N   G

481/161                                        511/171
GAA CCT CTG GAT AAT TTT GAA TCA CTG GAT AAT CAG GAA TTT GAT TCT GAA GAA GAA ACT
 E   P   L   D   N   F   E   S   L   D   N   Q   E   F   D   S   E   E   E   T

541/181                                        571/191
GTT GAG GAT TCT CTA GTG GAA GAC TCA GAA ATT GGC ACG TGT gCT GAA GGA ACT GTA TCT
 V   E   D   S   L   V   E   D   S   E   I   G   T   C   A   E   G   T   V   S

601/201
TCC TCT ACG GAT GCA AAG CCA TGT ATA TGA
 S   S   T   D   A   K   P   C   I   *    (SEQ ID NO: 8)
```

AATGCATTAATATTTGACTGTTGAGAATTTTACTGCCGAAGTTTACCTCCACTAGTTCTTTGTAGCAGAGTACATAACTA
CATAATGCCAACTCTGGAATCAAATTTCCTTGTTTGAATCCTGGGACCCTATTGCATTAAAGTACAAATACTATGTATTT
TTAATCTATGATGGTTTATGTGAATAGGATTTTCTCAGTTGTCAGCCATGACTTATGTTTATTACTAAATAAACTTCAAA
CTCCTGTTGAACATTGTGTATAACTTAGAATAATGAAATATAAGGAGTATGTGTAGAAAAAAAAAA (SEQ ID NO: 20)

FIG. 23

GEMININ GENE AND PROTEIN

RELATED APPLICATION(S)

This application claims the benefit of U.S. Provisional Application No. 60/085,371 filed May 13, 1998, entitled, "Geminin Gene and Protein," the contents of which are incorporated herein by reference in their entity.

FUNDING

The invention was supported, in whole or in part, by a grant K08-HL03461-01 from the National Institutes of Health. The Government has certain rights in the invention. Also, the invention was supported by the Howard Hughes Medical Institute, grant number K08-HL3461-01, and the cancer research fund of the Damon Runyon-Walter Winchell Foundation, grant number 1325.

BACKGROUND OF THE INVENTION

Proliferative diseases such as cancer are a leading cause of death for persons of certain age groups. Uncontrollable or abnormal cell replication is a common characteristic of cancers. Much research is performed in an attempt to determine a cause of cancer and other proliferative diseases. In addition, much effort has gone into determining ways to regulate or control cellular replication, and in particular, the mechanisms which inhibit cellular replication. A need exists to modulate, enhance or inhibit cell division and/or DNA replication.

Significant research has also been performed in the area of neurological diseases or conditions. Examples of such diseases or conditions are Parkinson's disease, Alzheimer's disease, multiple sclerosis, and patients with spinal cord injuries. Patients with neurological diseases or conditions do not have curative or effective treatment options. Scientists are attempting to determine the mechanisms controlling neural development and, in particular, ways to promote neural growth and regeneration. A need exists to promote neurogenesis or the ability to facilitate neural differentiation.

SUMMARY OF THE INVENTION

The invention relates to a protein, called Geminin, which inhibits DNA or cellular replication and promotes neural growth. The C-terminus of Geminin inhibits DNA replication and the N-terminus promotes neural growth, also referred to as neurogenesis. The Geminin protein comprises domains with specific functions. For example, the protein has a replication inhibitory domain which inhibits DNA replication. Within this replication inhibitory domain is a coiled-coil domain which is the site of protein-protein interaction. Geminin also has a domain which elicits neurogenesis. Another domain of the Geminin protein is the destruction box domain, which is responsible for degradation of the Geminin protein upon poly-ubiquitination.

Therefore, the invention encompasses the nucleic acid sequence and the encoded amino acid sequence of the entire Geminin protein, the N-terminal portion, the C-terminal portion, the replication inhibitory domain and the destruction box sequence. The invention also pertains to a nucleic acid sequence and the encoded amino acid sequence of the C-terminus or replication inhibitory domain with a mutated, deleted, or non-functional destruction box sequence. A mutated, deleted, or non-functional destruction box sequence causes a protein that is refractory to poly-ubiquitin mediated degradation.

The invention also relates to an antibody or antibody fragment which binds to a portion of the Geminin protein. An antibody can be a monoclonal or polyclonal antibody. The antibody can inhibit Geminin function or its interaction with other proteins.

The invention also pertains to a plasmid or vector comprising a nucleic acid sequence which encodes the Geminin protein or a portion thereof, as described herein. A cell or bacterial strain may also be transfected with the nucleic acid that encodes a Geminin protein or a portion thereof. Additionally, the invention relates to a fusion protein having an amino acid sequence of a Geminin protein or a portion thereof conjugated with a portion of an immunoglobulin or an antibody binding domain.

The invention includes methods for inhibiting or enhancing DNA replication in cells by administering a Geminin protein, an agonist or an antagonist thereof. Furthermore, the invention relates to methods for treating patients with proliferative diseases, including cancer, by administering the same.

The invention also includes methods for inhibiting or enhancing neural growth or neurogenesis in cells by administering the Geminin protein, agonists or antagonists thereof. Consequently, the invention also pertains to methods for treating patients with a neurological disease, disorder, or condition. Examples of such diseases, disorders, or conditions are Parkinson's disease, Alzheimer's disease, multiple sclerosis, and a patient with a spinal cord injury. Such a method embodies transfecting the nucleic acid which encodes at least a portion of the N-terminus of Geminin into embryonic ectodermal cells, maintaining the cells in conditions suitable for cell differentiation and/or cell division, and then transplanting these cells into the injured or affected neural area.

BRIEF DESCRIPTION OF THE DRAWINGS

The foregoing features and advantages of the invention will be apparent from the following more particular description of preferred embodiments of the invention, as illustrated in the accompanying figures. Emphasis is placed on illustrating the principles of the invention.

FIG. 1 illustrates the amino acid sequences of the Xenopus, mouse, and human Geminin proteins. The predicted amino acid sequences of Xenopus (SEQ ID NO: 5,6), mouse (SEQ ID NO: 7), and human (SEQ ID NO: 8) Geminin were aligned using the CLUSTAL method. Amino acids identical with the Xenopus Geminin-H (SEQ ID NO: 6) sequence are shaded. The destruction box and predicted coiled-coil region are indicated by rectangles. The coiled-coil region was identified using the PARCOIL algorithm.

FIG. 2A Geminin is mitotically degraded. [$^{35}$S]-methionine labeled Geminin-H was incubated with interphase extract, mitotic extract, or mitotic extract containing 100 μg/ml cyclin B1 D-box peptide. Proteins were detected by electrophoresis and autoradiography.

FIG. 2B shows the Domains of Geminin-H. A series of deletion and point mutations was constructed by site-directed mutagenesis. The small rectangle indicates the destruction sequence RRTLKVIQP (SEQ ID NO.: 33), and the large rectangle indicates the predicted coiled-coil region. The name of each mutant indicates whether the deletion is from the N or the C terminus and the amino acid at which the deletion ends. The half life of each construct in mitotic extract was measured as in (A). The percent of control DNA replication occurring in the presence of each mutant (50–64 mg/ml) is also indicated. The average result for two independent experiments is reported.

FIG. 2C illustrates that Geminin is ubiquitinated by APC in vitro. [$^{35}$S]-methionine labeled Geminin$^{WT}$ or Geminin$^{DEL}$ was incubated in a reaction mixture containing ATP, ubiquitin, bacterially expressed proteins E1 and UbcX, and APC immunoprecipitated from a mitotic extract with anti-cdc27 serum. The arrowhead indicates full-length Geminin$^H$. The two smaller bands represent false initiation by the reticulocyte extract at two internal AUGs. Lanes 1–4: Ubiquitin conjugates formed at t=0 and t=60 min. Lanes 5–8: Same as lane 2, except various conditions were altered.

FIG. 3A characterizes the anti-Geminin antibodies by immunoblotting. (FIG. 3A, Right) Lanes 1–2: in vitro translated Geminin-H (SEQ ID NO:6) and Geminin-L (SEQ ID NO: 5); Lanes 3 and 6: proteins immunoprecipitated from extract by anti-Geminin antibodies (two independent samples); Lane 4: crude egg extract; Lane 5: proteins immunoprecipitated by pre-immune rabbit IgG; Lane 6: crude HeLa cell extract. The positions of the molecular weight standards are indicated on the left. (FIG. 3A, Left) Demonstrates the immunodepletion of Geminin from CSF-arrested egg extracts. Supernates of extracts that had been treated with anti-Geminin antibody (lane 2) or rabbit IgG (lane 3) were immunoblotted with anti-Geminin antibodies. The arrowhead indicates the doublet of Geminin bands. Untreated extract is in lane 8.

FIG. 3B shows that Geminin is a nuclear protein. Asynchronous XL177 cells were stained with DAPI and with anti-Geminin antibodies. The arrowhead indicates an anaphase cell. The nucleus labeled "2" stains for Geminin but the nucleus labeled "1" does not.

FIG. 3C are histograms of DNA content for cells staining for Geminin (closed circles), cells not staining for Geminin (open circles), and all cells (closed triangles).

FIG. 3D illustrates when there is an abundance of the Geminin protein during the cell cycle. HeLa cells were arrested just after the G1/S transition using a double-thymidine block. At various times after release, the percentage of cells in each cell cycle phase was determined by FACS analysis and the amount of Geminin was determined by immunoblotting.

FIGS. 4A–C show that one cell of a two cells Xenopus embryo was injected with either GST, undegradable Geminin$^{DEL}$, or cyclin B_90. Photographs were taken three hours later. The arrowhead marks the site of injection. FIGS. 4D–E show that both cells of a two cells Xenopus embryo were injected with GST or undegradable Geminin$^{DEL}$. After 16 hours the embryos were fixed, sectioned, and stained with Hoechst 33258 dye. Both sections are shown at the same magnification. Two anaphase figures are indicated by arrows.

FIG. 5 illustrates that Geminin inhibits DNA replication.

In FIG. 6A, Geminin was added to a standard replication assay at different concentrations, and the amount of replication was determined. In FIG. 6B, high speed supernate was prepared from the same extract, and Geminin was added at various concentrations. After a 30 minute incubation, the samples were placed on ice and the chromatin was pelleted and resuspended in protein sample buffer. Immunoblots were performed using antibodies to Xorc2, Xcdc6, or Xmcm3.

(FIG. 9A) synaptobrevin (Knecht et al., 1995; Richter et al., 1988) expression in the olfactory placode is expanded on the Geminin-injected side of the embryo (15 pg full length RNA injected). (FIGS. 9B–C) otx 2 expression on Geminin-injected (FIG. 9B) or uninjected (FIG. 9C) sides of the same embryo. In B, otx 2 expression is expanded posteriorly and the otic vesicle and branchial arches fail to form normally. (FIGS. D–F) In situ hybridization for twist and injected Geminin. Injection of 250 pg of Ngem RNA eliminates twist staining (FIGS. 9D–E), whereas injection of 25 pg of Ngem expands twist expression on the injected (right) side relative to the control half (FIG. 9F). (FIGS. 9G–I) Animal hemisphere views of late gastrula stained to detect epidermal keratin and either 250 pg injected Ngem (FIGS. 9G, H) or 250 pg injected GFP (FIG. 9I). In FIGS. 9G and H, epidermal keratin staining is lost in injected cells; in FIG. 9I, overlap of GFP and keratin produces a stain.

FIGS. 10A–C show the structure, intracellular localization, and developmental profile of Geminin expression in embryos. (FIG. 10A) Protein sequences of Geminin for the following species are shown: Xenopus H (SEQ ID NO: 5), Xenopus L (SEQ ID NO: 6), mouse (SEQ ID NO: 7) and human (SEQ ID NO: 8). The N-terminal domain sufficient for neuralization is overscored and the C-terminal coiled-coil domain is overscored. (FIG. 10B) A myc-epitope tagged Geminin localizes to the nucleus of injected embryonic cells. (FIG. 10C) RT-PCR analysis of Geminin RNA levels in the embryo during development. Between stage 10 and 10.25, embryos were analyzed whole (W) or subdivided into dorsal (D) or ventral (V) halves. New (zygotic) transcription of Geminin is evident at stage 9 and in the dorsal half of the embryo at stage 10.

(FIGS. 11A, B, E, G, I–K) Geminin staining is in singly stained embryos. (FIGS. 11C, D, F, H) Geminin expression is in doubly-stained embryos. The expression patterns are brachyury (FIGS. 11C, D), BMP4 (FIG. 11F), or X-Delta-1 (FIG. 11H). (FIG. 11L) Geminin expression detected in a section of an e15 mouse embryo. Dorsal is oriented to the right (FIGS. 11B–D), top (FIGS. 11E–F) or facing out (FIGS. 11G–H). Xenopus embryos are stages 4 (FIG. 11A), 10 (FIG. 11B), 10.25 (FIGS. 11C, D), 12 (FIG. 11F), 12.5 (FIG. 11E), 13.5 (FIG. 11G), 20 (FIG. 11H), 28 (FIG. 11I), and 38 (FIGS. 11J, K).

FIGS. 12A and B are lateral views; FIG. 12C is an animal hemisphere view; embryos are stage 12 and dorsal is to the right. (FIG. 12D) BMP4 expression is down-regulated in ectoderm injected with Ngem RNA. Expression of endogenous Geminin is induced by injected Ngem (primers recognize the 3' untranslated region not included in the injected RNA). Muscle actin is not induced by Geminin.

(FIGS. 13A–F) Double in situ hybridizations with epidermal keratin and Geminin probes at stages 10– (FIG. 13A), 10+ (FIGS. 13B, C), 12.5 (FIG. 13D) or 12 (FIGS. 13E, F). FIGS. 13A and C are dorsal views (arrowheads mark the dorsal lip); FIGS. 13B, E and F are animal hemisphere views. (FIG. 13E) Coinjection of BMP4 and Geminin; tissue expresses both epidermal keratin and injected Geminin. (FIG. 13F) Coinjection of Geminin and GFP. Epidermal keratin expression is suppressed in regions expressing injected Geminin.

(FIG. 14A) Geminin expression in response to inducing molecules, (FIG. 14B) induction of neural gene expression by Geminin, (FIGS. 14C–F) immunostaining for N-CAM in animal caps injected with pUASgem (FIG. 14C), uninjected animal caps (FIG. 14D), or embryos injected in one bilateral half with pUASgem (FIGS. 14E–F).

(FIGS. 15A–D) in situ hybridization to detect epidermal keratin and injected Geminin endogenous not visible); overlap produces a dark stain. Embryos are stage 12. (FIGS. 15A, B) Dorsal views of embryos injected with the Geminin C-terminal domain expression plasmid (pCdim). (FIGS. 15C, D) Embryos injected with a plasmid encoding both Cdim and full-length Geminin (pCdim-gem; 100 pg) and with a plasmid encoding full length Geminin (pCMVgem; 100 pg). A remaining keratin-expressing dorsal cell is indicated by an arrowhead. (FIGS. 15E–F) in situ hybridization to detect N-tubulin F) and ectopically expressed Geminin in transgenic embryos expressing either pCdim (FIG. 15E) or pCdim-gem (FIG. 15F). Embryos in FIGS. 15E, F are stage 23/24.

FIG. 16 shows the nucleotide sequence (SEQ ID NO: 1) and the corresponding amino acid sequence (SEQ ID NO: 5) of Xenopus Geminin-L.

FIG. 17 shows the nucleotide sequence (SEQ ID NO: 2) and the corresponding amino acid sequence (SEQ ID NO: 6) of Xenopus Geminin-H.

FIG. 18 shows the nucleotide sequence (SEQ ID NO: 3) and the corresponding amino acid sequence (SEQ ID NO: 7) of Mouse Geminin.

FIG. 19 shows the nucleotide sequence (SEQ ID NO: 4) and the corresponding amino acid sequence (SEQ ID NO: 8) of Human Geminin.

FIG. 20 shows the nucleic acid sequence and the corresponding amino acid sequence (SEQ ID NO: 5, 21) of Xenopus Geminin-L, with additional flanking nucleotide sequence (SEQ ID NO: 17).

FIG. 21 depicts the nucleic acid sequence and the corresponding amino acid sequence (SEQ ID NO: 6, 22) of the Xenopus Geminin-H, with additional flanking nucleotide sequence (SEQ ID NO: 18).

FIG. 22 illustrates the nucleic acid sequence and the corresponding amino acid sequence (SEQ ID NO: 7, 23) of the mouse Geminin, with additional flanking nucleotide sequence (SEQ ID NO: 19).

FIG. 23 shows the nucleic acid sequence and the corresponding amino acid sequence (SEQ ID NO: 8, 24) of human Geminin, with additional flanking nucleotide sequence (SEQ ID NO: 20).

DETAILED DESCRIPTION OF THE INVENTION

Figures 2A, 2B:
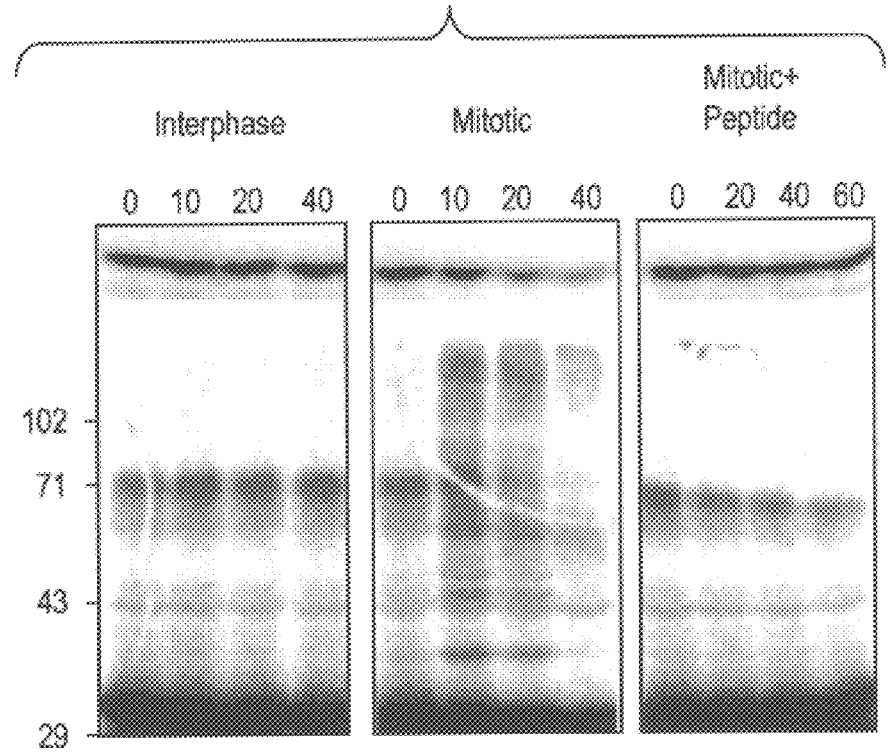
FIGS. 2A–C illustrates that Geminin is degraded by the APC Pathway.

The invention encompasses the Geminin protein (SEQ ID NO: 5, 6, 7, or 8) and functional portions thereof. The protein has two portions: a N-terminus and a C-terminus (SEQ ID NO: 37, 38, 39 or 40). The N-terminus (SEQ ID NO: 29, 30, 31, or 32) includes portions beginning with the first amino acid at the N-terminus up to and including amino acid number 111, such as, 38–90, while the C-terminus includes portions from amino acid numbers 112 up to and including amino acid 168. These portions comprise the entire sequence of the N-terminus component, the entire sequence of the C-terminus component or less than the entire sequence (e.g., fewer than amino acids 1–111 at the N-terminus, fewer than amino acids 112–168 at the C-terminus). The protein has a molecular weight of approximately 25 kD. The N-terminus, or amino terminus, has a destruction box sequence which comprises the amino acid sequence of RRTLKVIQP (SEQ ID NO.: 33). This destruction box sequence is homologous to the destruction box consensus sequence of mitotic cyclins. This destruction box sequence is positioned at amino acids 33–41 of Geminin. A protein also has a coiled-coil domain ranging from amino acids 118–152. This coiled-coil domain is the site for protein-protein interaction. The protein also has clusters of basic amino acids between positions 50–115 which serve as a nuclear localization signal or as sites for ubiquitin attachment. The protein also has a replication inhibitory domain (SEQ ID NO: 9, 10, 11 or 12) which lies between amino acids 80 and 160, a region which includes the predicted coiled-coil domain. In particular, a fragment of Geminin-L consisting only of amino acids 87–168 is sufficient to inhibit replication. Therefore, the claimed invention includes not only the entire Geminin protein but the various functional portions thereof. In particular, the claimed invention relates to the N-terminus, the C-terminus, the destruction box sequence, the coiled-coil domain and the inhibitory DNA replication domain, and functional combinations thereof.

The following table lists the various sequence identification numbers and the description of the sequence.

| SEQ ID NO: | Description |
|---|---|
| 1 | the Xenopus nucleic acid sequence of Geminin-L (e.g., FIGS. 1, 16, 20) |
| 2 | the Xenopus nucleic acid sequence of Geminin-H (e.g., FIGS. 1, 17, 21) |
| 3 | the mouse nucleic acid sequence of Geminin (e.g., FIGS. 1, 18, 22) |
| 4 | the human nucleic acid sequence of Geminin (e.g., FIGS. 1, 19, 23) |
| 5 | the Xenopus amino acid sequence of Geminin-L (e.g., FIGS. 1, 16, 20) |
| 6 | the Xenopus amino acid sequence of Geminin-H (e.g., FIGS. 1, 17, 21) |
| 7 | the mouse amino acid sequence of Geminin (e.g., FIGS. 1, 18, 22) |
| 8 | the human amino acid sequence of Geminin (e.g., FIGS. 1, 19, 23) |
| 9 | the Xenopus nucleic acid sequence of the replication inhibitory domain of Geminin-L (e.g., C-terminal domain or heptad repeats) |
| 10 | the Xenopus nucleic acid sequence of the replication inhibitory domain of Geminin-H (e.g., C-terminal domain or heptad repeats) |
| 11 | the mouse nucleic acid sequence of the replication inhibitory domain of Geminin (e.g., C-terminal domain or heptad repeats) |
| 12 | the human nucleic acid sequence of the replication inhibitory domain of Geminin (e.g., C-terminal domain or heptad repeats) |
| 13 | the Xenopus amino acid sequence of the replication inhibitory domain of Geminin-L (e.g., C-terminal domain or heptad repeats) |
| 14 | the Xenopus amino acid sequence of the replication inhibitory domain of Geminin-H (e.g., C-terminal domains or heptad repeats) |
| 15 | the mouse amino acid sequence of the replication inhibitory domain of Geminin (e.g., C-terminal domain or heptad repeats) |
| 16 | the human amino acid sequence of the replication inhibitory domain of Geminin (e.g., C-terminal domain or heptad repeats) |
| 17 | the Xenopus nucleic acid sequence with flanking sequence of Geminin-L (e.g., FIG. 20) |
| 18 | the Xenopus nucleic acid sequence with flanking sequence of Geminin-H (e.g., FIG. 21) |
| 19 | the mouse nucleic acid sequence with flanking sequence of Geminin (e.g., FIG. 22) |
| 20 | the human nucleic acid sequence with flanking sequence of Geminin (e.g., FIG. 23) |
| 21 | the Xenopus amino acid sequence with flanking sequence of Geminin-L (e.g., FIG. 20) |
| 22 | the Xenopus amino acid sequence with flanking sequence of Geminin-H (e.g., FIG. 21) |
| 23 | the mouse amino acid sequence with flanking sequence of Geminin (e.g., FIG. 22) |
| 24 | the human amino acid sequence with flanking sequence of Geminin (e.g., FIG. 23) |
| 25 | the Xenopus N-terminal domain nucleic acid sequence of Geminin-L (e.g., neutralizing domain) |
| 26 | the Xenopus N-terminal domain nucleic acid sequence of Geminin-H (e.g., neutralizing domain) |
| 27 | the mouse N-terminal domain nucleic acid sequence of Geminin (e.g., neutralizing domain) |
| 28 | the human N-terminal domain nucleic acid sequence of Geminin (e.g., neutralizing domain) |
| 29 | the Xenopus N-terminal domain amino acid sequence of Geminin-L (e.g., neutralizing domain) |
| 30 | the Xenopus N-terminal domain amino acid sequence of Geminin-H (e.g., neutralizing domain) |
| 31 | the mouse N-terminal domain amino acid sequence of Geminin (e.g., neutralizing domain) |
| 32 | the human N-terminal domain amino acid sequence of Geminin (e.g., neutralizing domain) |
| 34 | the Xenopus C-terminal domain nucleic acid sequence of Geminin-H |
| 35 | the mouse C-terminal domain nucleic acid sequence of Geminin |
| 36 | the human C-terminal domain nucleic acid sequence of Geminin |
| 37 | the Xenopus C-terminal domain amino acid sequence of Geminin-L |
| 38 | the Xenopus C-terminal domain amino acid sequence of Geminin-H |
| 39 | the mouse C-terminal domain amino acid sequence of Geminin |
| 40 | the human C-terminal domain amino acid sequence of Geminin |
| 41 | the Xenopus nucleic acid sequence of the replication inhibitory domain of Geminin-L |
| 42 | the Xenopus nucleic acid sequence of the replication inhibitory domain of Geminin-H |

The Structure of Geminin

The invention encompasses proteins from various species. In particular, the inventors have isolated the Geminin protein in Xenopus (SEQ ID NO: 5, 6, 21 or 22), mouse (SEQ ID NO: 7 or 23), and human (SEQ ID NO: 8 or 24) species. Two Xenopus versions of the Geminin protein exist: Geminin-H and Geminin-L. These two versions of Geminin, found in the Xenopus genus, are non-allelic isoforms. Geminin-H is 219 amino acids long and Geminin-L is 216 amino acids long. Additionally, the inventors have isolated the human and murine homologues. Both the murine and mouse homologues are approximately 45% identical to the Xenopus amino acid sequence. However, for the more conserved regions, the mouse and human homologues are greater than 70% identical (e.g., 77–80%). The bacterial strains which make each of the Geminin homologues have been deposited with the following designations: BL21::pET28(a) Geminin-H from Xenopus, DH5::pET28(a) Geminin-L from Xenopus, DH10::833335 (mouse Geminin EST (#833335): vector pT3T7D-PAC,DH10::727990 (human Geminin EST (#727990): vector pT3T7D-PAC). These bacterial strains were deposited under conditions of the Budapest Treaty with the American Type Culture Collection (ATCC), 10801 University Boulevard, Manassas, Va. 20110-2209, USA on (date to be added) under accession number (to be added). The plasmids which encode Xenopus Geminin H and Xenopus Geminin L contain DNA encoding a histidine tag (derived from Novagen plasmid pET28(a), sequence MGSSHHHH-HHSSGLVPRGSH (SEQ ID NO.: 34)) fused to the geminin coding region. The histidine tag allows a skilled artisan to separate the recombinant geminin protein from the rest of the cellular material.

The four bacterial strains may be isolated or separated from each other using routine methods. To isolate the strains producing Xenopus geminin H and Xenopus geminin L, the culture could be streaked onto bacterial plates containing kanamycin. To isolate the strains producing human geminin and mouse geminin, the culture could be streaked onto bacterial plates containing the antibiotic ampicillin. Individual bacterial colonies on each plate will contain the plasmid for only one of the four geminin homologs. This plasmid DNA may be extracted by a skilled artisan using commercially available kits. Standard PCR reactions may be used to determine which of the four geminin homologs each plasmid DNA encodes. Specifically, a skilled artisan could synthesize four pairs of primers based on the sequences deposited in the GenBank database or enclosed herein. Each pair would match the sequence of only one of the four geminin homologs. Standard PCR reactions may be performed using plasmid DNA from each colony and each of the four pairs of primers. Only the primer pair which exactly matches the geminin sequence contained in the plasmid will successfully amplify the plasmid DNA.

Alternatively, a skilled artisan could ascertain which geminin homolog was encoded by each plasmid by performing restriction enzyme digests. Specifically, the purified plasmid DNA from each colony could be digested with restriction enzymes and the sizes of the DNA fragments produced may be determined by gel electrophoresis. Each of the four plasmids encoding one of the four geminin homologs produces a distinct characteristic pattern of fragments.

Furthermore, the sequences for the various homologues can be synthesized using recombinant methods based on the deposited sequences in the GenBank database or the sequences disclosed herein. Geminin proteins were deposited in the GenBank database under the following accession numbers: Xenopus Geminin-H (AF067856), Xenopus Geminin-L (AF068781), mouse Geminin (AF068780), and human Geminin (AF067855).

Hence, the invention embodies a nucleic acid transfected into the various deposited bacterial strains as well as the amino acid sequences encoded by the DNA transfected into the bacterial strains.

The Function of Geminin

The C-terminus is responsible for the inhibition of DNA replication. The N-terminus is primarily responsible for promoting neurogenesis.

Geminin inhibits DNA replication during certain phases of the cellular division cycle. The cell cycle can be broadly divided into two phases: interphase and mitosis. Interphase represents the time during which the cell engages in synthetic activities and reproduces its components. During a relatively short period, the cell undergoes mitosis. During mitosis, the cell undergoes division into two daughter cells. Each daughter cell contains two copies of each chromosome. Mitosis is accomplished by a series of events, also referred to as "phases." The first phase is referred to as "prophase" in which the 2 individual sets of each chromosome present in the nucleus of the cell become visible or apparent. The next phase is referred to as "prometaphase" in which the two chromosomes move toward the middle or the equator of the cell. During "metaphase," the chromosome are at their most compact state and they become aligned at the equator of the cell. In "anaphase," the sets of chromosomes are pulled to opposite poles of the cell. This movement results in the shortening of the chromosome fibers. The chromosomes reach the poles of the cell at "telophase," and then condense into chromatin while the nucleus is reformed. In the final phase of "cytokinesis," the two daughter cells separate and are pinched apart by the formation of a contractile ring consisting of actin filaments. The essence of mitosis, therefore, is that the chromosomes are pulled toward opposite poles of the cell, so that each daughter cell receives one copy of each set of chromosomes.

Interphase is subdivided into three phases: the G1 phase, the S phase, and the G2 phase. Three phases of interphase exist: the G1 phase, the S phase, and the G2 phase. Once the cells are released from mitosis, they enter into the G1 phase, during which RNAs and proteins are synthesized, but no DNA replication occurs. The initiation of DNA replication marks the transition from the G1 phase to the S phase. The S phase lasts until all of the DNA has been replicated. During the S phase, the total content of the DNA increases by two-fold. The period from the end of the S phase until mitosis is called the G2 phase, during which the cell's nucleus contains 2 sets of chromosomes, also referred to as a 4n state. The M phase simply refers to the phase during which the cell undergoes mitosis, as described above.

In accordance with the cell cycle, Geminin is absent during the G1 phase, but begins to accumulate and persists throughout the S, G2 and most of the M phase. Geminin is degraded throughout the metaphase/anaphase transition and remains low throughout the G1 phase (see Example 1). The destruction box sequence is responsible for specifically targeting Geminin for degradation at the metaphase/anaphase transition. The Geminin protein is capable of inhibiting the initiation of DNA replication. An 80 amino acid region which includes a coiled/coil domain is primarily responsible for the inhibition of DNA replication.

Ubiquitin targets the degradation of a large group of proteins, including Geminin. This protein degradation is important in cell cycle progression and in late mitotic events. If the destruction box sequence is mutated, deleted, or otherwise nonfunctional, the protein becomes stable in mitotic extracts. The anaphase promoting complex (APC) controls the levels of Geminin protein. APC is a molecular complex that facilitates the attachment of ubiquitin to Geminin. Consequently, when increased levels of active APC exist, Geminin levels decrease. Therefore, APC is active during the metaphase/anaphase transition. (see Example 1). Not only is Geminin degraded during certain mitotic phases, but Geminin also inhibits nuclear DNA replication. Geminin interferes with the sequential assembly of a pre-replication complex (pre-RC) on the DNA at origins of replication. The pre-RC is necessary to initiate nuclear DNA replication. The pre-RC is simply a series of proteins that are sequentially assembled. Some of these proteins are components of the mini-chromosome maintenance (MCM) complex. Geminin strongly inhibits the incorporation of MCM complex into pre-RC. Therefore, inhibiting the assembly of the pre-RC thereby inhibits DNA replication. The approximately 80 amino acid sequence, generally between amino acids 80 and 160 and more particularly, in Geminin-L amino acids 87–168, is necessary for such inhibition. (see Example 1)

The destruction box can be mutated, as described in Example 1. The term "mutation," as used herein, refers to any modification in a nucleic acid sequence encoding a Geminin protein. For example, the mutation can be a point mutation or the addition, deletion, insertion and/or substitution of more nucleotides or any combination thereof. Modifications can be, for example, conserved or non-conserved, natural or unnatural. For example, to make the destruction box non-functional, a point mutation can be made at the nucleic acid level so that the leucine at amino acid No. 36 is changed to alanine. As used herein, a mutant also refers to the polypeptide encoded by the mutated nucleic acid. The term "mutant" also refers to a polypeptide which differs by one, or more, amino acid residues from the wild type (naturally occurring) polypeptide.

Geminin has been found to be a nuclear protein. Once the protein is synthesized in the cytoplasm, it enters the nucleus of the cell. In the nucleus, Geminin is able to inhibit DNA replication. Results described in Example 1 illustrate that Geminin is primarily localized to the nucleus. Hence, the invention pertains to the C-terminal domain of Geminin, the replication inhibitory domain, or any other functional domain. The claimed invention also relates to methods for inhibiting DNA replication in cells by introducing a protein containing the replication inhibitory domain of Geminin, a nucleic acid encoding the same, or an agent which enhances Geminin activity or production. Additionally, the invention encompasses methods for enhancing DNA replication in cells by introducing a composition of an agent that specifically binds to the inhibitory domain of Geminin or inhibits activity or production thereof. The claimed invention also relates to methods of inhibiting DNA replication using natural or synthetic chemical compounds which mimic the action of geminin by virtue of the fact that they adopt a similar shape as the protein.

In addition to the DNA replication inhibition capabilities, the Geminin protein also possesses the ability to promote neurogenesis. The differentiation of neural cells occurs in the gastrulation stage of embryo development. Four stages of embryo development exist. The first stage is the "fertilization" stage in which the sperm and oocyte join to form the zygote. Immediately following fertilization, the "cleavage" stage begins. Cleavage is a series of extremely rapid mitotic divisions wherein the enormous volume of the zygote's cytoplasm is divided into numerous smaller cells. These cells are called blastomeres, and by the end of cleavage they generally form a sphere known as a blastula. After the rate of mitotic division has slowed down, the blastomeres undergo dramatic movements wherein they change their positions relative to one another. This series of extensive cell rearrangement is referred to as "gastrulation." As a result of gastrulation, the typical embryo contains three cell regions, called germ layers. The outer layer, referred to as the "ectoderm," produces the cells of the epidermis and the nervous system. The inner layer, referred to as the "endoderm," produces the lining of the digestive tube and its associated organs. The middle layer is called the "mesoderm" and gives rise to several organs including the heart, kidney and gonads as well as connective tissues and blood cells. Once these germ layers are established, the cells interact with one another and rearrange themselves to produce bodily organs in a process called "organogenesis."

The neurons of the nervous systems develop from the embryonic ectoderm layer which appears during gastrulation. In early embryonic stages, the future central nervous system separates by folding from the primitive ectoderm to form the neural tube. At the time the neural folds meet, some cells leave the junctional region bilaterally to form cellular bands between the neural tube and the prospective epidermis. These bands are referred to as the "neural crests." The neural crests become segmented and are the precursors for the craniospinal and sympathetic ganglia, adrenal medulla, and melanocytes. Schwann cells which are responsible for composing a continuous envelope around each nerve fiber, are also derivatives of the neural crests.

Geminin plays an essential early role in specifying neural cell fate. Geminin has the ability to cause ectodermal cells to differentiate into neural cells. Geminin appears to be found in the oocyte and throughout the late blastula. In the early gastrula, however, expression is restricted to the dorsal ectodermal territory that prefigures the neural plate.

Bone Morphogenetic Proteins (BMPs) promote epidermal differentiation and block neural differentiation in the ectoderm. Neural induction causes local suppression of BMP signaling. Inhibition of BMPs neuralizes ectodermal explants.

Geminin promotes neurogenesis. Neurogenesis is defined as the formation of the nervous system. Neurogenesis is illustrated by various functional characteristics. For example, neurogenesis includes the ability to neuralize ectoderm, promote neural inducers, induce early proneural genes, and inhibit neural patterning by a putative dominant negative domain. The ability to promote neurogenesis comes from the N-terminus of the Geminin protein. The domain responsible for Geminin's neurogenesis ability are amino acid numbers 38–90. In particular, this domain invokes neural hypertrophy and ectopic neurogenesis. Furthermore, this domain is capable of demarcating the future neural plate in the early gastrula. When Geminin mRNA becomes further restricted to the dorsal ectodermal territory, as described above, Geminin levels increase and enrich the dorsal area. Formation of the neural plate occurs on this dorsal surface. BMP4 expression, however, is restricted to the ventral ectoderm and mesoderm, while Geminin mRNA is restricted to the dorsal ectoderm.

In accordance with Geminin's ability to promote neurogenesis, Geminin possesses the ability to suppress BMP4 expression. Suppression of BMP4 expression discourages the expression of epidermal keratin, a protein required for epidermal differentiation. BMP4 is present in the dorsal ectoderm, but is down regulated by Geminin. More importantly, when Geminin is misexpressed (i.e., expressed in the ventral ectoderm as compared to the dorsal ectoderm), both BMP4 and epidermal keratin cannot illicit epidermal differentiation. Rather, Geminin is capable of inducing neural gene expression in isolated ectoderm. BMP4, however, has neither a stimulatory nor inhibitory affect on Geminin transcription. Geminin's ability to suppress BMP4 is in accordance with its neuralizing activity.

Thus, the invention relates to the N-terminal domain of the Geminin protein or the functional domain capable of eliciting neurogenesis. The invention further pertains to methods for enhancing or inhibiting neurogenesis in cells and involves introducing into the cell a composition containing a functional portion of the N-terminal domain, the entire N-terminal domain, DNA that encodes a functional portion of the N-terminal domain, or an agent which is capable of enhancing Geminin activity or production thereof. A method for inhibiting neurogenesis in cells includes introducing into cells a composition that is capable of binding to the N-terminal domain of Geminin or an agent which can inhibit Geminin activity or production thereof.

Forms of Geminin

The claimed invention is intended to encompass Geminin proteins, and proteins and polypeptides having amino acid sequences analogous to the amino acid sequences of the Geminin protein and functional equivalents thereof. Such polypeptides are defined herein as Geminin analogs (e.g., homologues) or derivatives. The claimed invention is also intended to embody the various functional domains as described herein. Analogous amino acid sequences are defined herein to mean amino acid sequences with sufficient identity to the Geminin amino acid sequence so as to possess the biological activity of a Geminin protein. For example, an analogous peptide can be produced with "silent" changes in amino acid sequence wherein one, or more, amino acid residues differ from the amino acid residues of the Geminin protein, yet still possess the biological activity of Geminin. Examples of such differences include additions, deletions or substitutions of residues of the amino acid sequence of Geminin. Also encompassed by the claimed invention are analogous polypeptides that exhibit greater, or lesser, biological activity of the Geminin protein of the claimed invention.

The "biological activity" of the Geminin protein is defined herein to mean inhibitory replication activity and/or the ability to promote neurogenesis in cells. The biological activity of Geminin is also defined by the various functional characteristics as described herein, and in particular, in Example 1 and Example 2.

The claimed invention also encompasses biologically active polypeptide fragments of the Geminin protein described herein. Such fragments can include only a part of a full length amino acid sequence of Geminin and yet possess either the inhibitory DNA replication affect or the ability to promote neurogenesis. For example, polypeptide fragments comprising deletion mutants of the Geminin protein can be designed and expressed by well known laboratory methods. Such polypeptide fragments can be evaluated for biological activity as described herein.

Biologically active derivatives or analogs of the above described Geminin protein, referred to herein as peptide mimetics can be designed and produced by techniques known to those of skill in the art. (see e.g., U.S. Pat. Nos. 4,612,132; 5,643,873 and 5,654,276, the teachings of which are incorporated herein by reference). These mimetics can be based, for example, on a specific Geminin amino acid sequence and maintain the relative position in space of the corresponding amino acid sequence. These peptide mimetics possess biological activity similar to the biological activity of the corresponding peptide compound, but possess a "biological advantage" over the corresponding Geminin amino acid sequence with respect to one, or more, of the following properties: solubility, stability and susceptibility to hydrolysis and proteolysis.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic molecule. Modifications of peptides to produce peptide mimetics are described in U.S. Pat. Nos. 5,643,873 and 5,654,276, the teachings of which are incorporated herein by reference. Other forms of the Geminin protein, encompassed by the claimed invention, include those which are "functionally equivalent." This term, as used herein, refers to any nucleic acid sequence and its encoded amino acid which mimics the biological activity of the Geminin protein and/or functional domains thereof. As described above, biologically active is used to describe a protein capable of inhibiting DNA replication and/or promoting neurogenesis.

A Geminin polypeptide can be in the form of a conjugate or a fusion protein which can be manufactured by known methods. Fusion proteins can be manufactured according to known methods of recombinant DNA technology. For example, fusion proteins can be expressed from a nucleic acid molecule comprising sequences which code for a biologically active portion of the Geminin protein and its fusion partner, for example a portion of an immunoglobulin molecule. For example, some embodiments can be produced by the intersection of a nucleic acid encoding immunoglobulin sequences into a suitable expression vector, phage vector, or other commercially available vectors. The resulting construct can be introduced into a suitable host cell for expression. Upon expression, the fusion proteins can be isolated or purified from a cell by means of an affinity matrix.

Antibodies can be raised to the Geminin protein, analogs, and portions thereof, using techniques known to those of skill in the art. These antibodies can be polyclonal, monoclonal, chimeric, or fragments thereof. These antibodies can be used to purify or identify the Geminin protein contained in a mixture of proteins, using techniques well known to those of skill in the art. These antibodies, or fragments thereof, can be used to detect the presence or absence of the Geminin protein using standard immunochemistry methods.

The invention also pertains to methods for determining the presence, absence or level of Geminin using an anti-Geminin antibody. The presence or absence of Geminin can be detected in an assay (e.g., ELISA or radioimmunoassay (RIA)). The assay can be a direct detection or an indirect detection (e.g. a competitive assay).

For example, to determine the presence or absence of Geminin using an ELISA assay in a suitable sample, the method comprises:

(a) combining
  (i) a suitable sample,
  (ii) a composition comprising a murine anti-Geminin antibody as detector, such as
    (a) biotinylated anti-geminin MAb and HRP-streptavidin, or
    (b) HRP-conjugated anti-Geminin Mab, and
  (iii) a solid support, such as a microtiter plate, having an anti-Geminin capture antibody bound (directly or indirectly) thereto,
  wherein the detector antibody binds to a different Geminin epitope from that recognized by the capture antibody, under conditions suitable for the formation of a complex between said anti-Geminin antibodies and Geminin; and
(b) determining the formation of complex in said samples.

The presence of Geminin can also be determined in a radioimmunoassay. For example, the presence of Geminin can be assessed by an immunobinding assay comprising:

(a) obtaining a sample;
(b) contacting said sample with a composition comprising an anti-Geminin antibody, such as
  (i) a murine anti-Geminin antibody comprising a radioactive label; or
  (ii) a murine anti-Geminin antibody comprising a binding site for a second antibody which comprises a radioactive label,
  preferably in an amount in excess of that required to bind the Geminin, under conditions suitable for the formation of labeled complexes and
(c) determining (detecting or measuring) the formation of complex in said samples.

Forms of Nucleic Acid

The claimed invention also encompasses isolated nucleic acid sequences encoding the Geminin protein described herein, and fragments of nucleic acid sequences encoding biologically active Geminin proteins. Fragments of the nucleic acid sequences described herein are useful as probes to detect the presence of the Geminin gene and mRNA in various species, or to screen cDNA libraries. The claimed invention also pertains to nucleic acid sequences encoding the Geminin protein, the fully complementary strands of these sequences and allelic variations thereof. Also encompassed by the claimed invention are nucleic acid sequences, DNA or RNA, which are substantially complementary to the DNA sequences encoding the Geminin protein, and which specifically hybridize with the Geminin DNA sequences under conditions of stringency known to those of skill in the art. Those conditions should be sufficient to identify DNA sequences with substantial sequence identity. As defined herein, substantially complementary means that the nucleic acid need not reflect the exact sequence of the Geminin DNA, but must be sufficiently similar in sequence to permit hybridization with Geminin DNA under stringent conditions. (see Examples 1 and 2) Conditions for stringency are described in e.g., Ausubel, F. M., et al., Current Protocols in Molecular Biology, (Current Protocol, 1994). For example, non-complementary bases can be interspersed in a nucleotide sequence, or the sequences can be longer or shorter than the Geminin DNA, provided that the sequence has a sufficient number of bases complementary to Geminin to allow hybridization therewith. Exemplary hybridization conditions are described herein and in standard texts, e.g., Ausubel, F. M., et al., Current Protocols in Molecular Biology, (Current Protocol, 1994). The Geminin DNA sequence, or a fragment thereof, can be used as a probed to isolate additional Geminin homologues. For example a cDNA or genomic DNA library from the appropriate organism can be screened with labeled Geminin DNA to identify homologues genes as described in e.g., Ausubel, F. M., et al., Current Protocols in Molecular Biology, (Current Protocol, 1994).

Typically, the nucleic acid probe comprises a nucleic acid sequence (e.g., SEQ ID NO:1) of sufficient length and complementarity to specifically hybridize to nucleic acid sequences which encode a Geminin protein. The requirements of sufficient length and complementarity can be easily determined by one of skill in the art. In fact, Examples 1 and/or 2 describe in detail such nucleic acid probes.

As used herein, an "isolated" gene or nucleotide sequence which is not flanked by nucleotide sequences which normally (e.g., in nature) flank the gene or nucleotide sequence (e.g., as in genomic sequences) and/or has been completely or partially purified from other transcribed sequences (e.g., as in a cDNA or RNA library). Thus, an isolated gene or nucleotide sequence can include a gene or nucleotide sequence which is synthesized chemically or by recombinant means. Nucleic acid constructs contained in a vector are included in the definition of "isolated" as used herein. Also, isolated nucleotide sequences include recombinant nucleic acid molecules and heterologous host cells, as well as partially or substantially or purified nucleic acid molecules in solution. In vivo and in vitro RNA transcripts of the claimed invention are also encompassed by "isolated" nucleotide sequences. Such isolated nucleotide sequences are useful for the manufacture of the encoded Geminin protein, as probes for isolating homologues sequences (e.g., from other mammalian species or other organisms), for gene mapping (e.g., by in situ hybridization), or for detecting the presence (e.g., by Southern blot analysis) or expression (e.g., by Northern blot analysis) of related Geminin genes in cells or tissue. As such, a further aspect of the invention relates to a novel, previously unknown or unidentified Geminin protein.

As described above, the term "fragment" is meant to encompass a portion of the biologically active Geminin protein or polypeptide; or a nucleotide sequence described herein which is at least approximately 25 contiguous nucleotides to at least approximately 50 contiguous nucleotides or longer in length. Such fragments are useful as probes for diagnostic purposes, experimental tools, or in the case of nucleic acid fragments, as primers. A preferred embodiment includes primers and probes which selectively hybridize to the nucleic acid constructs encoding the Geminin protein. For example, nucleic acid fragments which encode any one of the domains described above are also implicated by the claimed invention.

Nucleic acid molecules can be inserted into a construct which can, optionally, replicate and/or integrate into a recombinant host cell, by known methods. The host cell can be a eukaryote or prokaryote and includes, for example, yeast (such as *Pichia pastorius* or *Saccharomyces cerevisiae*) bacteria (such as *Escherichia coli* or *Bacillus subtilis*), animal cells or tissue, insect Sf9 cells (such as baculoviruses infected SF9 cells) or a mammalian cells (somatic or embryonic cells, Chinese hamster ovary cells, HeLa cells, human 293 cells and monkey COS-7 cells).

The invention also provides vectors or plasmids containing one or more of each of the Geminin homologues. Suitable vectors for use in eukaryotic and prokaryotic cells are known in the art and are commercially available or readily prepared by a skilled artisan. Additional vectors can also be found, for example, in Ausubel, F. M., et al., Current Protocols in Molecular Biology, (Current Protocol, 1994) and Sambrook et al., "Molecular Cloning: A Laboratory Manual," 2nd ED. (1989), the teachings of which are incorporated herein by reference.

The nucleic acid molecule can be incorporated or inserted into the host cell by known methods. Examples of suitable methods of transfecting or transforming cells include calcium phosphate precipitation, electroporation, microinjection, infection, lipofection and direct uptake. "Transformation" or "transfection" as used herein refers to the acquisition of new or altered genetic features by incorporation of additional nucleic acids, e.g., DNA. "Expression" of the genetic information of a host cell is a term of art which refers to the directed transcription of DNA to generate RNA which is translated into a polypeptide. Methods for preparing such recombinant host cells and incorporating nucleic acids are described in more detail in Sambrook et al., "Molecular Cloning: A Laboratory Manual," Second Edition (1989) and Ausubel, et al. "Current Protocols in Molecular Biology," (1992), for example.

The host cell is then maintained under suitable conditions for expression and recovery of Geminin. Generally, the cells are maintained in a suitable buffer and/or growth medium or nutrient source for growth of the cells and expression of the gene product(s). The growth media are not critical to the invention, are generally known in the art and include sources of carbon, nitrogen and sulfur. Examples include Luria broth, Superbroth, Dulbecco's Modified Eagles Media (DMEM), RPMI-1640, M199 and Grace's insect media. The growth Media may contain a buffer, the selection of which is not critical to the invention. The pH of the buffered Media can be selected and is generally one tolerated by or optimal for growth for the host cell.

The host cell is maintained under a suitable temperature and atmosphere. Alternatively, the host cell is aerobic and the host cell is maintained under atmospheric conditions or other suitable conditions for growth. The temperature should also be selected so that the host cell tolerates the process and can be for example, between about 13°–40° C.

Therapeutic Uses of Geminin

Compositions of the various forms of the Geminin protein are useful for therapeutic methods. To accomplish the various therapeutic treatments as described herein, a nucleic acid which encodes Geminin or a functional portion or domain thereof must be introduced into a mammalian cell (e.g., mammalian somatic cell, mammalian germ line cell (sperm and egg cells)). This can be accomplished by inserting the isolated nucleic acid that encodes either the full length Geminin protein, the C-terminal domain, the N-terminal domain, or the domains described herein, or a functional equivalent thereof, into a nucleic acid vector, e.g., a DNA vector such as a plasmid, virus or other suitable replicon (e.g., a viral vector), which can be present in a single copy or multiple copies. The nucleic acid may be transfected or transformed into cells using suitable methods known in the art such as electroporation, microinjection, infection, and lipoinfection and direct uptake. Such methods are described in more detail, for example, in Sambrook et al., "Molecular Cloning: A Laboratory Manual," 2nd ED. (1989), Ausubel, F. M., et al., Current Protocols in Molecular Biology, (Current Protocol, 1994) and Sambrook et al., "Molecular Cloning: A Laboratory Manual," 2nd ED. (1989).

The novel geminin of the claimed invention can be used to treat a proliferative or neurological condition/disease by delivering to cells the Geminin described herein in vitro or in vivo.

Geminin can be delivered to a cell by the use of viral vectors comprising one or more nucleic acid sequences encoding Geminin, the inhibitory replication domain with or without the destruction box sequence. Generally, the nucleic acid sequence has been incorporated into the genome of the viral vector. The viral vector containing Geminin described herein or nucleic acid sequences encoding the Geminin can be contacted with a cell in vitro and infection can occur. The cell can then be used experimentally to study, for example, unrestricted cell growth in vitro or be implanted into a patient for therapeutic use. The cell can be migratory, such as hematopoietic cells, or non-migratory such as a solid tumor or fibroblast. The cell can be present in a biological sample obtained from the patient (e.g., blood, bone marrow) and used in the treatment of disease, or can be obtained from cell culture and used to dissect cell proliferation pathways in in vivo and in vitro systems.

After contact with the viral vector comprising the Geminin protein or a nucleic acid sequence encoding Geminin, the sample can be returned or readministered to a cell culture or patient according to methods known to those practiced in the art. In the case of delivery to a patient or experimental animal model (e.g., rat, mouse, monkey, chimpanzee), such a treatment procedure is sometimes referred to as ex vivo treatment or therapy. Frequently, the cell is targeted from the patient or animal and returned to the patient or animal once contacted with the viral vector comprising the activated mutant of the present invention. Ex vivo gene therapy has been described, for example, in Kasid, et al., *Proc. Natl. Acad. Sci. USA* 87:473 (1990); Rosenberg, et al., *New Engl. J. Med.* 323:570 (1990); Williams, et al., *Nature* 310476 (1984); Dick, et al., *Cell* 42:71 (1985); Keller, et al., *Nature* 318:149 (1985) and Anderson, et al., U.S. Pat. No. 5,399,346 (1994).

Where a cell is contacted in vitro, the cell incorporating the viral vector comprising a nucleic acid sequence of Geminin can be implanted into a patient or experimental animal model for delivery or used in in vitro experimentation to study cellular events mediated by Geminin.

Various viral vectors can be used to introduce the Geminin nucleic acid into mammalian cell. Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In *Fundamental Virology*, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus, lentiviruses and baculoviruses.

A preferred method to introduce nucleic acid that encodes Geminin into cells is through the use of engineered viral vectors. These vectors provide a means to introduce nucleic acids into cycling and quiescent cells, and have been modified to reduce cytotoxicity and to improve genetic stability. The preparation and use of engineered Herpes simplex virus type 1 (D. M. Krisky, et al., Gene Therapy 4(10):1120–1125. (1997)), adenoviral (A. Amalfitanl, et al., Journal of Virology 72(2):926–933. (1998)), attenuated lentiviral (R. Zufferey, et al., Nature Biotechnology 15(9)871–875 (1997)) and adenoviral/retroviral chimeric (M. Feng, et al., Nature Biotechnology 15(9):866–870 (1997)) vectors are known to the skilled artisan.

Hence, the claimed invention encompasses various therapeutic uses for the Geminin protein or nucleic acid. In particular, the inhibitory replication domain with or without a non-functional (e.g., unable to cause degradation of the Geminin protein), mutated (e.g., substitute amino acid No. 36, leucine, with alanine) or deleted (e.g., delete amino acids 33–41 or a functional equivalent thereof) destruction box or a C-terminal domain of the Geminin protein can be administered to patients having a proliferative disease. Proliferative diseases are defined as a disorder/condition in which an abnormal rate of replication exists. An example of a proliferative disease is cancer. Various forms of the Geminin protein or nucleic acid, as described herein, can be administered and delivered to a mammalian cell (e.g., by virus or liposomes, or by any other suitable methods known in the art or later developed). The method of delivery can be modified to target certain cells, and in particular, cell surface receptor molecules or antigens present on tumor cells. Methods of targeting cells to deliver nucleic acid constructs are known in the art.

A Geminin protein may be administered using methods known in the art. For example, the mode of administration is preferably at the location of the target cells. As such, the administration can be nasally (as in administering a vector expressing ADA) or by injection (as in administering a vector expressing a suicide gene tumor). Other modes of administration (parenteral, mucosal, systemic, implant, intraperitoneal, etc.) are generally known in the art. The agents can, preferably, be administered in a pharmaceutically acceptable carrier, such as saline, sterile water, Ringer's solution, and isotonic sodium chloride solution.

Geminin can also be used in therapeutic methods for patients with neurological disorders, diseases, or conditions. The entire protein, the N-terminal portion of the protein (amino acid numbers 1–111) or functional and/or biologically active portions thereof (e.g., capable of promoting neurogenesis) can be introduced into mammalian cells, as described above. Examples of such neurological disorders, diseases, or conditions are Parkinson's disease, Alzheimer's disease, multiple sclerosis, or spinal cord injuries. Methods include transfecting nucleic acid that encodes the N-terminus portion of Geminin into embryonic ectodermal cells, and then maintaining the cells in conditions suitable for cell differentiation and division. The cells should be maintained so that the cells differentiate into neural cells. The method then entails transplanting the cells into the injured or affected neural area. Such a method is useful in the treatment of the above recited neurological diseases, disorders, or conditions.

The examples presented below are provided as further guidance and are not to be construed as limiting the invention in any way.

EXEMPLIFICATION

Example 1

Geminin: an Inhibitor of DNA Replication Is Degraded During Mitosis

Many events of the cell cycle are controlled through the proteolysis of key regulatory proteins. We describe a novel 25 kD protein, geminin, which is specifically degraded during the mitotic phase of the cell cycle. Geminin has a destruction box sequence near its amino terminus which is necessary for mitotic degradation. The protein is ubiquitinated by anaphase promoting complex (APC) in vitro. Antibodies raised against geminin show that the endogenous protein is localized to the nucleus. In synchronized HeLa cells, geminin is absent during G1 phase, accumulates during S, G2, and M phase, then disappears at the time of the metaphase to anaphase transition. Bacterially expressed geminin profoundly inhibits DNA replication in vitro. The protein prevents the complete assembly of pre-replication complex (pre-RC) at origins of DNA replication. In the presence of geminin, origin recognition complex (ORC) and Xcdc6 bind to the DNA but the MCM complex does not. When endogenous geminin is immunodepleted from Xenopus egg extracts, replication occurs normally and there is no re-replication. We propose that geminin inhibits DNA replication during S, G2, and M phase of the cell cycle, and that geminin destruction at the metaphase/anaphase transition permits replication in the succeeding cell cycle.

Many biochemical and cytological events of the cell cycle are coordinated by the proteolysis of key regulatory proteins. The degradation of B-type cyclins has been studied in the most detail. B-type cyclins are activating subunits of the mitotic kinase $p34^{cdc2}$, which is required for entry into mitosis. Mitotic kinase activity does not persist indefinitely because $p34^{cdc2}$ activates a proteolytic system that degrades B-type cyclins. With the loss of the activating subunit, $p34^{cdc2}$ kinase activity drops and the cells return to interphase. The critical importance of cyclin destruction in controlling the exit from mitosis is demonstrated by the effects of non-degradable mutant forms of cyclin B. These mutants retain the ability to activate $p34^{cdc2}$ but are missing the destruction box, a nine amino acid sequence which is recognized by the cyclin proteolytic system. If one of these mutants is introduced into cells, they become arrested in mitosis with condensed chromatin and high levels of $p34cdc^2$ kinase activity.

B-type cyclins are destroyed by ubiquitin mediated proteolysis. In this pathway, cyclin proteolysis is carried out in two steps. First, a covalently attached polymer of the small protein ubiquitin is built up on the cyclin. Then, a multisubunit protease complex called the proteasome recognizes and destroys the polyubiquitin-cyclin complex. The cyclin is degraded to small peptides and the polyubiquitin chain is disassembled back to ubiquitin monomers. The attachment of ubiquitin to cyclin occurs in three enzymatic steps. First, ubiquitin activating enzyme (E1) forms a high energy covalent bond to ubiquitin at the expense of ATP. Second, the activated ubiquitin is transferred to a second enzyme, ubiquitin conjugating enzyme (E2). In the case of cyclin B1, at least two different proteins can perform this second step in vitro, Ubc4 and UbcX/E2-C. Finally, the ubiquitin is transferred to cyclin by a 1.5 MD multiprotein complex called the anaphase promoting complex (APC) or the cyclosome. APC is thought to recognize the destruction box and attach ubiquitin to nearby lysine residues. The activity of APC is cell cycle regulated. APC isolated from mitotic cells ubiquitinates cyclin B with a much higher efficiency than APC isolated from interphase cells.

APC displays a remarkable degree of substrate specificity. It promotes the ubiquitination of a small number of proteins, all of which contain a destruction box sequence. For example, APC-mediated destruction of an "anaphase inhibitor" is required to bring about separation of sister chromatids on the mitotic spindle. The Pds1 protein from budding yeast and Cut2 protein from fission yeast show some of the expected characteristics of this inhibitor. Both proteins contain a destruction box sequence. In both cases, if this sequence is deleted or mutated, the protein is stabilized and the chromosomes fail to separate. APC also ubiquitinates Ase1p, a protein that binds to microtubules and promotes elongation of the spindle and separation of the spindle poles during anaphase Ase1p contains several sequences similar to the cyclin B destruction box, and the protein is stabilized if a particular one of these is mutated. The stable form of Ase1 delays disassembly of the spindle after mitosis, leading to damaged spindles in subsequent mitosis.

This paper describes a novel 25 kD protein, geminin, which is ubiquitinated by APC and mitotically degraded. Geminin contains a destruction box sequence near its amino terminus which is necessary for these reactions. In synchronized HeLa cells, geminin is absent during G1 phase, accumulates during S, G2, and M phase, and is degraded as the cells exit from mitosis. Bacterially expressed geminin dramatically inhibits the initiation of DNA replication in vitro. The protein interferes with the assembly of pre-replication complex at a point between the binding of Xcdc6 to chromatin and the binding of MCM complex. When endogenous geminin is removed from cell extracts by immunodepletion, a single complete round of DNA replication occurs. A model is presented for the biological function of geminin in cell cycle control.

Experimental Procedures

Xenopus Extracts and Embryos

Interphase, mitotic, and CSF-arrested Xenopus egg extracts were prepared as previously described. Xenopus eggs were collected, fertilized, and injected according to standard procedures. For histological sectioning, embryos were fixed in MEMFA (100 mM MOPS pH 7.4, 2 mM EGTA, 1 mM MgSO$_4$, and 3.7% formaldehyde). Paraffin embedded sections were stained with 0.5 µg/ml Hoechst 33258 dye.

Mutant Construction and Protein Stability Measurement

Deletion mutants of geminin H were made by PCR mutagenesis. The mutant genes were inserted into pET29(a) between the NdeI and XhoI sites. The sequences of the primers used to generate each mutant can be supplied on request. The DNA sequence of each mutant was confirmed by dideoxy sequencing. Degradation assays were performed as previously described.

Bacterial Protein Expression

The NdeI-XhoI DNA fragment encoding each geminin mutant was inserted into pET28(a). This manipulation attaches a hexahistidine tag to the 5' end of the coding sequence. A DNA fragment encoding GST was amplified from pGEX-3X and inserted into the same vector. The hexahistidine tagged proteins were expressed in E. coli strain BL21 and purified according to standard protocols (Qiagen). Proteins were dialyzed against 10 mM HEPES pH 7.7, 200 mM NaCl before use.

Antibodies

Hexahistidine tagged wild-type geminin H was used to immunize rabbits. Anti-geminin antibodies were purified by affinity chromatography using the immunogen coupled to CNBr activated sepharose 4B beads (Pharmacia). Immunoblots were performed according to standard procedures using the antibodies at 1:1000 dilution. For immunofluorescence, tissue culture cells were fixed with 4% formaldehyde in microtubule stabilizing buffer (MTSB: 80 mM Na-PIPES pH 6.8, 1 mM $MgCl_2$, 5 mM EGTA). The anti-geminin antibodies were used at a dilution of 1:1000–1:4500, and the secondary antibody (CY3 conjugated donkey anti-rabbit) was used at 1:500.

For immunodepletion of geminin, the affinity purified antibody was covalently attached to Affi-Prep protein A beads (BioRad) using dimethylpimelimidate (~1 mg antibody/1 µl beads). The beads were washed with CSF-XB and added to fresh CSF extract (5 µl beads/100 µl extract). The mixture was rotated at 4° C. for one hour and the supernate was recovered after brief microcentrifugation. A second aliquot of beads was added and the immunodepletion procedure was repeated.

Immunoprecipitations were performed as described previously. Geminin was eluted off the beads with 100 mM glycine pH 2.5, and the eluate was neutralized by adding 1/10 volume of 1 M Tris-HCl pH 8.0.

DNA Replication Assays

DNA replication was measured using CSF arrested Xenopus egg extracts and demembranated sperm. Density substitution with BrdUTP and CsCl gradient equilibrium centrifugation were performed as previously described.

Chromatin Binding Assays

Two different protocols which gave the same results were used to measure the binding of proteins to chromatin. In the first protocol, demembranated sperm were added to low-speed egg extract, which contains membrane bound cytoplasmic vesicles. After 20 min, the partially assembled nuclei were lysed by dilution into a buffer containing a nonionic detergent and the chromatin was pelleted through a sucrose cushion. In the second protocol, demembranated sperm were added to high speed egg extract which did not contain membranes. After allowing chromatin to assemble, sperm DNA and associated proteins were pelleted and resuspended in protein sample buffer. Electrophoresis and immunoblotting were performed using standard procedures.

Results

Structure of Geminin

A cDNA encoding geminin was initially isolated using a screening procedure designed to identify proteins that were degraded by mitotic Xenopus egg extracts but not by interphase egg extracts. The screen was very specific; the major proteins identified were B-type cyclins and geminin. A second geminin cDNA was isolated from a screening procedure designed to identify proteins that affected embryonic development. The proteins encoded by the two cDNAs are 89% identical at the amino acid level, and they seem to have identical properties (see below). Because of this close similarity, the protein was named geminin (L. gemini, twins). This paper discusses the role of geminin in the cell cycle, and the effects of geminin on embryonic development will be described herein.

Figure 1:
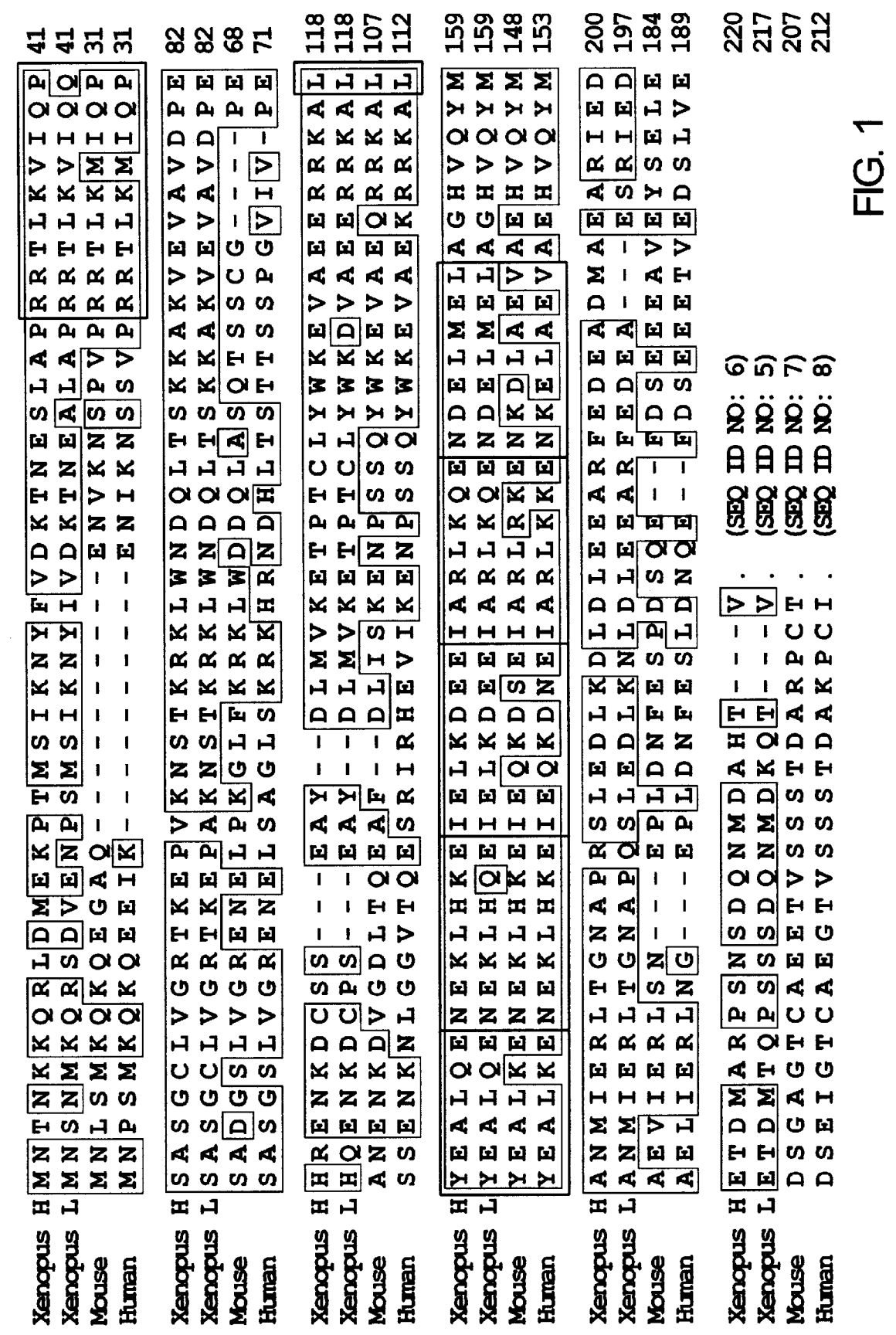
Figure 3A:
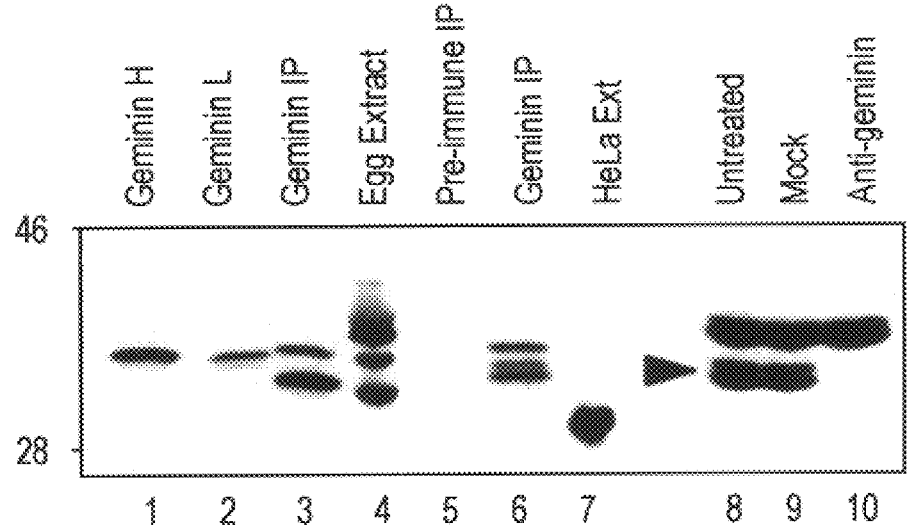
FIGS. 3A–D illustrates that Geminin is degraded in vivo.

The predicted amino acid sequence of the two geminin isoforms is given in FIG. 1. The proteins are 219 and 216 amino acids in length and have been designated geminin H and geminin L, respectively. Both proteins have a calculated molecular weight of about 25 kD, but they migrate aberrantly on polyacrylamide gels with an apparent molecular weight of about 35 kD (FIG. 3A). Neither protein shows any sequence homology to a previously characterized protein. Several structural motifs can be identified by inspection of the amino acid sequence. The amino terminal portion contains a short sequence RRTLKVIQP (SEQ ID NO.: 33) which has homology to the destruction box consensus sequence of mitotic cyclins (RxALGVIxN) (SEQ ID NO.: 35). This motif begins at amino acid 33, which is roughly the same distance from the amino terminus as the destruction box of mitotic cyclins. The central portion of geminin contains a 35 amino acid sequence from positions 117 to 152 which is predicted to form a coiled-coil domain with five heptad repeats. This is a potential site for protein-protein interactions. There are clusters of basic amino acids between positions 50 and 115. These may serve as a nuclear localization signal or as sites of ubiquitin attachment.

Both human and mouse homologues of geminin can be found in the EST databases. However, there is no obvious homologous sequence in the genome of the budding yeast Saccharomyces cerevesiae. The amino acid sequences of Xenopus geminins H and L, mouse geminin, and human geminin are aligned in FIG. 1. Overall, the human and mouse proteins are about 45% identical to the Xenopus proteins. The amino acids around the destruction box and the coiled-coil region are more highly conserved (89% and 81% identical) than the amino acids outside these regions. The evolutionary conservation of these sequence motifs suggests they are important for the protein's biological function.

The experiments in this paper were performed using the cDNA for geminin H, unless otherwise noted. Whenever geminin H and geminin L were compared, they were found to have identical characteristics.

Geminin is Mitotically Degraded

Xenopus egg extracts were used to demonstrate the mitosis-specific degradation of geminin (FIG. 2A). These extracts reproduce in vitro the substrate specificity and cell cycle control of APC activity. B-type cyclins are degraded by mitotic extract but not by interphase extract, and the degradation requires an intact destruction box in the substrate.

Geminin cDNA was transcribed and translated in vitro in the presence of [$^{35}$S]-methionine. The radioactive protein was then mixed with either interphase or mitotic extract egg extract. At various times, an aliquot of the reaction mixture was removed and the amount of geminin remaining was determined by electrophoresis and quantitative autoradiography. The protein was stable in interphase extract with a half life greater than 90 min (FIG. 2A, top right). In mitotic extract, the protein was unstable and disappeared with a half life of 15 min (FIG. 2A, top middle). Geminin H, geminin L, and cyclin B1 were mitotically degraded with similar kinetics.

When the autoradiogram was overexposed, a ladder of high molecular weight bands was detected above the geminin parent band (FIG. 2A, bottom). The ladder appeared when geminin was incubated in mitotic extract but not in interphase extract. The bands in the ladder represent geminin conjugated to different numbers of ubiquitin residues. If the extract is supplemented with hexahistidine tagged ubiquitin, the bands in the ladder acquire the ability to bind to nickel-agarose beads. These characteristics of the ladder strongly suggest that geminin is destroyed by ubiquitin dependent proteolysis.

To confirm that the degradation occurred via the APC pathway, the degradation reaction was repeated in the presence of an unlabeled peptide containing the cyclin B destruction box (FIG. 2A, third panel). This peptide is ubiquitinated by APC and inhibits the proteolysis of proteins destroyed by the APC pathway, presumably by a competitive mechanism. The presence of the cyclin B destruction box peptide inhibited the formation of geminin-ubiquitin conjugates and stabilized the protein in mitotic extracts.

Geminin Contains a Destruction Sequence

In order to see if the RRTLKVIQP (SEQ ID NO.: 33) sequence constituted a destruction signal, a series of amino and carboxy terminal deletion mutants of geminin was constructed. FIG. 2B shows the portion of the coding sequence remaining in each mutant. The positions of the putative destruction box (amino acids 33 to 41) and the coiled-coil region (amino acids 114–155) are indicated by the small and large rectangles, respectively. The half life of each mutant protein was measured in interphase and mitotic extract. All the proteins were stable in interphase extract, with half lives greater than 90 min. In mitotic extracts, almost all the mutants with an intact RRTLKVIQP (SEQ ID NO.: 33) sequence were degraded normally, with half lives of 10–20 min. The only exception was mutant C140, which may adopt a conformation where the destruction box is inaccessible. For every mutant in which the RRTLKVIQP (SEQ ID NO.: 33) sequence was deleted, the protein was stable, with a half life of >90 min. To confirm this result, a small deletion mutant was constructed in which only these nine amino acids were removed (DEL). This protein was completely stable in mitotic extracts. Finally, a point mutation was constructed in which the leucine at position 36 was changed to alanine (L36A). A cyclin B1 mutant which carries the corresponding mutation is completely stable in mitotic extracts. The gemininL36A mutant protein was also stable. These results indicate that the RRTLKVIQP (SEQ ID NO.: 33) sequence is a required determinant for the destruction of geminin.

Geminin is Ubiquitinated and Degraded by the APC Pathway

A reconstituted reaction system was used to demonstrate that geminin was directly ubiquitinated by APC. The reaction requires mitotic APC, ubiquitin, the E1 and E2 enzymes, and ATP. Enzymatically active APC can be immunoprecipitated from extracts with an antibody directed against one of its subunits, the CDC27 protein. APC which has been immunoprecipitated from mitotic egg extracts is much more enzymatically active than APC immunoprecipitated form interphase extracts.

Figure 2C:
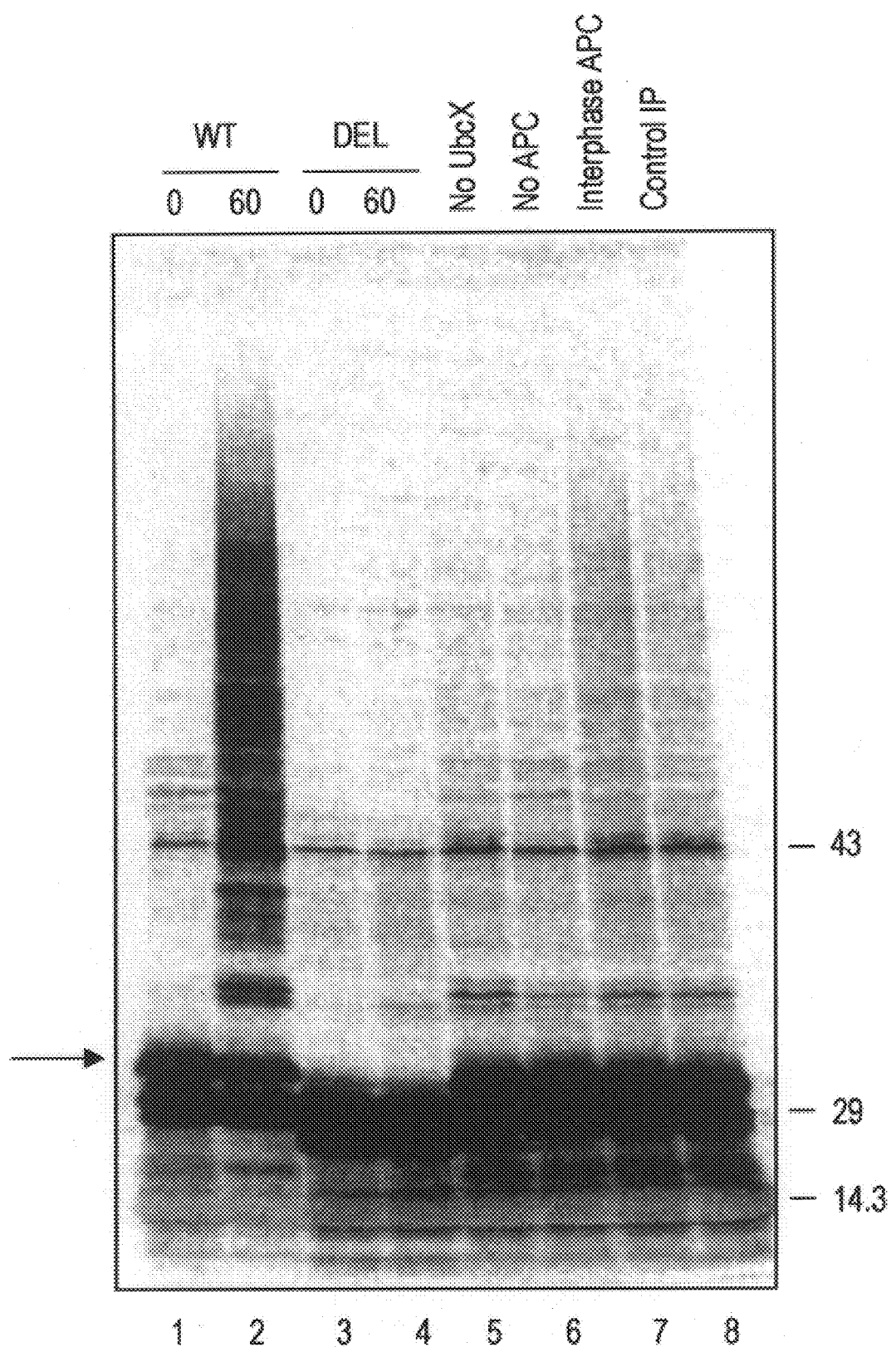

[$^{35}$S]-methionine labeled geminin was prepared by translation in reticulocyte lysate and incubated in a reaction mixture containing all the required components (FIG. 2C). After electrophoresis and autoradiography, a characteristic ladder of ubiquitin conjugates appeared above the starting material (compare lanes 1 and 2). The ladder did not appear if the destruction box mutant geminin$^{DEL}$ was used as the substrate (lanes 3 and 4); if either UbcX or APC was omitted (lanes 5 and 6); if the APC was immunoprecipitated from interphase extracts (lane 7); or if control serum was substituted for the anti-cdc27 serum (lane 8). These results indicate that ubiquitin activating enzyme (E1), ubiquitin conjugating enzyme (E2), and mitotic APC (E3) are sufficient to ubiquitinate geminin in vitro, and that the reaction requires an intact destruction box in the substrate.

Geminin is a Nuclear Protein

To determine the subcellular localization of geminin, polyclonal antibodies were raised against bacterially expressed geminin H and affinity purified. On immunoblots, the antibodies recognize both geminin H and geminin L that have been translated in vitro (FIG. 3A, lanes 1 and 2). The antibodies precipitate two proteins from Xenopus egg extract (lane 3). The band with the higher molecular weight co-migrates with both geminin H and geminin L. The band with the lower molecular weight has the same peptide map as geminin H and geminin L. It may represent a third geminin gene, or a modified form of geminin H or geminin L. In some extracts, the lower band is resolved as two bands (lane 6). On immunoblots of crude egg extract, the antibodies detect four proteins that range in molecular weight from 33 to 40 kD (lane 4). The two lower bands co-migrate with the immunoprecipitated bands. The two higher bands have different peptide maps than geminin H and geminin L; they represent cross-reacting proteins unrelated to geminin. Only the three immunoprecipitated proteins are degraded when APC is activated by adding calcium to unfertilized egg extracts. Quantitative immunoblotting showed that the total geminin concentration varied between 1 and 20 nM in different extracts. The anti-geminin antibodies detect a protein in human HeLa cells that is slightly smaller than the Xenopus geminins, as predicted from the amino acid sequence (lane 7 and FIG. 1). This band is not detected using pre-immune serum (not shown).

Figure 3B:
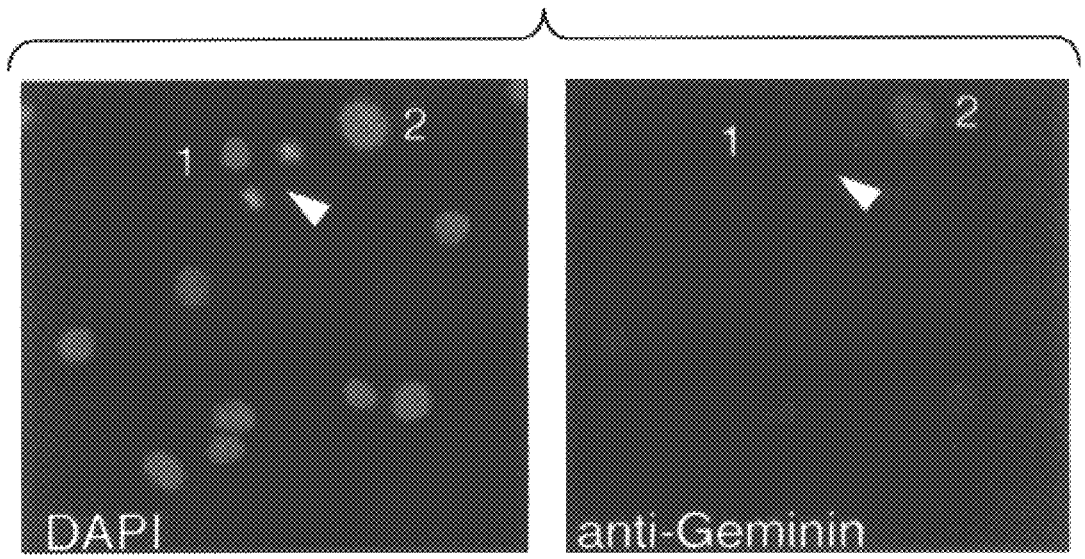

These antibodies were used to perform immunofluorescence staining of cultured Xenopus XL177 cells (FIG. 3B). The nuclear DNA was counterstained with DAPI. Geminin was predominantly localized to the nucleus. An identical staining pattern was seen in HeLa and 293 cells. To exclude the possibility that the signal was coming from the two cross reacting proteins, geminin H was myc-tagged at the amino terminus and transfected into hamster (BHK) cells. Using an antibody raised against the myc epitope, the transfected geminin protein was localized predominantly to the nucleus.

Geminin is Degraded In vivo at the Metaphase/Anaphase Transition

In the immunofluorescence studies, two observations suggested that geminin was being degraded by APC in vivo as the cells progressed through the cell cycle. First, anaphase cells did not stain for geminin (FIG. 3B, arrowhead), suggesting that endogenous geminin is degraded at the metaphase to anaphase transition when APC is activated. Second, it was noticed that the interphase nuclei did not stain uniformly; some stained brightly while others stained very weakly (FIG. 3B, compare 1 and 2). APC activity persists throughout G1 phase and is switched off at the G1/S transition. The weakly staining nuclei could be in G1 phase, when active APC would destroy geminin. The brightly staining nuclei could be in S or G2 phase, when APC is inactive, allowing geminin to accumulate.

Figure 3C:
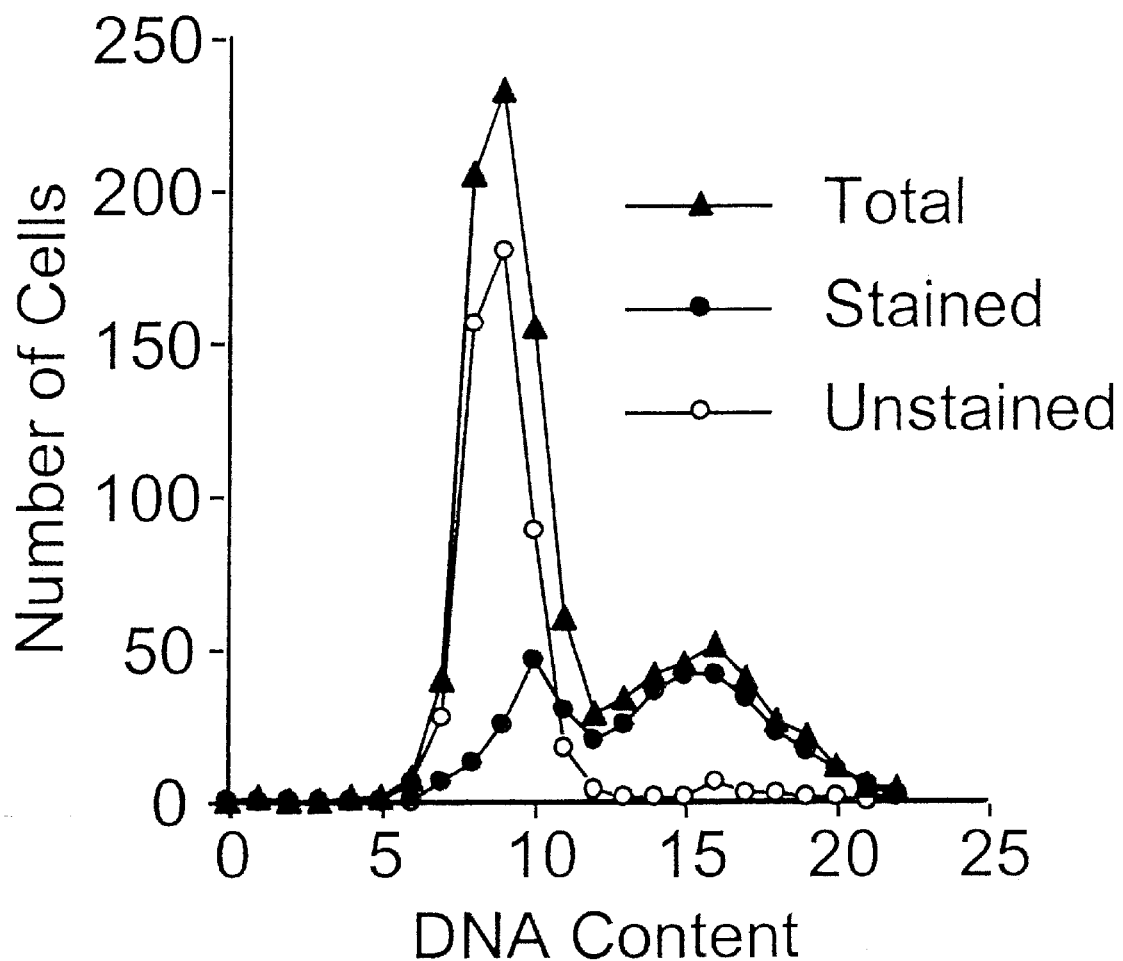

To confirm this hypothesis, XL177 cells in several microscopic fields were digitally photographed and blindly classified as either brightly staining or weakly staining for geminin. Then the nuclear DNA content of the cells in each population was quantitated by measuring the intensity of the DAPI fluorescence. FIG. 3C shows a histogram of DNA content in each of the two populations and for the total population. The total population shows a typical bimodal distribution of DNA content (triangles). The two peaks represent G1 and G2 cells respectively (2n and 4n DNA content), and the area in between represents cells in S phase. Virtually all the weakly staining cells had a G1 DNA content (open circles), while the vast majority of brightly staining cells had a G2 DNA content (closed circles). The cells with an intermediate DNA content also stained for geminin. These results suggested that geminin was absent from cells during G1, accumulated during S and G2 phases, and then was destroyed before G1 phase of the next cell cycle.

Figure 3D:
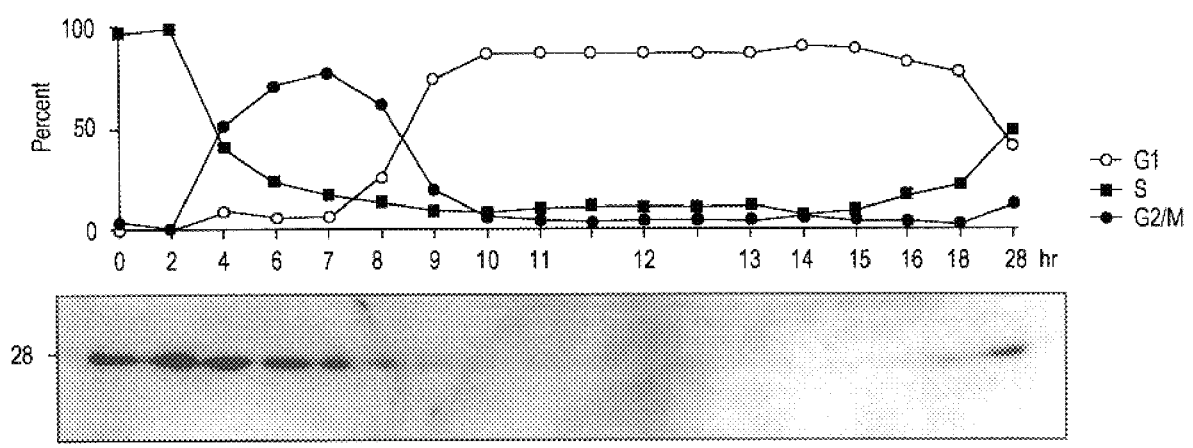
Figure 4A:
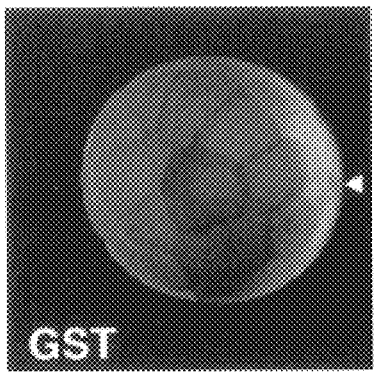
FIGS. 4A–D show that undegradable Geminin inhibits nuclear duplication.
Figure 4B:
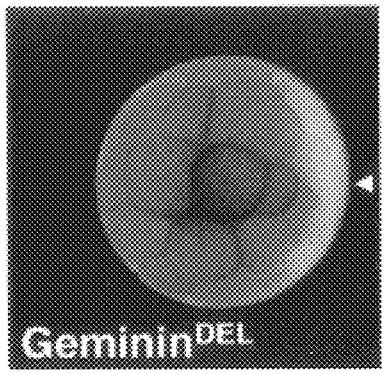
Figure 4C:
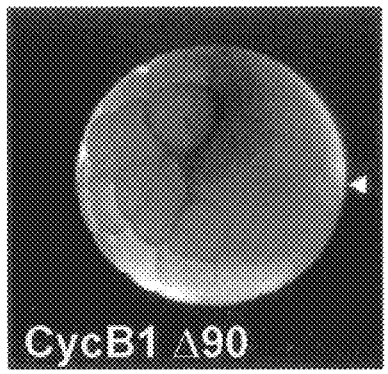
Figure 4D:
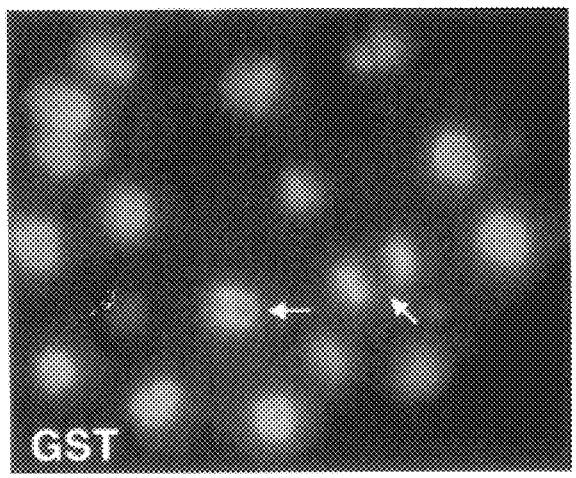
Figure 4E:
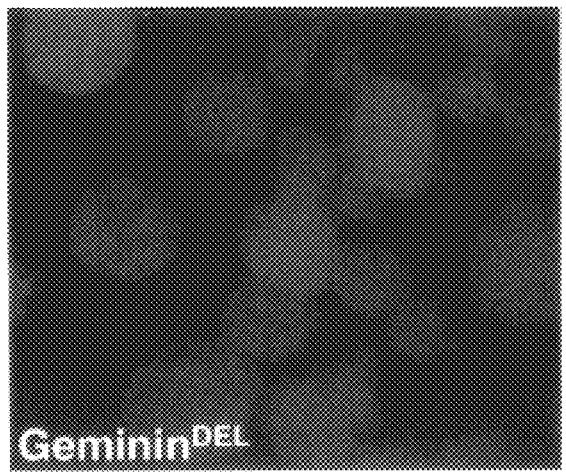

These results were confirmed using synchronized cells. Because of the technical difficulty of synchronizing Xenopus cultured cells, HeLa cells were used instead. The cells were arrested at the beginning of S phase with a double-thymidine block then released. At various times after release, the geminin level was measured by immunoblotting and the cell cycle stage was determined by FACS analysis (FIG. 3D). The FACS data indicate that the cells completed S phase 2–6 hours after release, and exited from mitosis 7–9 hours after release. The immunoblot shows that the geminin concentration was high throughout S phase, G2 phase, and most of M phase. The amount of geminin abruptly declined at the time when the cells exited from mitosis and remained low during the following G1 phase. After 18–28 hours, the cells began to re-enter S phase and geminin re-accumulated. This is the pattern expected for a protein ubiquitinated and degraded by the APC pathway.

Geminin Inhibits Nuclear Duplication

To determine the biological function of geminin, one of the stable mutants, geminin$^{DEL}$, was fused to a six-histidine tag, expressed in bacterial cells, and purified to >90% homogeneity (not shown). This protein is stable in mitotic cell extracts because all nine amino acids in the destruction box have been deleted (FIG. 2B). The mutation does not seem to inhibit biological activity (see FIGS. 4 and 5A, below). As a control, GST protein was expressed and purified in the same way. The effect of these purified proteins on cell cycling was determined both in vivo and in vitro.

Either the GST protein or the mutant geminin$^{DEL}$ protein was injected into one cell of a Xenopus egg that had divided once (FIG. 4, top). In both cases, cleavage progressed normally in the injected half of the embryo. Similar results were obtained if the same concentration of wild-type geminin was injected (not shown). By contrast, injection of undegradable cyclin B_90 arrested cleavage on the injected side. The fact that the geminin$^{DEL}$-injected eggs continued cleaving indicates that the protein does not affect either the process of cytokinesis or the sequential activation and inactivation of the p34cdc$^2$/cyclin B kinase. This result was confirmed biochemically by measuring histone H1 kinase activity in a cycling egg extract.

Although the geminin$^{DEL}$ injected embryos continued cleavage, they did not develop normally. They arrested at the blastula stage and never went on to gastrulate. To investigate the cause of this arrest, the blastulae were sectioned and the DNA was stained with Hoechst dye (FIG. 4, bottom). The embryos were found to have a very striking and obvious defect; the cells produced by cleavage were completely anucleate. Embryos injected with either the same concentration of wild-type geminin or lower concentrations of undegradable geminin$^{DEL}$ had small, misshapen nuclei (not shown). By contrast, embryos injected with the GST protein had normal appearing nuclei in both the interphase and the mitotic configuration (FIG. 4, bottom), and developed normally into tadpoles (not shown).

Geminin Inhibits Nuclear DNA Replication

The injection experiments suggested that the undegradable form of geminin specifically interfered with some step in nuclear duplication. All of these steps can be reproduced in vitro using demembranated sperm and extracts made from Xenopus eggs. We could not demonstrate any effect of geminin$^{DEL}$ on nuclear assembly, spindle assembly, or chromatid separation.

Figure 5A:
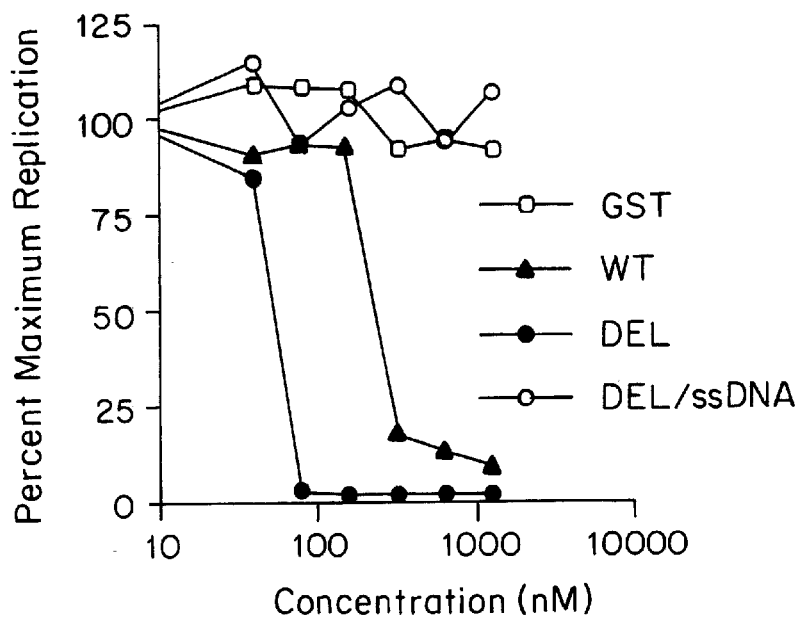
FIG. 5A shows that replication of a sperm head DNA was measured in the presence of GST (open squares), Geminin$^{WT}$ (closed triangles), or undegradable Geminin$^{DEL}$ (closed circles) at various concentrations. Replication of single stranded M13 mp18 DNA was also measured in the presence of Geminin$^{DEL}$ (open circles).
Figure 5B:
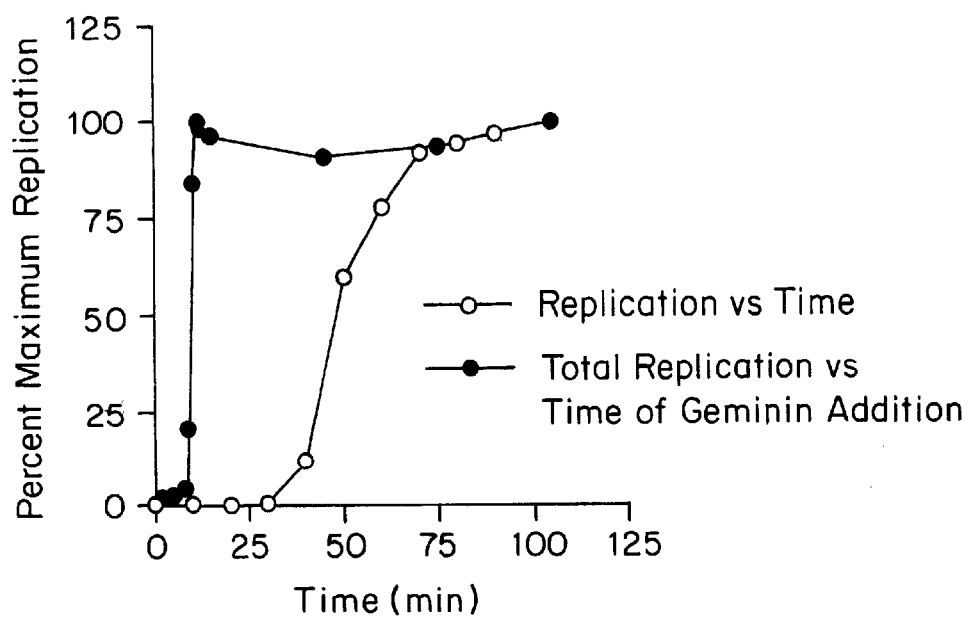
FIG. 5B shows that Geminin inhibits initiation. Closed Circles: A DNA replication reaction was started by adding calcium. At various times after calcium addition, undegradable Geminin$^{DEL}$ was added to an aliquot. The reaction was allowed to proceed for 3 hours, and the total amount of replication was plotted against the time of Geminin addition. Open Circles: To determine the time when nucleotide incorporation occurred, a separate reaction was done without Geminin addition. An aliquot was removed at various times after activation and the amount of replication was measured.

However, geminin strongly inhibited DNA replication. Xenopus egg extracts contain all the components needed to replicate sperm DNA. Replication begins about 30 minutes after an unfertilized egg extract is activated with calcium and continues until all the chromatin has been replicated exactly once (FIG. 5B, open circles). In the presence of either geminin$^{WT}$ or undegradable geminin$^{DEL}$, there was a profound inhibition of DNA replication (FIG. 5A). Very low concentrations of undegradable geminin$^{DEL}$ protein (20–80 nM) were sufficient to bring about virtually complete inhibition. The exact concentration required to inhibit replication varied from extract to extract. Degradable geminin$^{WT}$ protein was not as potent as geminin$^{DEL}$ at inhibiting replication (FIG. 5A, triangles); higher concentrations (300 nM) were needed to produce the same level of inhibition. This difference can be explained by the fact that calcium addition causes a transient burst of APC activity. A sizable fraction of the exogenously added geminin$^{WT}$ protein was degraded after calcium addition, but not the geminin$^{DEL}$ protein. Wild type geminin H and geminin L were equally potent for inhibiting replication. GST protein had no inhibitory effect (FIG. 5A, open squares).

In order to map the minimal replication inhibitory domain of the geminin H protein, each of the mutants shown in FIG. 2B was bacterially expressed and its effects on the replication reaction was tested. Deletion of up to 80 amino acids from the amino terminal or 60 amino acids from the carboxy terminal did not affect the protein's ability to inhibit replication (FIG. 2B). Larger deletions from either end completely destroyed the protein's inhibitory activity. The replication inhibition domain of the protein lies between amino acids 80 and 160, a region which includes the predicted coiled-coil domain. A myc-tagged fragment of geminin L consisting only of amino acids 87–168 (L 87–168) was sufficient to inhibit replication, confirming this result.

Replication Occurs Normally when Geminin is Immunodepleted

Figure 5C:
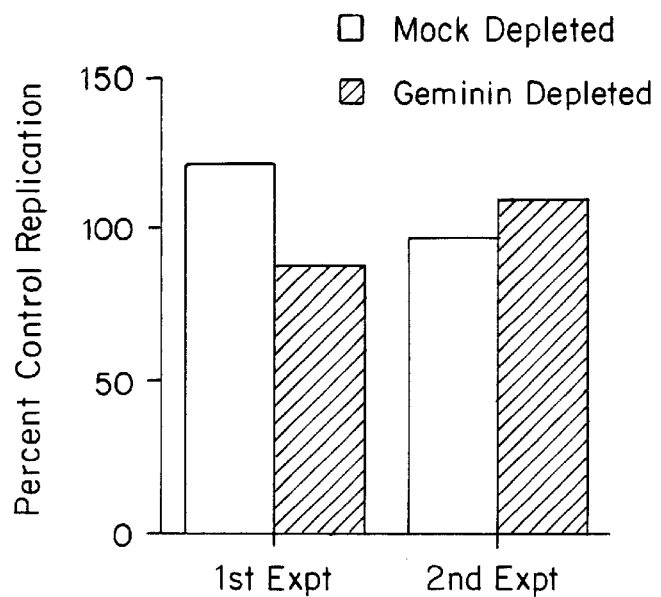
FIG. 5C shows that replication occurs normally when Geminin is immunodepleted. In two separate experiments, CSF-arrested extracts were treated with either rabbit IgG or anti-Geminin antibody (see FIG. 3A, right). Demembranated sperm were added to the supernates and DNA replication was measured.

The anti-geminin antibodies were used to immunodeplete geminin from a replication extract and the effects on replication were measured. Immunoblotting showed that >99% of the endogenous geminin could be removed by immunodepletion (FIG. 3A, compare lanes 9 and 10). When the endogenous geminin was removed, replication proceeded to the same extent as in control extracts (FIG. 5C). Immunodepletion of geminin affected neither the exit from mitosis induced by calcium nor the entry into mitosis induced by cyclin B Δ90.

Figure 5D:
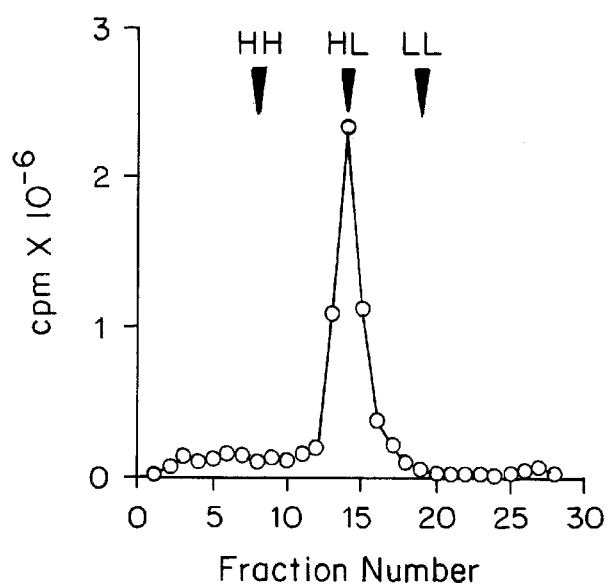
FIG. 5D illustrates that a single round of replication occurs in the absence of Geminin. Replication was allowed to proceed to completion in a Geminin-depleted extract in the presence of BrdUTP and α-[$^{32}$P]-dATP. The density of the labeled newly replicated DNA was determined by equilibrium centrifugation on a CsCl gradient. The arrowheads indicate the positions of light-light carrier DNA (LL); heavy-light DNA produced by a control reaction (HL); and the predicted position of heavy-heavy DNA (HH).

One possible biological function of geminin would be to inhibit a second round of replication during S, G2, or M phase. To investigate this possibility, density label substitution experiments were performed with geminin-depleted extracts supplemented with BrdUTP (FIG. 5D). Replication was allowed to proceed to completion, then the density of the product DNA was determined by equilibrium centrifugation in a cesium chloride gradient. All of the DNA had a heavy-light density, demonstrating that it had replicated only, once. In Xenopus egg extracts, the absence of geminin is not sufficient to cause an extra round of DNA replication (see Discussion).

Geminin Inhibits Initiation

Two separate experiments showed that geminin inhibits the initiation of DNA synthesis, but not elongation or ongoing DNA synthesis. First, we found that geminin$^{DEL}$ had no effect on DNA synthesis from a single stranded bacteriophage M13 DNA template (FIG. 5A, open circles). In Xenopus extracts, replication from single stranded templates does not depend on initiation factors and is thought to reflect elongation synthesis only.

Second, there was a narrow time window during which the replication process was sensitive to geminin. This time window was over long before DNA polymerization began. To demonstrate this sensitive period, a standard replication reaction was started by calcium addition, and stable geminin$^{DEL}$ was added at various times afterwards. The reaction was allowed to proceed to completion and the total extent of replication was determined (FIG. 5B, filled circles). If the protein was added within 10 minutes of calcium addition, replication was completely inhibited. But if the protein was added at later times, replication proceeded normally. The sensitive period could be compared to the time at which replication began by measuring the amount of α-[$^{32}$P]-dATP incorporated at various times during a reaction without added geminin (FIG. 5B, open circles). Replication did not begin until about 30 minutes after calcium addition, or about 20 minutes after the sensitive period had passed. These results suggested that a very early step in the replication process is sensitive to geminin, and that elongation synthesis is not affected.

Geminin Inhibits the Formation of Pre-Replication Complex

Many proteins required for DNA replication are thought to form a pre-replication complex (pre-RC) at replication origins. The pre-RC includes the proteins of origin recognition complex (ORC), cdc6, and a complex of minichromosome maintenance (MCM) proteins. The pre-RC is assembled sequentially. ORC remains directly bound to origins of DNA replication throughout the cell cycle. Shortly before replication begins, first cdc6 and then the MCM complex associate with chromatin. After initiation has occurred, cdc6 and MCM complex are released.

Figure 6A:
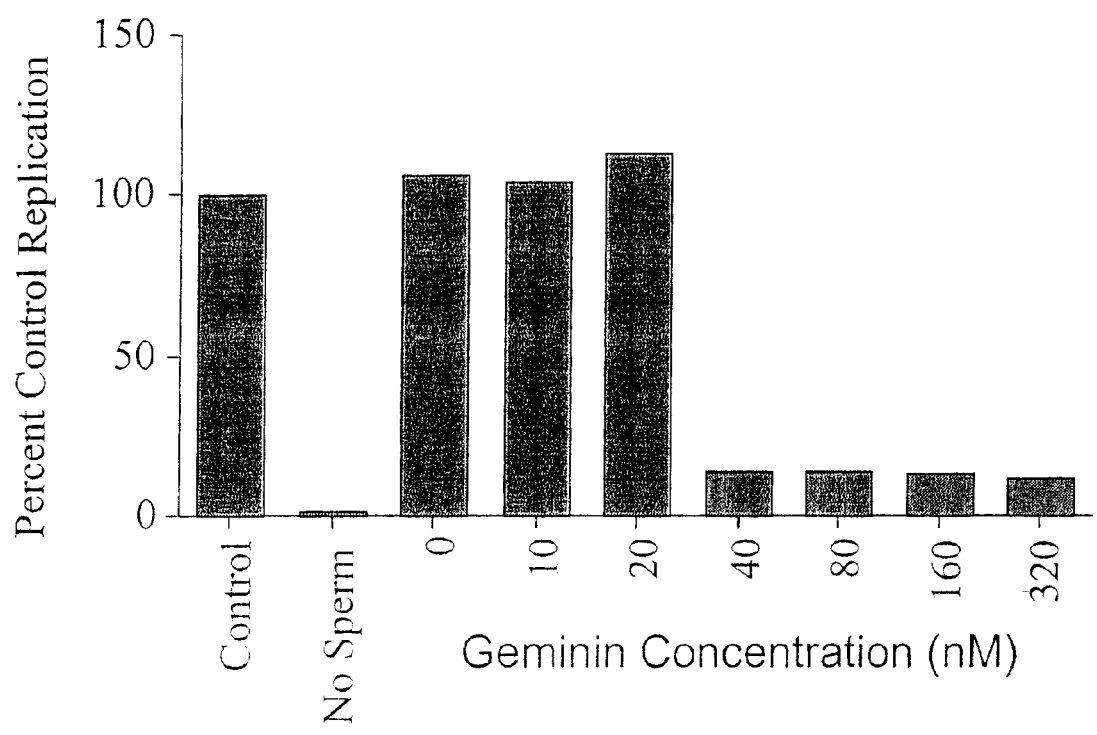
FIGS. 6A–B show that Geminin disrupts the assembly of pre-replication complex.
Figure 6B:
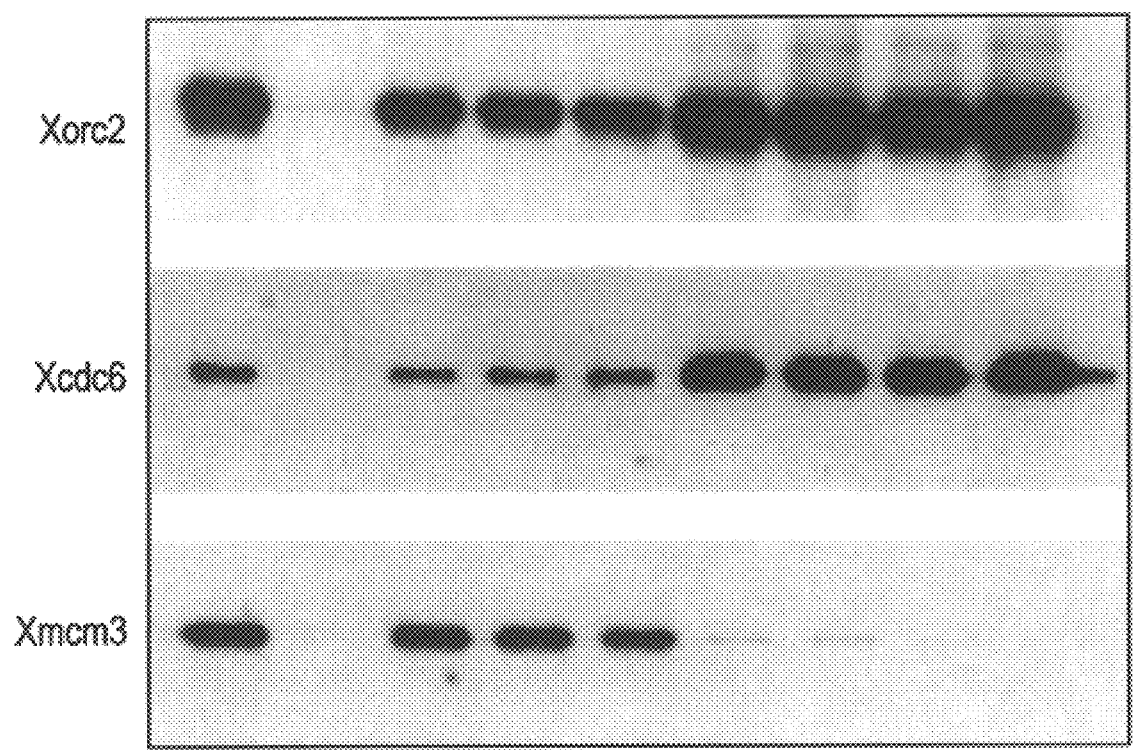

The assembly of the pre-RC can be reconstituted in vitro using Xenopus egg extracts and demembranated sperm. After a brief period of assembly, chromatin is pelleted and the proteins bound to the chromatin are identified by immunoblotting. To see if geminin interfered with the assembly of the pre-RC, different concentrations of the geminin 1L protein were added to these reactions. FIG. 6B shows that the binding of the MCM complex to chromatin is strongly inhibited by geminin. To compare the concentration needed to inhibit binding and the concentration needed to inhibit replication, standard replication assays were performed using the same extract. Inhibition of MCM binding occurred at the same concentration that inhibited DNA replication (FIG. 6A). By contrast, the binding of the ORC complex to chromatin was not affected by geminin. The binding of Xcdc6 was markedly enhanced by geminin (FIG. 6B). Xcdc6 dissociates from chromatin after the MCM complex is bound. Geminin seems to arrest the replication reaction before MCM complex binds and before Xcdc6 dissociates, so that more of the Xcdc6 protein is found bound to chromatin.

Discussion

In this paper we describe a new protein, geminin, which has two important properties related to the cell cycle. First, it is specifically degraded at the time of the metaphase to anaphase transition. Second, it inhibits the initiation of DNA replication. These two properties are associated with two separate domains of the protein. The mitotic degradation depends on a 9 amino acid destruction box sequence located near the amino terminus. The replication inhibition activity resides in an 80 amino acid region that includes a sequence that is predicted to form a coiled-coil structure. The developmental effects of geminin are mediated by a third separate domain (amino acids 40–90) through an unknown mechanism.

Geminin is Degraded at the Time of Exit from Mitosis

Geminin appears to be ubiquitinated and degraded by the APC pathway which degrades B-type cyclins. Several pieces of evidence support this conclusion. Geminin contains a destruction box sequence near its amino terminus which is recognized by mitotic APC. If this sequence is mutated or deleted, the protein becomes stable in mitotic cell extracts. Geminin is ubiquitinated by purified anaphase promoting complex (APC) in vitro. This reaction requires an intact destruction box and is carried out efficiently by the mitotic form of APC but not by the interphase form.

Geminin levels fluctuate in cultured cells in the pattern predicted for a protein ubiquitinated by APC. The protein is absent from G1 cells, when APC is active. When APC is turned off at the G1/S transition, geminin accumulates and persists throughout S phase, G2 phase, and most of M phase. Finally, when APC is activated at the metaphase/anaphase transition, geminin levels decline precipitously and remain low throughout G1 phase. In our experiments with synchronized HeLa cells, high concentrations of geminin were present at the arrest point, which was early in S-phase. Geminin probably accumulated during the period of arrest, since at the arrest point the cells would have passed the G1/S transition.

Geminin Inhibits DNA Replication

Low concentrations of bacterially expressed geminin profoundly inhibit nuclear DNA replication. We can demonstrate this effect in vivo, by injecting geminin into embryos, and in vitro, by adding geminin to a DNA replication extract. The protein inhibits replication at extremely low concentrations (20–80 nM). This is comparable to the concentration at which p21 inhibits replication in Xenopus extracts (200 nM) or the physiological concentration of known replication proteins like Xcdc6 (80 nM) or Xorc2 (100 nM). The bacterially expressed geminin seems less potent than the native protein, since the endogenous geminin concentration in eggs is 1–20 nM. Because geminin is a nuclear protein, the effective concentration at the site of DNA replication may be much higher.

Several pieces of evidence suggest that that the endogenous geminin protein inhibits replication under physiological conditions. First, replication occurs normally when the protein is immunodepleted from extracts. Second, when bacterially expressed geminin is added to a concentration sufficient to inhibit replication and then removed by immunodepletion, replication is normal. These results indicate that the bacterially expressed protein is not acting in a dominant negative manner by binding and sequestering an essential replication component. Finally, when synthetic geminin RNA is translated in Xenopus extracts, the protein produced inhibits replication. This excludes the possibility that the bacterially expressed protein has an activity that the endogenous protein lacks due to a difference in modification.

At a molecular level, geminin arrests the sequential assembly of pre-replication complex (pre-RC) on DNA at origins of replication. The incorporation of MCM complex into pre-RC is strongly inhibited by geminin, while the incorporation of Xcdc6 is enhanced. The arrest in pre-RC assembly occurs between the binding of Xcdc6 and the binding of MCM complex. Xcdc6 is thought to bind to chromatin and assist the recruitment of MCM complex, after which it is released. Our results suggest that if the binding of MCM complex is inhibited, Xcdc6 release does not occur. The MCM complex binds to chromatin 15–30 minutes after a replication reaction is started, and geminin is able to inhibit replication during the first 10–15 minutes of the reaction (FIG. 5B). This temporal correspondence suggests that the effect of geminin on the binding of MCM complex is rather direct. Apparently geminin does not cause release of MCM complex which is already bound to chromatin.

The exact biochemical mechanism by which geminin inhibits MCM binding is unknown. An 80 amino acid domain of geminin is sufficient to inhibit replication in vitro. Part of this domain is predicted to form a coiled-coil structure, suggesting that it is a site of protein-protein interactions. The simplest model is that geminin binds to and sequesters MCM complex or some other component of pre-RC and prohibits it from participating in complex formation. In preliminary experiments, we have been unable to co-immunoprecipitate geminin with either Xorc2, Xcdc6, or Xmcm3. DNA replication also depends on the activity of certain cyclin-dependent kinases. Some kinases such as Cdk2/cyclin E are required for DNA replication, while others such as cdc2/cyclin B inhibit the process. Geminin may affect the activity of one or more of these kinases. In preliminary experiments, geminin has no measurable effect on immunoprecipitated Cdc2, Cdk2, or cyclin E-associated kinase activity.

Model for Geminin's Role in Cell Cycle Control

Figure 7:
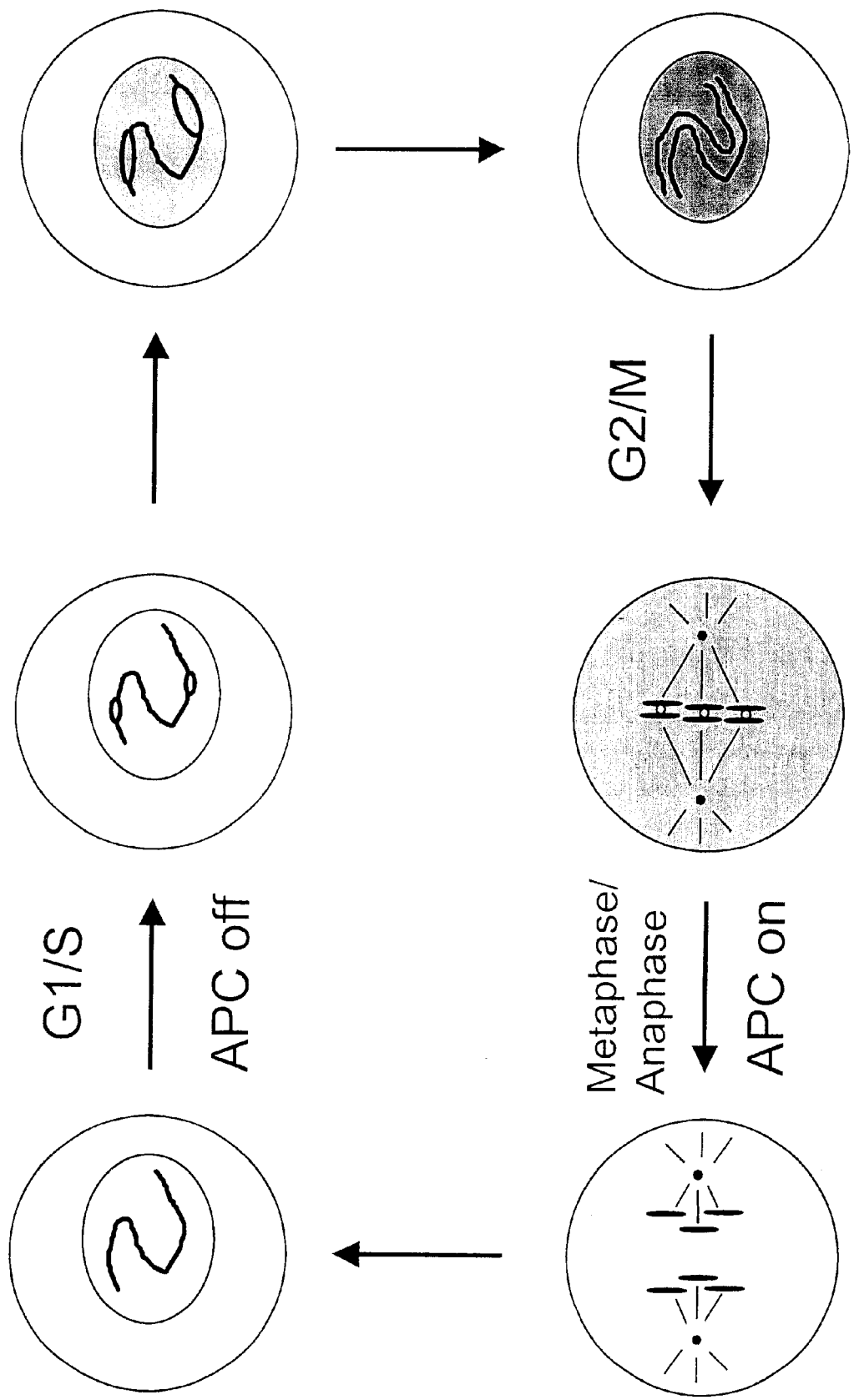
FIG. 7 shows a model for the control of DNA replication Geminin. During G1 phase (upper left), Geminin levels are low, but slowly accumulate as the Geminin Gene is transcribed and translated. APC is inactive. At the G1/S transition, APC is inactive and Geminin continues to accumulate (gray shading). After a certain point, enough Geminin has accumulated to prohibit further initiation during either late S, G2, or M phase. At the metaphase/anaphase transition, APC activity is restored and Geminin is degraded, allowing DNA replication to proceed in the next cell cycle.

We present the following model for the biological activity of geminin in cell cycle control (FIG. 7). We propose that the function of geminin is to prohibit the initiation of DNA replication at inappropriate times during the cell cycle. The level of geminin protein is controlled primarily by the activity of APC, though there may be additional transcriptional or post-transcriptional mechanisms. During G1 phase, when APC is active, the geminin concentration is too low to inhibit replication. At the G1/S transition, APC is inactivated and geminin begins to accumulate. Initially, the geminin concentration is insufficient to inhibit pre-RC assembly, and DNA replication begins. As S phase progresses, enough geminin accumulates to prevent further assembly of pre-RC. Because geminin has no effect on elongation, DNA replication continues to completion. The protein continues to inhibit replication throughout the remainder of S phase, G2 phase, and most of M phase. At the metaphase/anaphase transition, APC is activated and geminin is abruptly degraded. The degradation of geminin permits another round of replication to begin in the next cell cycle.

The classic cell fusion experiments of Rao and Johnson demonstrated the existence of a mechanism that prevents replication after S phase. They showed that when a G1 phase cell and an S phase cell are fused, the G1 nucleus replicates prematurely. This implies that the cytoplasm of the S phase cell contains an activator of replication and that the G1 nucleus is capable of responding to it. However, when a G2 phase cell and an S phase cell are fused, the G2 nucleus does not replicate. Apparently, a G2 nucleus cannot respond to the S-phase replication signals. Passage through mitosis must restore the ability of the nucleus to replicate in the next cell cycle. Several models have been proposed to explain the failure of G2 nuclei to undergo replication.

One model proposes that G2 nuclei lack an essential replication component called licensing factor. Licensing factor is postulated to be present in G1 nuclei and consumed during the replication process. When the nuclear envelope breaks down during mitosis, the nuclear store of licensing factor is replenished from cytoplasmic stores, allowing DNA replication in the next cell cycle. The licensing model is supported by the observation that permeabilization of a G2 nucleus with detergents allows a second round of replication in Xenopus extracts. A protein complex that exhibits many of the expected characteristics of licensing factor has been partially purified.

Other models propose that G2 nuclei contain an inhibitor of replication which is destroyed at the time of exit from mitosis. Previous work in yeast has strongly implicated mitotic CDKs as inhibitors of replication during late S and G2 phase. In budding yeast, cdc28/clb kinase inhibits replication by inhibiting the activity of cdc6. Transient inhibition of this kinase allows a second round of replication. In fission yeast, reduction of cdc2/cdc13 kinase activity by a variety of means results in repeated rounds of replication. Other types of inhibitors may inhibit G2 replication in vertebrate cells. For example, the ts41 mutant hamster cell line undergoes multiple rounds of replication without mitosis at the non-permissive temperature. The mutation is proposed to inactivate a protein that inhibits replication and promotes mitosis. Another activity that inhibits replication has been identified in extracts from unfertilized Xenopus eggs. This activity is lost at the time of fertilization.

The properties of geminin exactly match the expected characteristics of a G2 replication inhibitor: the protein is present in G2 nuclei but not G1 nuclei, inhibits DNA replication, and is localized to the nucleus. Cell fusion experiments indicate that any proposed inhibitor must be confined to the G2 nucleus, because when G2 and S phase cells are fused, the S phase nucleus replicates DNA normally. However, the absence of geminin is not sufficient to allow a second round of replication in Xenopus extracts (FIG. 5D).

The model outlined in FIG. 7 does not exclude the possibility of either positively acting licensing factors or additional G2 replication inhibitors. Because even a small amount of excessive replication would have catastrophic long term consequences, cells may have evolved several mechanisms that operate in parallel or in series to ensure that re-initiation does not occur. Re-replication may be prevented by different mechanisms during different phases of the cell cycle or in different types of cells. A geminin-dependent mechanism may not operate in budding yeast, since they lack a homologous protein. This suggests that the mechanisms that restrict replication may be different in different organisms.

Example 2

Geminin, a Neuralizing Molecule that Demarcates the Future Neural Plate at the Onset of Gastrulation In an expression cloning screen in Xenopus embryos, we identified a gene that when overexpressed expanded the neural plate at the expense of adjacent neural crest and epidermis. This gene, which we named geminin, had no sequence similarity to known gene families. We later discovered that geminin's neuralizing domain was part of a bifunctional protein whose C-terminal coiled-coil domain may play a role in regulating DNA replication. We report here on the neuralizing function of geminin. The localization, effect of misexpression, and activity of a dominant negative geminin suggest that this gene product has an essential early role in specifying neural cell fate in vertebrates. Maternal geminin mRNA is found throughout the animal hemisphere from oocyte through late blastula. At the early gastrula, however, expression is restricted to a dorsal ectodermal territory that prefigures the neural plate. Misexpression of geminin in gastrula ectoderm suppresses BMP4 expression and converts prospective epidermis into neural tissue. In ectodermal explants, geminin induces expression of the early proneural gene neurogenin-related 1 although not itself being induced by that gene. Later, embryos expressing geminin have an expanded dorsal neural territory and ventral ectoderm is converted to neurons. A putative dominant negative geminin lacking the neuralizing domain suppresses neural differentiation and, when misexpressed dorsally, produces islands of epidermal gene expression within the neurectodermal territory, effects that are rescued by coexpression of the full length molecule. Taken together, these data indicate that geminin plays an early role in establishing a neural domain during gastrulation.

The phenomenon of neural induction was discovered in 1924 when dorsal mesoderm from an early gastrula stage amphibian embryo was shown to induce a secondary body axis and nervous system after transplantation to the ventral side of another early gastrula embryo (Spemann and Mangold, 1924). Recently, several key aspects of this phenomenon have been elucidated at the molecular level. Signaling by bone morphogenetic proteins (BMPs) promotes epidermal differentiation and blocks neural differentiation in ectoderm of both vertebrate and invertebrate organisms. Neural induction is now seen as a local suppression of this BMP signaling by factors released by the Spemann organizer in dorsal mesoderm that bind directly to BMPs to inhibit their function (reviewed in Harland, 1997; Sasai and De Robertis, 1997; Weinstein and Hemmati-Brivanlou, 1997). Neuralization pathways can be activated experimentally by disrupting signaling between ectodermal cells (Grunz and Tacke, 1989; Godsave and Slack, 1989), and epidermalization is restored by adding BMP4 protein to the dissociated ectoderm (Wilson and Hemmati, 1995). In vivo, two secreted proteins expressed in gastrula organizer mesoderm, chordin (the vertebrate homologue of the Drosophila gene short gastrulation) and noggin, can directly bind BMPs to prevent receptor binding (Piccolo et al., 1996; Zimmerman et al., 1996). Other neural inducing molecules secreted by organizer cells (Xnr3, follistatin) also appear to act by antagonizing BMP signaling (Hansen et al., 1997; Yamashita et al., 1995; Harland and Gerhart, 1997). As this inhibition of BMP signaling neuralizes ectodermal explants, it is likely to initiate neural induction in vivo.

The cell signaling and transcriptional events occurring between mesodermal signaling and the earliest expression of neural differentiation markers in ectoderm are relatively obscure in vertebrate embryos. In Drosophila, patterning of the neurogenic region responds to a complex range of proneural and neurogenic gene activities, each of which is induced by earlier dorsal-ventral signal transduction cascades and regional specification by homeobox genes. In vertebrates, several transcription factors, most members of the basic helix-loop-helix family, have been identified that can act as proneural genes, converting ventral ectoderm to neural tissue or expanding the size of the neural plate when misexpressed (reviewed in Lee, 1997; Chitnis and Kintner, 1995b). The earliest ectodermal expression of any of these genes in vivo is that of neurogenin related-1 (X-ngnr-1)(Ma et al., 1996), beginning at stage 10.5 along the lateral edges of the presumptive neural tissue plate. Later expression of these genes localizes to stripes of primary neurons, consistent with the likely function of these genes in determination or differentiation of neurons.

We have attempted to identify molecules involved in early inductive events by injecting RNA made from relatively small pools of cDNA clones into early Xenopus embryos and assaying for changes in embryonic morphology. Previous studies of this kind, using cDNAs made from dorsalized gastrulae (Smith and Harland, 1991; Smith and Harland, 1992; Lemaire et al., 1995; Lustig et al., 1996b), have identified more than 10 genes involved in dorsal signaling. Here, an early embryonic library, made from st. 6–7 blastulae, was used in the hope of identifying new early patterning factors. mRNA pools from this library were injected into either ventral or dorsal blastomeres of early Xenopus embryos to identify genes that, when overexpressed, perturbed the embryonic axis. One such activity, which we named geminin (see below) caused expansion of the neural plate.

Geminin RNA and protein are localized to the animal hemisphere during early cleavages. At the early gastrula stage (st. 10– to 10+), geminin becomes restricted to an ectodermal domain that strikingly prefigures the neural plate. Geminin's ability to neuralize ectoderm, its induction by neural inducers, capacity to induce early proneural genes, and the inhibition of neural patterning by a putative dominant negative domain all suggest that geminin plays a key early role in neurogenesis.

While this work was underway, an independent biochemical screen in our laboratory for mitotically-degraded proteins (using a different cDNA library) identified a gene closely related in sequence. Its pattern of expression and functional properties appear to be identical to geminin. The activity of this gene suggests it is an inhibitor of DNA replication. These replication functions have been localized to a domain that is non-overlapping with the neuralizing domain. We have used the name geminin, after gemini meaning twins, to denote these two closely related genes and indicate their functional duality. These data suggest that geminin is a bifunctional protein that at the early gastrula stage marks and establishes neural cell fate in the dorsal ectoderm and that may, in other cellular contexts, also regulate progression through the cell cycle.

Materials and Methods

Library Construction and Expression Cloning

A directional cDNA library was constructed from early blastula (st. 6–7) embryos and cloned into pCS2+ (Turner and Weintraub, 1994). Capped RNA was synthesized from pools of 100–300 clones as described (Krieg and Melton, 1987) and approximately 2 ng of RNA was injected into one dorsal or ventral blastomere of a four cell embryo. Pools affecting embryonic morphology were sib selected as described (Lustig et al., 1996a) to isolate a single active cDNA. Single clones were sequenced on both strands on an automated DNA sequencer.

Xenopus Embryos and Explants

Xenopus embryos were obtained from previously unovulated X. laevis frogs (NASCO) by in vitro fertilization, dejellied, and cultured at 16–18¼C. in 0.1×Marc's Modified Ringer's (MMR) (Peng, 1991) containing 50 micrograms/ml gentamycin. Embryos were staged according to Nieuwkoop and Faber (Nieuwkoop and Faber, 1967). Embryos were injected with plasmids or RNAs in 0.2×Marc's Modified Ringer's (MMR) containing 5% Ficoll and 50 $\mu$g/ml gentamycin and cultured in the same media at 16–18¼C. For animal cap explants, both cells were injected superficially in the animal hemisphere at the 2-cell stage and explants were isolated at stage 8 and cultured in agarose coated dishes containing 0.7×MMR with 50 $\mu$g/ml gentamycin until control embryos at the same temperature reached the desired stage.

Transgenic embryos were generated by restriction enzyme-mediated integration of linearized plasmid DNA into permeabilized sperm nuclei (Kroll and Amaya, 1996) with minor modifications (Kroll and Amaya, in press).

Plasmids and RNAs

Plasmids encoding deletion mutants of geminin were produced by amplifying portions of the open reading frame with low-cycle number PCR using Pfu polymerase (Stratagene) and cloning as an EcoRI to XbaI fragment into pCS2+MT (Turner and Weintraub, 1994). Deletion mutants of geminin described in the text correspond to amino acids 38 to 90 (Ngem), 87 to 168 (Cdim), or 112 to 168 (Ccoil). cDNAs encoding mouse geminin were cloned as above using expressed sequence tags as template. For geminin dominant negative and rescue experiments, plasmids contained the CMV enhancer, promoter, polylinker and polyadenylation signal from pCS2+ and, in inverse orientation directly adjacent to the CMV enhancer, a minimal simian CMV promoter, second polylinker and polyadenylation signal (kindly provided by Robert Davis). Cdim mutant was cloned into each polylinker to create two dominant negative constructs; full-length geminin was then cloned into both Cdim containing plasmids. Cloning of Cdim and full-length fragments into both polylinkers controlled for possible differences in transcription levels from the two promoters, but both dominant negative and both rescue constructs performed similarly. Plasmids were linearized with NotI for transgenesis.

Plasmids for producing capped RNA for BMP4 (Nishimatsu et al., 1992), X-ngnr-1 (Ma et al., 1996) and neuroD (Lee et al., 1995) have been described. To produce noggin (Smith and Harland, 1992) and chordin (Sasai et al., 1994) RNAs, the open reading frames were cloned into CS2+. RNAs were injected at the following doses for animal cap assays: 500 pg BMP4, 50 pg noggin, 250 pg chordin, 150 pg X-ngnr-1, and 500 pg neuroD. For most other experiments, 10–20 pg full length geminin RNA, 50–500 pg Ngem RNA, or 250 pg of pCS2+ plasmid encoding gem was injected into one blastomere at the two-cell stage (see text for more details). For animal cap explants, embryos were injected with half this dose in each cell at the two-cell stage.

In situ Hybridization and Immunostaining

For in situ hybridization (Harland, 1991) we used the modified double in situ hybridization protocol (Knecht et al., 1995). Antisense probe for geminin was produced by T3 transcription from EcoRI digested pCMVgem. In situ hybridization to 7 micron sections of NIH Swiss mouse embryos (Novagen, Madison, Wis.) was performed after Wilkinson (1992) with NBT/BCIP as the alkaline phosphatase substrate. Probe was generated using the entire mouse geminin open reading frame. Myc-tagged geminin protein was detected with the 9E10 anti-myc antibody (Boeringer) and an HRP-conjugated secondary antibody. Endogenous geminin protein in embryos was detected using affinity purified antibody against full-length geminin protein (Babco). N-CAM protein was detected with the 4D monoclonal antibody (Developmental Studies Hybridoma Bank). For both, an alkaline phosphatase-conjugated secondary antibody was detected using NBT/BCIP as the substrate.

Images were obtained using incident or transillumination on a Zeiss axiophot or Zeiss stereomicroscope and were captured by video using a 3-color video rate CCD camera controlled by Northern Exposure software (Phase 3 Imaging Systems).

Isolation of Genomic Clones

To produced haploid embryos, eggs were fertilized with UV-irradiated sperm: a thin layer of macerated testis was UV irradiated at a distance of 13 mm for 5 minutes using a Mineralight lamp (model UVGL-25 from UVP, Inc.). >95% of tadpoles from fertilizations with these sperm had the stunted, microcephalic phenotype characteristic of haploid embryos (Gurdon, 1960) and had a haploid karyotype. Genomic DNA was isolated from single haploid embryos and digested with Not I. Primers contained 3' sequences matching only one cDNA: gem L primers corresponding to our cDNA were 5'-agcaacatgaagcagagatc (SEQ ID NO.: 36) and 5'-aatcagatgtcaagcttcgc (SEQ ID NO.: 37) and primers to gem H were 5'-caacaagaagcagagattg (SEQ ID NO.: 38) and 5'-agcctagacagtatgtgc (SEQ ID NO.: 39). Each primer set was demonstrated to be specific to one of the cDNAs and was then used to amplify three samples of haploid genomic DNA (25 cycles, 60¼C. annealing temperature). In all genomic samples, both gene-primer sets amplified bands of approximately 3 kb. These bands were isolated, sequenced, and found to correspond to genomic copies of gem L and gem H respectively.

RT-PCR

Gene expression in animal cap explants was analyzed by RT-PCR (Wilson and Melton, 1994). Primers for muscle actin, EF-1a, otx 2, and Hox B9 have been described (Wilson and Melton, 1994; Rao, 1994). Other primers for RT-PCR were: BMP4 (5'-attggattgtggcacctcct (SEQ ID NO.: 40) and 5'-ttggatctcagactcaacgg (SEQ ID NO.: 41)), X-ngnr-1 (5'-tacatctgggctcttagcga (SEQ ID NO.: 42) and 5'-caaatgaaagcgctgctgg (SEQ ID NO.: 43)), geminin (5'-gctggacatgtaccagtaca (SEQ ID NO.: 44) and 5'-tcacctcacataaaggctgg (SEQ ID NO.: 45)) and otx 2 (5'-ggatggatttgttgcaccagtc (SEQ ID NO.: 46) and 5'-cactctccgagctcacttctc (SEQ ID NO.: 47)). In embryos injected with gem RNA, endogenous geminin was detected with the second (reverse primer) described above and the following forward primer (5'-gtggccggtaacatttcgaa (SEQ ID NO.: 48)), as these sequences are within the 3' untranslated region not included in the injected RNA. For each primer set, we determined whether amplification was within a linear range by using dilutions of reverse-transcribed cDNA from embryonic samples as a PCR template and quantitating the band intensities with a Molecular Dynamics Phosphorimager.

Results

Expression Cloning of Geminin Assayed by its Neuralizing Effects

A cDNA library made from Xenopus blastulae (st. 6–7) was subdivided into pools of 100–300 clones each. To identify activities that could alter the embryonic axis, these pools, transcribed into RNAs, were injected into dorsal or ventral blastomeres of 4-cell Xenopus embryos. As about 2 ng of pool RNA was injected into each embryo, we selected for clones that could produce visible effects at doses of approximately 5–20 pg. One such clone caused expansion of the neural plate. We subdivided this positive pool, assaying smaller pools until we identified a single active clone.

Figure 8A:
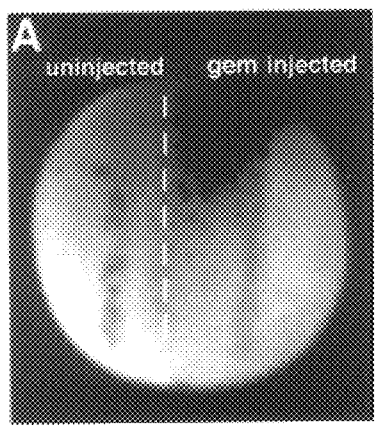
FIGS. 8A–H illustrate ectopic neurogenesis and neural plate expansion in embryonic ectoderm injected with Geminin in one bilateral half (oriented to the right). In situ hybridization detects cells expressing N-tubulin (FIGS. 8A–G) and cells expressing injected Geminin (FIGS. 8A–E; H) either from an expression plasmid (FIGS. 8A, H) or from 15 pg injected full-length (FIGS. 8F, G) or 250 pg Ngem (FIGS. 8B–E) RNAs. Endogenous Geminin RNA is not visible.
Figure 8B:
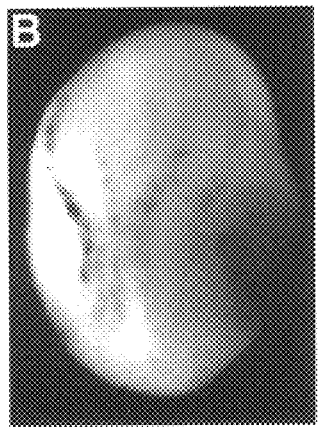
Figure 8C:
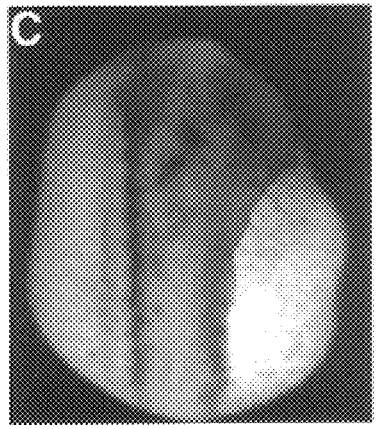
Figure 8D:
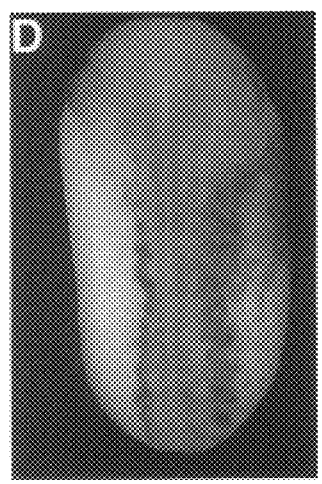
Figure 8E:
Figure 8F:
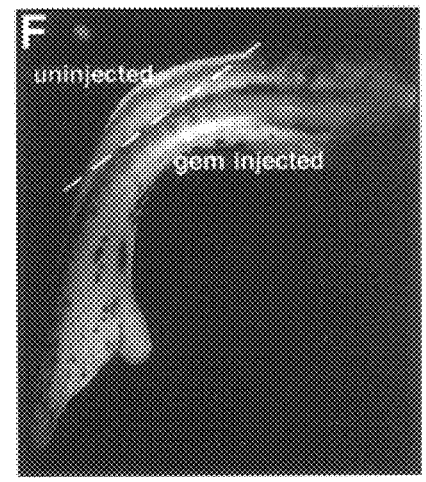
Figure 8G:
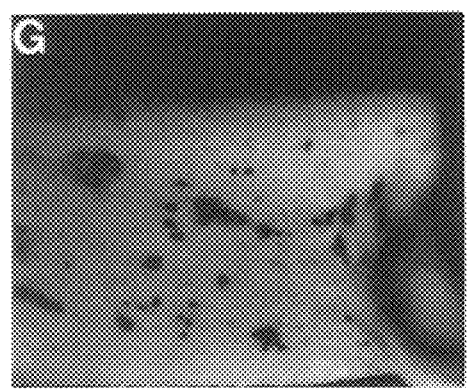

To characterize further the activity of this gene product which we named geminin, we injected RNA into one bilateral half of the embryo at the two cell stage and used in situ hybridization to detect perturbations of gene expression in the early nervous system. A neural-specific isoform of b-tubulin (N-tubulin; Richter et al., 1988; Oschwald et al., 1991) was used to detect primary neurons. At early neurula through tailbud stages, hypertrophy of neural tissue was visible on the injected side (FIG. 8). In some embryos, density of primary neurons increased (FIG. 8, D). In other embryos, more N-tubulin expressing tissue formed laterally but this tissue appeared disorganized with discrete stripes of primary neurons replaced by a large patch of neurectoderm that expressed many neural-specific genes including N-tubulin (FIGS. 8C, E), otx 2 (FIG. 9B)(Lamb et al., 1993), and Pax 6 (Hirsch and Harris, 1997) and Delta (Chitnis et al., 1995a)(data not shown). Anterior structures such as the otic vesicle and eye anlagen were often replaced by a patch of N-tubulin positive cells in these embryos. Extreme anterior structures such as the olfactory placode (FIG. 9A) and cement gland were sometimes also replaced by a patch of N-tubulin positive cells. More often, they remained visible but were expanded in size. The earliest expression of N-tubulin in gem-injected embryos was often slightly delayed in the injected half relative to the control half and, when primary neurons initially formed, they were in a more lateral position than those on the uninjected side (FIG. 8A).

Figure 8H:
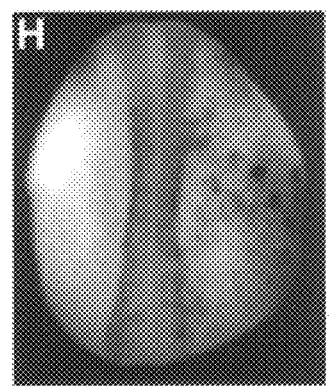
Figure 9A:
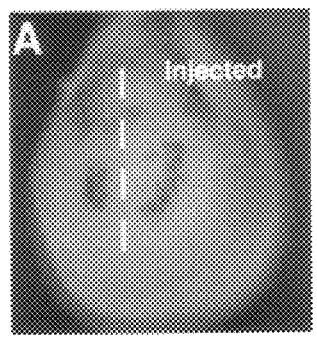
FIGS. 9A–I show that Geminin suppresses epidermal and expands neural gene expression.
Figure 9B:
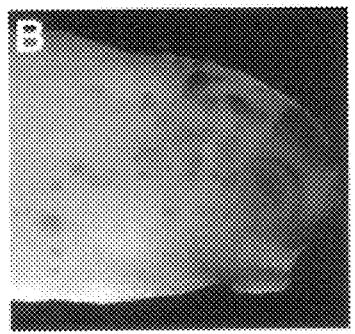
Figure 9C:
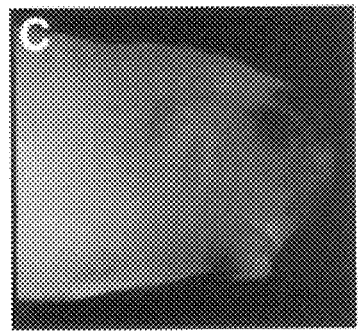

Dorsal hypertrophy of neural tissue was found in >85% of embryos injected with gem RNA or with a plasmid placing gem expression under control of the cytomegalovirus promoter to restrict expression to after the mid-blastula stage (pCMVgem). Ventral and lateral ectoderm was also converted to N-tubulin expressing neural tissue by gem misexpression (FIGS. 8B, F, G, H), although higher levels of misexpression were required than for obtaining dorsal hypertrophy. For example, geminin misexpression from injected mRNA or from pCMVgem plasmid induced N-tubulin relatively rarely in ventral cells (fewer than 5% of injected embryos in each experiment). However, N-tubulin was frequently induced in ventral and lateral tissue (64% for 3 experiments; N=388) when a plasmid that elicits stronger transcription of geminin was used (pUASgem). In pUASgem, geminin transcription is under the control of GAL4 upstream activating sites with coinjected GAL4 RNA driving expression (FIG. 8H). We found that pUASgem drove substantially higher levels of geminin transcription than pCMVgem.

Figure 9D:
Figure 9E:
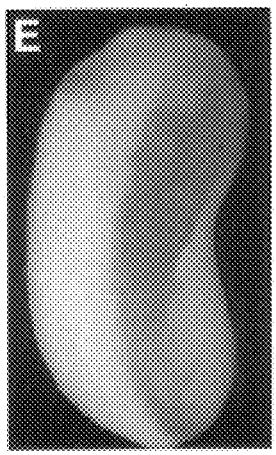
Figure 9F:
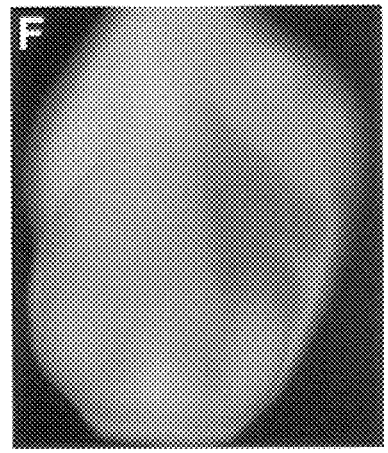
Figure 9G:
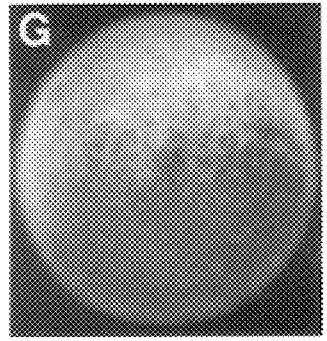
Figure 9H:
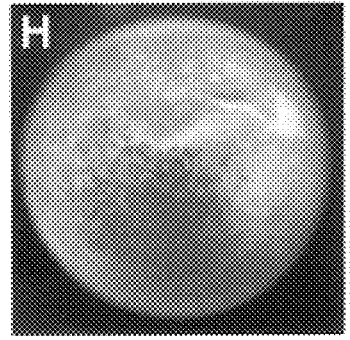
Figure 9I:
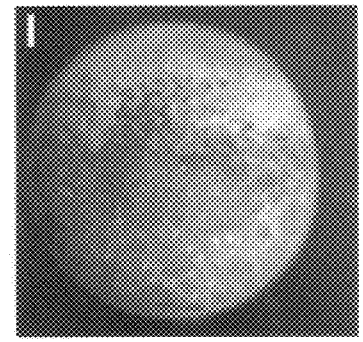

Ventral and lateral ectoderm injected with even very low doses of geminin failed to differentiate into epidermis, as measured by loss of expression of an epidermis-specific keratin (FIGS. 9G, H) (Jonas et al., 1985). This was consistent with conversion of this ectoderm to neural tissue. Formation of neural crest was sensitive to the dose of geminin injected. At geminin doses that effectively neuralized ectoderm, cells expressing the cranial neural crest marker twist (Hopwood et al., 1989) did not form on the injected side of the embryo (FIGS. 9D, E). By contrast, a ten-fold lower dose of geminin expanded the twist-expressing domain (FIG. 9F). This is consistent with observations that minimal concentrations of several neural inducers sufficient to inhibit epidermal keratin upregulate expression of a neural crest marker without inducing N-CAM, whereas N-CAM inducing doses of the same molecules suppress neural crest (Morgan and Sargent, 1997). Neural crest is formed by cellular interactions occurring at neural plate borders where neural and non-neural ectoderm are juxtaposed (Moury and Jacobson, 1990; Selleck and Bronner, 1995) and subthreshold concentrations of neural inducing activity may be present at these boundaries.

Geminin is a Novel Neuralizing Molecule

The effects caused by ectopic expression of geminin in embryos were reminiscent of those elicited by several proneural genes which act to specify neural determination. In Xenopus, identified genes that have an overexpression phenotype resembling geminin include the atonal homologue (XATH-3) (Kim et al., 1997; Takebayashi et al., 1997), an achaete-scute homologue (XASH-3) (Zimmerman et al., 1993; Ferreiro et al., 1994; Turner and Weintraub, 1994), the neural determination gene X-ngnr-1 (Ma et al., 1996) and the neural differentiation gene neuroD (Lee et al., 1995), all basic helix-loop-helix family transcription factors. These effects also resembled misexpression of a POU-domain transcription factor, XlPOU2 (Witta et al., 1995) also a likely proneural gene. However, geminin's sequence bears no resemblance to these or other known molecules.

Figure 10B:
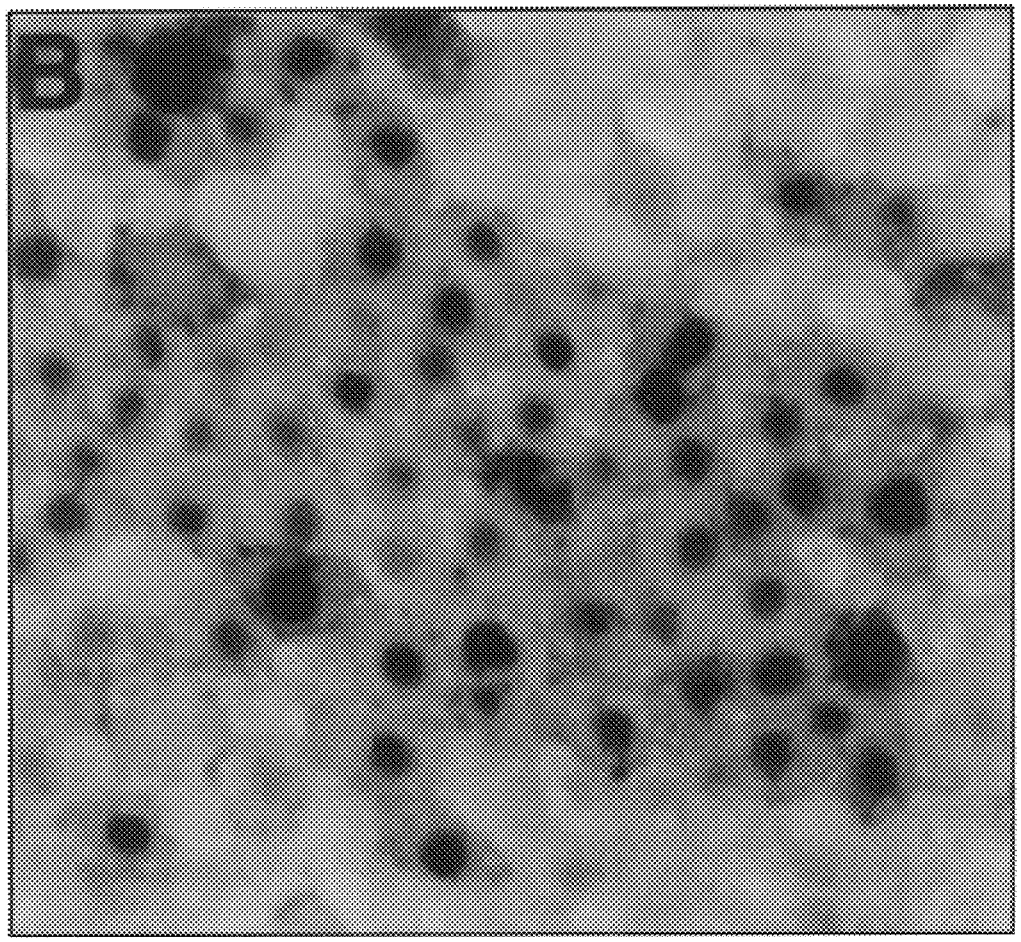

The Xenopus geminin cDNA encodes a highly charged protein of 217 amino acids. By low stringency hybridization and sequence database searches, we detected genes related to geminin in other vertebrates (zebrafish, mouse, and human) but not in yeast (Saccharomyces cerevisiae). We isolated a related cDNA from mouse encoding a 207 amino acid protein that is 46% identical to the Xenopus protein (FIG. 10A). The C-terminal domain of geminin contains heptad amino acid repeats predicted by the Parcoils (Berger et al., 1995) and Lupas algorithms (COILS program, version 2.1; Lupas et al., 1991) to form a coiled coil domain commonly used in protein dimerization. To determine the intracellular localization of geminin protein, we added myc epitopes to the N-terminus of geminin, injected plasmid encoding this fusion protein into early embryos, and immunostained to detect the myc epitope. We found that most gem protein translocated to the nucleus (FIG. 10B).

By sequence similarity, the two Xenopus gem cDNAs are 85% identical within the open reading frame, although the 5' and 3' untranslated regions and sequences of the introns are much less highly conserved. Since the predicted proteins encoded by these cDNAs vary by 3 amino acids in size we use the designations L (light) and H (heavy) to denote the cDNA reported here and that reported by McGarry and Kirschner (personal communication) respectively. To determine whether these cDNAs represented two separate genes or rather two alleles of the same gene, we assayed haploid genomes for the presence of each gene. In three haploid genomic backgrounds tested, we found that both genes were present and isolated genomic copies corresponding to both geminin cDNAs (see methods; data not shown).

We defined two functional domains of geminin in embryos by testing as series of geminin deletion mutants for activity. An N-terminal domain (amino acids 38–90; Ngem) was sufficient to evoke neural hypertrophy and ectopic neurogenesis when injected at RNA levels slightly higher than those required for the full length molecule. A C-terminal domain comprised of the coiled coils of the molecule (amino acids 112–168; Ccoil) was cytotoxic when expressed in early embryos. This domain has DNA replication inhibition activity and can fully account geminin's ability to regulate DNA replication in vitro. By contrast, the N-terminal domain has no effect on DNA replication or cell cycle progression is not cytotoxic in embryos at doses up to 2 ng, and can fully account for geminin's neuralizing activity. These cDNAs also contain a destruction box that is near but not contained in the N-terminal neuralizing fragment.

The neuralizing and cell cycle regulatory activities of geminin are physically separated into non-overlapping and independently acting domains. However, alteration of the cell cycle state could conceivably be a precondition for neural determination or differentiation such that physical association of these domains would be advantageous. To test whether blocking the cell cycle elicited ectopic neurogenesis, we treated embryos with hydroxyurea and aphidicolin (HUA) from the early gastrula stage. This HUA treatment, as described by Harris and Hartenstein (1991), blocks virtually all cell division and did not elicit neural hypertrophy in previous studies (Turner and Weintraub, 1994; Takebayashi et al., 1997). Likewise, we found that HUA treatment alone had no effect on neural plate formation or expression of neural genes. We also conversely found that neural hypertrophy elicited by geminin was not attributable to increased cell division as it occurred in HUA-treated embryos previously injected with geminin mRNA. Therefore, the neuralizing effects of geminin were neither sensitive to nor caused by perturbation of the cell cycle.

Geminin Demarcates the Future Neural Plate in Early Gastrulae

Figure 10C:
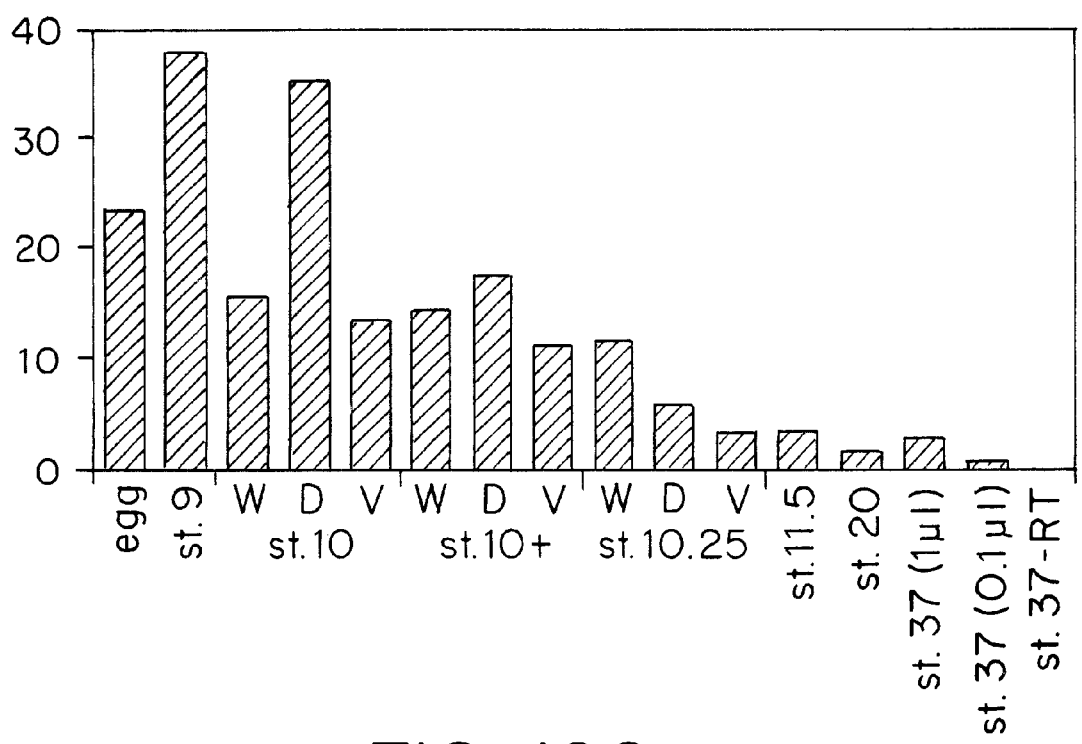
Figure 11A:
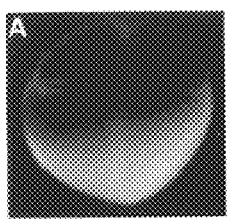
FIGS. 11A–L show spatial distribution of Geminin transcripts in the early embryo identified by in situ hybridization.
Figure 11B:
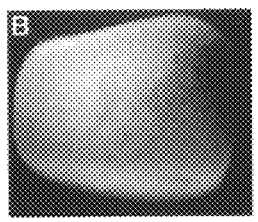
Figure 11C:
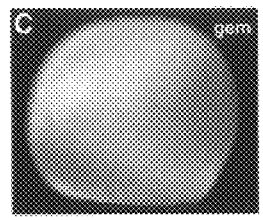
Figure 11D:
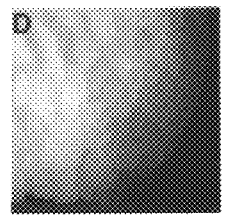
Figure 11E:
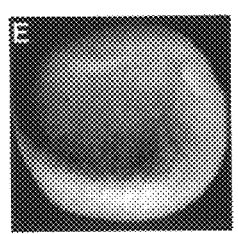

At the onset of gastrulation in Xenopus, geminin mRNA is restricted to presumptive neural tissue (FIGS. 11B–D). Before that, transcripts are present uniformly in st. 3–4 oocytes but are restricted to the animal hemisphere by stage 6 of oogenesis. During early cleavages, gem mRNA is found in the entire animal hemisphere (FIG. 11A) with the protein also being predominantly localized to animal blastomeres at these stages. However, geminin mRNA becomes further restricted to a dorsal ectodermal territory at the onset of gastrulation (stage 10– to 10). At this time, geminin transcript levels increase dorsally relative to levels found in an equivalent volume of egg cytoplasm (FIG. 10C). This indicates that the dorsal enrichment of geminin mRNA seen by in situ hybridization must be due, at least in part, to new dorsal transcription. Ventrally, transcript levels are lower than levels found in the egg, although we can not determine from this whether the rate of gem mRNA turnover differs in dorsal versus ventral tissue.

Figure 11F:
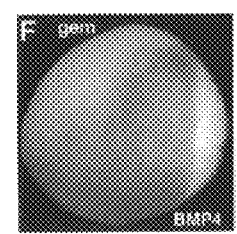
Figure 11G:
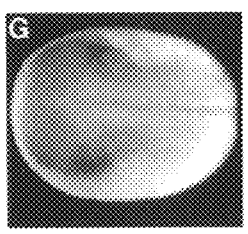

Early in gastrulation, geminin transcripts are cleared from both ventral ectoderm and from the marginal zone, such that the domain of gem expression does not overlap with brachyury, which is expressed in presumptive posterior mesoderm (FIGS. 11C, D). BMP4 is expressed throughout the animal hemisphere and marginal zone in early gastrulae and the same cells thus express both geminin and BMP4 at these stages. By mid-gastrulation, however, expression of geminin and BMP4 is largely complementary and non-overlapping (FIG. 11F). BMP4 mRNA is restricted to ventral ectoderm and mesoderm, while geminin mRNA is restricted to dorsal ectoderm.

Figure 11H:
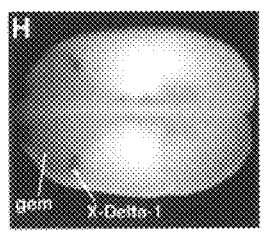
Figure 11I:
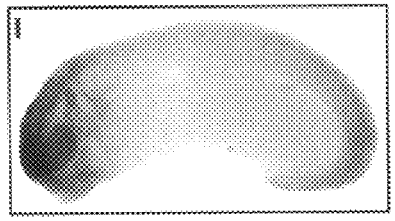
Figure 11J:
Figure 11K:
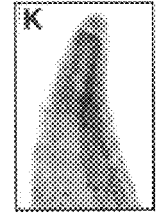

During neural plate stages, geminin is expressed in a wide anterior ectodermal territory that contributes to placodes, neural crest and neural plate. In trunk neurectoderm, gem mRNA levels are slightly higher at the midline (notoplate) and at the lateral edges. Anteriorly, the lateral edge of the geminin expression domain is marked by the trigeminal ganglia (FIG. 11H). After neural tube closure, gem is expressed in both the floorplate and roofplate of the neural tube and more anteriorly throughout the brain, in the eye vesicle, nose, otic vesicle, in cephalic neural crest and in a dorsal region of the tailbud contiguous with the dorsal neural tube.

Figure 11L:
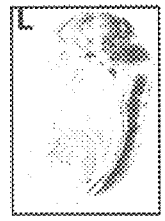

We also used in situ hybridization to mouse embryo tissue sections to visualize the expression pattern of the mouse gene. Mouse geminin becomes enriched in the nervous system by about day e8 to e9, although some staining outside the neural tube is also visible. At later stages (e15), expression localizes to cranial and trunk nerves, the trunk neural tube and much of the brain (FIG. 11L).

Geminin Suppresses BMP4 Expression and Epidermal Fate at Gastrulation

Figure 12A:
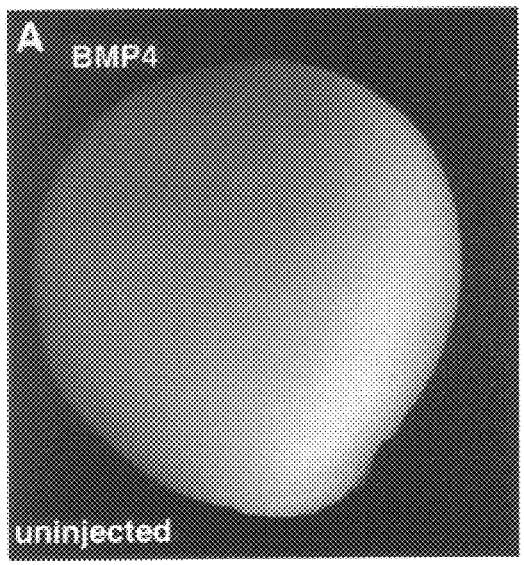
FIGS. 12A–D demonstrate the Geminin inhibits expression of the epidermalizing growth factor, BMP4, in ventral and lateral ectoderm during gastrulation. BMP4 expression occurs in lateral and ventral ectoderm of uninjected embryos (FIG. 12A) but is eliminated by injection of 250 pg Ngem RNA (FIGS. 12B–C).
Figure 12B:
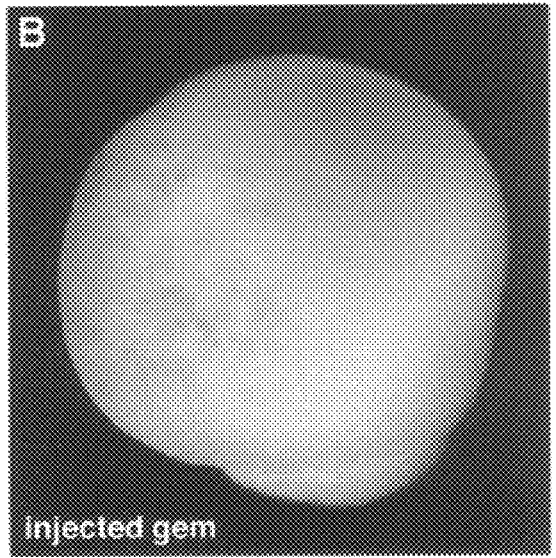
Figure 12C:
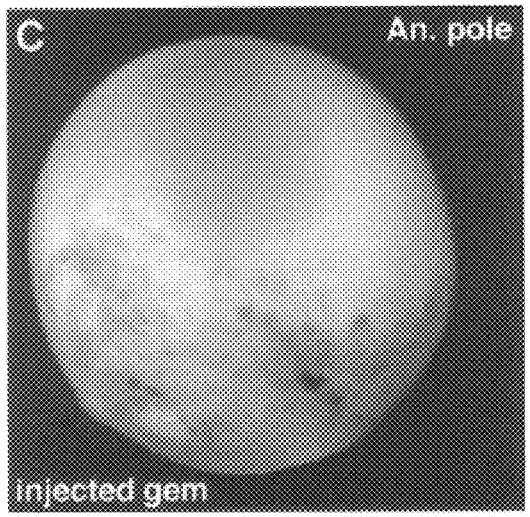
Figure 12D:
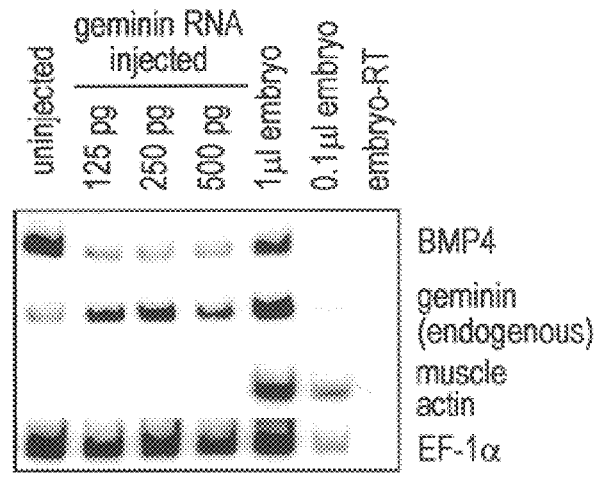

While we identified geminin by its effect on neural plate boundaries, we found gem had much earlier effects on ectodermal cells. Injection of gem RNA into lateral or ventral ectoderm caused a loss of BMP4 mRNA that was visible during gastrulation in these cells (FIGS. 12B, C). A like decrease in BMP4 transcript levels occurred in isolated ectoderm injected with geminin (FIG. 12D). These effects were elicited by low doses of full length or Ngem RNA (10 to 100 pg) or injection of pCMVgem plasmid. At the onset of gastrulation, geminin expression is upregulated in dorsal ectoderm prior to the loss of BMP4 mRNA from these cells (FIGS. 11B–D, FIG. 13A and Hemmati-Brivanlou and Thomsen, 1995). By contrast, BMP4 transcripts persist throughout gastrulation in lateral and ventral ectoderm not expressing geminin (FIG. 11F). Thus, both geminin's action and its pattern and timing of expression suggest a role in down-regulating BMP4 expression in dorsal ectoderm during gastrulation.

Figure 13A:
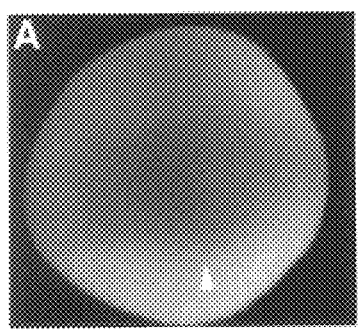
FIGS. 13A–F show that BMP4 can relieve Geminin's suppression of epidermal development.
Figure 13B:
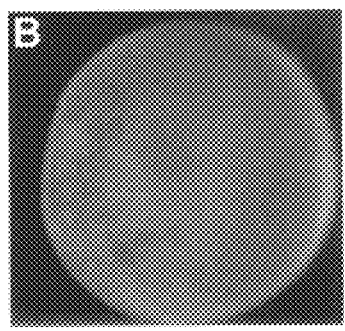
Figure 13C:
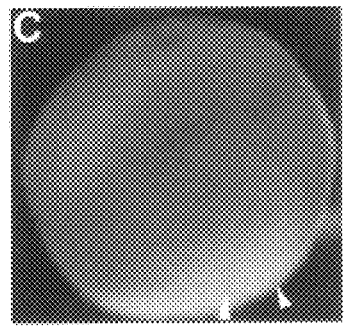
Figure 13D:
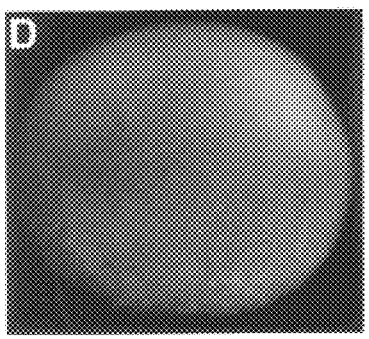
Figure 13E:
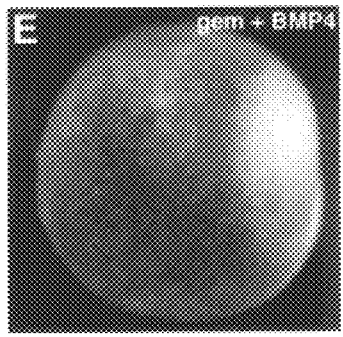

Does geminin's antagonism of BMP4 mRNA persistence in dorsal ectoderm account for its neuralizing properties? To address this question, we first compared the expression of geminin with that of epidermal keratin between stage 9 and 10.5. At the onset of gastrulation (st. 10– to 10), geminin expression is upregulated in dorsal ectoderm and transcripts are rapidly turned over in lateral and ventral cells, restricting geminin mRNA to dorsal ectoderm (FIG. 13A). Epidermal keratin is not present in these embryos at levels detectable by in situ hybridization. Shortly thereafter (st. 10+ to 10.25), levels of epidermal keratin rise in lateral and ventral cells outside of the geminin-expressing domain while keratin never appears in dorsal cells (FIGS. 13B, C). At later stages, expression continues to localize to non-overlapping ectodermal domains (FIGS. 13, D).

Figure 13F:
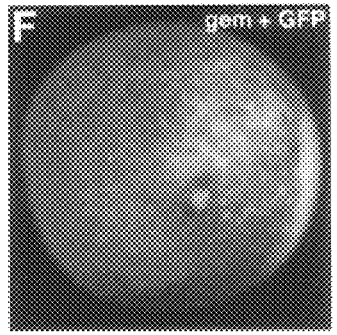

Geminin expression precedes restriction of BMP4 and epidermal keratin expression to ventrolateral cells. When misexpressed, geminin causes both BMP4 and epidermal keratin mRNAs to be lost from cells fated to form epidermis. These observations are consistent with a mechanism where downregulation of BMP4 RNA levels is the primary means by which geminin neuralizes ectoderm. If this is so, coinjection of BMP4 mRNA with geminin should rescue epidermalization in coinjected cells. We found this indeed to be the case. Ventral cells coinjected with BMP4 mRNA and geminin in a 1:1 ratio formed epidermis (FIG. 13E), whereas ventral cells injected the same dose of geminin and mRNA for green fluorescent protein failed to express epidermal keratin, as expected from geminin's activity (FIG. 13F). Therefore, many of geminin's neuralizing properties could be attributed to its ability to lower intracellular BMP4 mRNA levels in dorsal ectoderm during gastrulation.

Geminin is Induced by Organizer Molecules and Induces Neural Genes

Figure 14A:
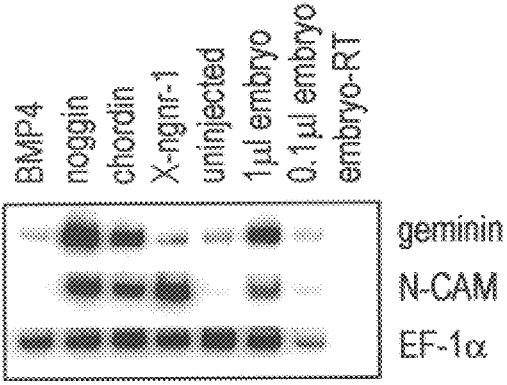
FIGS. 14A–F show that Geminin is induced by organizer signals and activates neural gene expression in isolated ectoderm.

To determine how induction of geminin expression in dorsal ectoderm might occur in the embryo we tested several neural inducers and proneural genes for effects on geminin mRNA levels in isolated ectoderm (FIG. 14A). Both noggin and chordin strongly induced geminin expression. By contrast, the proneural gene X-ngnr-1 which shows the earliest onset of neural expression in the embryo failed to induce geminin. These data are consistent with the observation that dorsal upregulation of geminin transcription occurs at stage 10– to 10, after the onset of organizer gene expression (st. 9) but prior to expression of proneural genes including X-ngnr-1 (st. 10.5 to 11). We also found that geminin could induce its own expression (FIG. 12D). BMP4 had neither a stimulatory nor inhibitory effect on geminin transcription (FIG. 14A).

Figure 14B:
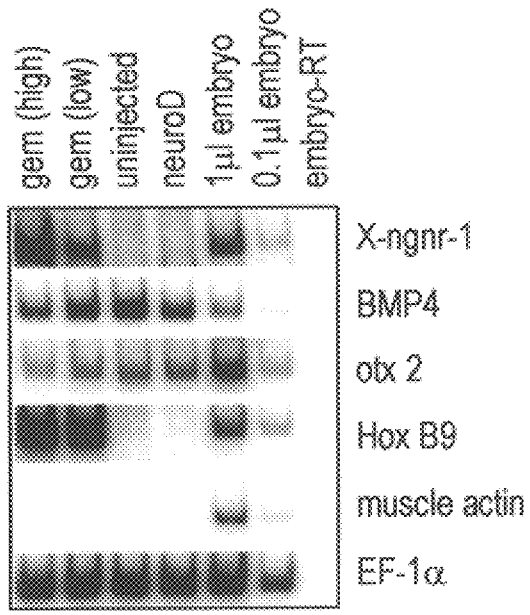
Figure 14C:
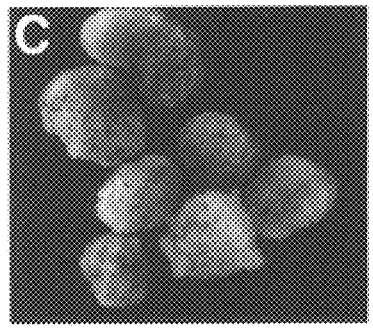
Figure 14D:
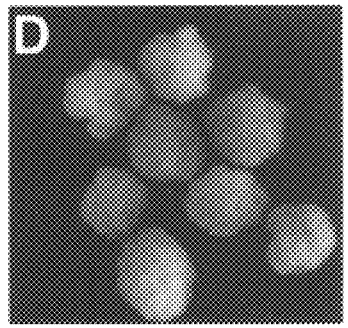
Figure 14E:
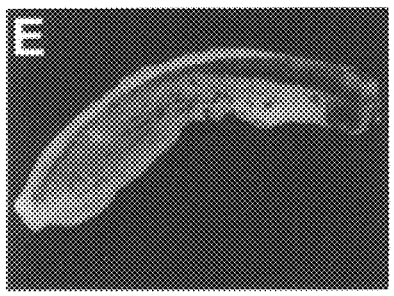
Figure 14F:

Consistent with its ability to repress BMP4 and epidermal keratin expression and induce neural gene expression in ventral cells of the embryo, we found that geminin could induce neural gene expression in isolated ectoderm. The proneural gene X-ngnr-1 was strongly induced in the absence of muscle actin gene expression, indicating that geminin's neuralizing activity is direct and not mediated by the formation of mesoderm with neural-inducing properties (FIG. 14B). N-CAM expression was also activated in this ectoderm (FIG. 14C) and in ventral tissue of injected embryos (FIGS. 14E, F). However, by comparison with X-ngnr-1 or neuroD, the level of N-CAM induction in ectodermal explants was relatively weak. N-CAM was induced in explants injected with a plasmid that drives robust transcription of geminin (pUASgem) but not by 10–20 pg of gem RNA. This was consistent with results of gem RNA or plasmid injections into the ventral ectoderm of embryos (FIG. 8). By comparison, suppression of BMP4 mRNA levels was sensitive to injection of low doses of full length or Ngem RNAs. The posterior neural marker Hox B9 was induced by geminin, while expression of the anterior marker otx 2 (also expressed in non-neural ectoderm) was slightly suppressed. This was a somewhat surprising result, given that neural inducers that are thought to act strictly by antagonizing BMP receptor signaling (such as noggin, chordin, or dominant-negative receptors) induce neural tissue of anterior character. In this respect, geminin's neural inducing activity resembles that of FGF which has also been shown to induce posterior neural tissue in animal cap assays (Kengaku and Okamoto, 1995; Lamb and Harland, 1995). We speculate that this induction represents an effect of geminin on neural gene transcription that is separate from its effects on BMP4 transcription, but the mechanism by which this occurs or its relevance in vivo remain unclear.

Neurogenesis is Blocked by Overexpression of the C-terminal Domain

While testing deletion mutants of geminin for activity, we found that a C-terminal domain containing the coiled-coil protein dimerization motif (Cdim) antagonized neural development by contrast with effects of the full length or N-terminus of geminin. Dorsal cells injected with a plasmid containing Cdim driven by the cytomegalovirus promoter (pcdim) expressed epidermal keratin ectopically and were suppressed from expressing N-tubulin. This effect was rescued by coexpressing full-length geminin.

Figure 15A:
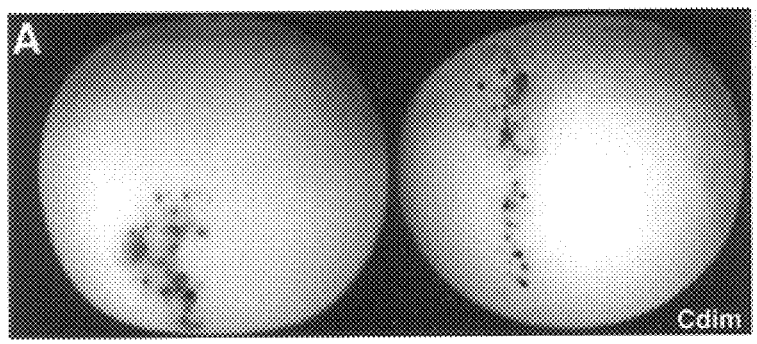
FIGS. 15A–F illustrate that a dominant negative Geminin induces epidermis and suppresses neural development in dorsal cells.
Figure 15B:
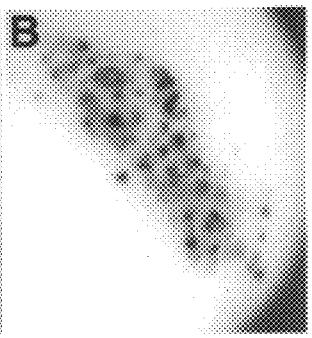
Figure 15C:
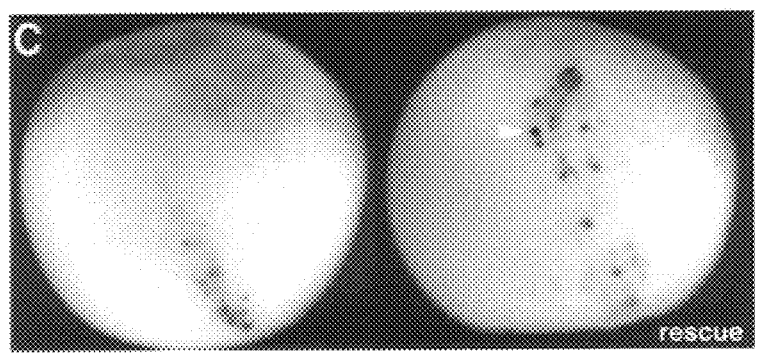
Figure 15D:
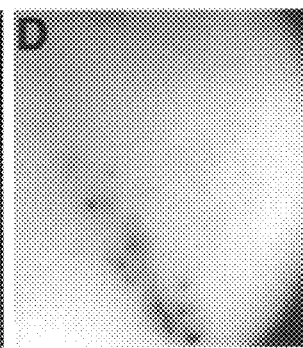

We analyzed epidermal keratin expression in gastrula stage embryos injected dorsally with either pcdim or with a rescue plasmid containing cassettes for expression of both Cdim and full length geminin, each from a separate CMV promoter (pCdim-gem). Epidermal keratin was expressed ectopically in 93% of embryos injected dorsally with pCdim (n=137; FIGS. 15A, B). Injection of pcdim-gem fully suppressed ectopic epidermal keratin expression in some embryos, while in others ectopic keratin was partially suppressed. Complete suppression of ectopic dorsal keratin expression was obtained by coinjection of full length geminin (pCMVgem) with pcdim-gem (100 pg each; 91%, n=216) (FIGS. 15C, D).

Figure 15E:
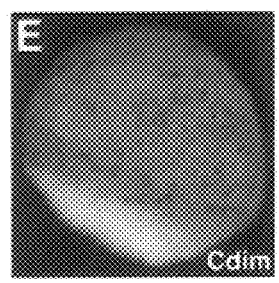
Figure 15F:
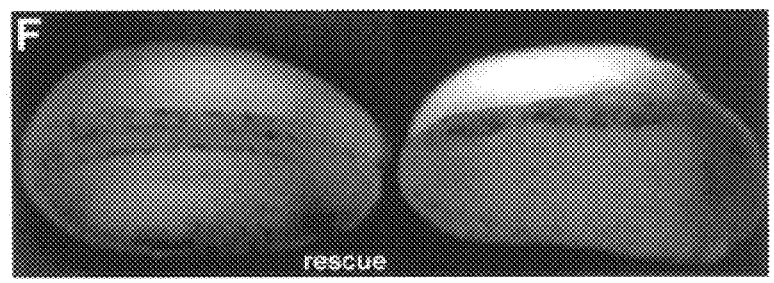

We also analyzed the effects of this dominant negative domain of geminin on the formation of endogenous neural tissue, detected by N-tubulin staining. Initially, we found that small regions of the neural tube expressing injected pCdim failed to express N-tubulin. We focused further analysis on transgenic embryos, as injected embryos were highly mosaic in the nervous system. Transgenic embryos expressing pCdim began gastrulation normally but cell movements appeared to arrest during gastrulation and later embryos were severely disturbed with no visible axial structures (FIG. 15E). Most of these embryos (86%; n=76 for two experiments) completely lacked N-tubulin staining while the others showed a partial loss of N-tubulin staining. Expression of pcdim-gem restored full N-tubulin staining to 89% of the embryos (n=95 for two experiments) although it did not rescue normal morphology in many embryos (FIG. 15F). The ability of this rescuable C-terminal domain construct to cause ectopic epidermis formation and to suppress neural tissue formation in dorsal ectoderm indicates that geminin could be required for some aspect of neural cell determination.

Discussion

The Role of Geminin in Neurogenesis

Geminin was cloned based on its potent activities in the embryo, which resemble those of the proneural genes (Ferreiro et al., 1994; Kim et al., 1997; Lee et al., 1995; Ma et al., 1996; Takebayashi et al., 1997; Turner and Weintraub, 1994; Witta et al., 1995; Zimmerman et al., 1993). Geminin can expand the neural plate and induce ectopic neurogenesis in lateral and ventral ectoderm in the absence of induced mesoderm and when expressed only at the time of neural induction. At even low doses, misexpressed geminin suppresses BMP4 mRNA expression or persistence in ventral ectoderm and blocks epidermal keratin expression. Geminin's expression pattern is consistent with a role in controlling BMP4 transcript levels in dorsal ectoderm as geminin defines a future neural territory in early gastrula ectoderm from which BMP4 transcripts become excluded and in which epidermal keratin expression never occurs. Epidermis can also be rescued in ventral ectoderm misexpressing geminin if BMP4 transcripts are coinjected to replace those suppressed by geminin, further suggesting that some aspects of geminin's neuralizing activities are mediated by regulation of BMP4 transcript levels in dorsal ectodermal cells.

Most research on the early stages of neuralization has focused on secreted molecules produced by dorsal mesoderm. Geminin bridges a gap between these extracellular signals and later establishment of proneural gene expression within dorsal ectodermal cells. Geminin's expression demonstrates that a future neural territory is established in the ectoderm by stage 10, while the earliest expression of proneural genes occurs only later within a more restricted domain by st. 10.5 (X-ngnr-1) (Ma et al., 1996) or by st. 11 (X1POU2) (Witta et al., 1995). In addition to BMP4 and epidermal keratin, several homeobox genes begin to be expressed in or are restricted ventrally by stage 10.5 to 11. Ventral upregulation of some of these genes (msx-1, Suzuki et al., 1997 and Xom, Ladher et al., 1996) is an immediate, direct response to BMP signaling. Geminin's dorsal localization in future neurectoderm precedes these ventral restrictions of expression, and indicates that ectoderm is regionalized into dorsal and ventral domains earlier than was previously appreciated (by st. 10 to 10+). Geminin's expression and activities are also consistent with roles in controlling both down-regulation of epidermal inducers and later upregulation of proneural genes such as X-ngnr-1.

Noggin and chordin inactivate extracellular BMPs by direct protein binding. However, ectodermal cells would be expected to continue to express and secrete active BMP4 protein dorsally in the absence of some intracellular response to this extracellular attenuation of BMP receptor signaling. Geminin may represent such an early response, down-regulating BMP4 transcription and thus fully abolishing signaling by this BMP ligand dorsally during the period of early organizer signaling. Geminin's expression and dorsal accumulation could be stimulated by an initial attenuation of BMP signaling, as noggin and chordin induce geminin expression. Other dorsal signals may also be involved, such as those of the wnt pathway. Once present at high levels within dorsal cells, geminin can stimulate its own transcription, producing a positive autoregulatory circuit to reinforce dorsal fate. At the same time, geminin could mediate the complete loss of BMP4 mRNA and thus active BMP4 protein from the dorsal side of the embryo, establishing neural fate within the dorsal ectodermal cells. In Drosophila, BMP4 has been found to stimulate its own transcription, forming a positive autoregulatory loop that maintains and reinforces the epidermal state of cells in regions with high levels of extracellular BMP4 protein (Yu et al., 1996). There is some evidence such autoactivation may also occur in vertebrates (Schmidt et al., 1996; Jones et al., 1992), thus autoactivation circuits mediated by geminin and BMP4 on the dorsal and ventral sides of the embryo respectively might maintain well-defined neural and epidermal domains within the embryo and stimulate the expression of the appropriate downstream genes.

A secondary, intracellular system for controlling BMP4 levels might seem unnecessary if BMP4 antagonists are produced by the organizer at levels sufficient to block all protein that is produced. However, our experiments with expressed C-terminal domains indicate that geminin performs a function essential for establishing neural cell fate. In these experiments, epidermis was induced in dorsal ectoderm in immediate proximity to unperturbed, organizer mesoderm. Neural fate was rescued in these cells by expressing full-length geminin. Interpretation of these results is complicated by potential non-neuralizing functions of the C-terminal domain. This domain could inhibit other cellular functions, such as DNA replication. If the presence of excess C-terminal domain in the cell blocks geminin's interaction with another partner or the formation of active homodimers, expression of excess full length protein could overcome this inhibition. Hence the experiment can be best seen as an indication that one pathway involving geminin plays a direct or indirect role in neural specification.

Geminin as a Prepattern Gene in Ectodermal Regionalization

Both geminin's activities and expression pattern distinguish it from proneural genes that have been identified in vertebrates. Geminin is expressed in an earlier or broader pattern than any known proneural gene, demarcating the future neural plate by early gastrulation. This expression establishes a dorsal ectodermal domain in which cells will down-regulate BMP4 expression, fail to express epidermal keratin, and later express proneural genes, all cellular functions that can be performed by geminin. Unlike the proneural genes, geminin's expression never localizes specifically to primary neural clusters.

In keeping with its early expression pattern, geminin is more effective at inducing early neural markers than late. Doses of geminin that effectively suppress epidermal keratin and BMP4 are five to ten-fold lower than those needed to induce neural tissue. While geminin can induce neurogenesis in lateral and ventral ectoderm (unlike the proneural gene XASH-3; Turner and Weintraub, 1994), geminin expression results in fewer ectopic neurons than is seen in embryos injected with other proneural genes such as X-ngnr-1 (Ma et al., 1996) or neuroD (Lee et al., 1995). This may reflect geminin's in vivo role, as many cells expressing geminin during gastrulation do not later become neurons. Geminin may activate downstream processes that further select sites of primary neuron formation within the dorsal ectodermal cell field. In many respects, therefore, geminin appears to act earlier and more generally to subdivide ectoderm into neural and non-neural territories, with activities of downstream genes later determining neuronal fate within individual dorsal cells.

In Drosophila, genes play a similar prepatterning role in domains of the wing imaginal disc where proneural gene activity later occurs. Formation of the sensory organs is controlled by activation of the proneural genes achaete (ac) and scute (sc) in small clusters of cells. While factors controlling ac-sc expression are still poorly understood, two recently identified homeodomain genes are expressed in broader regions of the wing imaginal disc than the ac-sc expressing clusters and can directly activate ac-sc transcription. These genes, named araucan and caupolican, are designated "pre-pattern" genes because their expression pattern and activities fill a gap between genes such as engrailed and hedgehog that broadly subdivide the imaginal discs and expression of ac-sc in small clusters of cells (Gomez-Skarmeta et al., 1996). In a similar manner, geminin responds to early dorsal-ventral patterning cues to demarcate a dorsal ectodermal domain within which proneural genes later act to establish neural cell fate.

Geminin is a Bifunctional Molecule

We found that geminin's neuralizing activity localized to an N-terminal domain. A non-overlapping C-terminal domain comprised of the predicted coiled coil region had no neuralizing activity and was toxic when expressed at high levels in cleaving embryos (from injected RNA). However, this C-terminal domain was not deleterious to embryonic development if expression was restricted to after the midblastula transition in transgenic or plasmid-injected embryos, at levels that may be much lower. Furthermore, this C-terminal domain antagonized the function of the entire molecule and interfered with neurogenesis. McGarry and Kirschner have found that the coiled-coil domain of geminin inhibits the initiation of DNA replication, which may correspond to the early toxicity that we observed. As shown previously, inhibition of replication after the early gastrula stage has little effect on neural specification (Harris and Hartenstein, 1991).

Since the C-terminal domain of geminin may regulate cell cycle progression, an intriguing possibility was that physical connection of neuralizing and DNA replication inhibition domains within geminin could coordinate a switch from proliferation to differentiation occurring after the neural cell fate decision. Thus far, however, we have found no simple link between the two processes during early neural specification. Inhibition of DNA replication did not alter neural patterning in embryos, indicating that this was not sufficient to stimulate effects on the nervous system we have observed. This is supported by similar studies with proneural genes (Turner and Weintraub, 1994; Takebayashi et al., 1997). Likewise, the domains sufficient to neuralize in vivo or block DNA replication in vitro are non-overlapping within the molecule, so neither function can be explained as a consequence of the other. Thus we cannot yet determine whether different cofactors control these two functions or speculate as to whether there are biological contexts, such as promoting the terminal differentiation of neurons, that might be more likely to use both functions coordinately. Studies to address these issues are underway.

Geminin's Mechanism of Action

Geminin is a novel molecule that can coordinately alter transcription in ectodermal cells. While geminin is nuclear, we have as of yet no evidence that this protein binds to DNA directly, although this would certainly account for its ability to affect transcription. Another possibility is that geminin interacts with transcription factors or other nuclear or cytoplasmic proteins to alter their activity; geminin may either interfere with the activity of epidermalizing molecules or may activate molecules in the neuralization pathway. In yeast, full length geminin contains some transcriptional activation activity, detected when it is fused to a GAL4 DNA binding domain. It will be of interest to identify the binding partners of geminin.

The activities of the organizer in neural induction surprisingly are biochemically simple, direct inhibitors of BMP protein activity. Yet these inhibitors lead to the demarcation of the neural plate and ultimately the patterning of the nervous system. We might expect that other patterning processes are involved in building up complexity and delineating more accurately the domains of neural function. Such activities would come as a response to mesodermal signaling in the neural plate. Geminin potentially represents such an activity. Although it is not obvious how it functions biochemically, it seems clear that geminin mediates an important patterning event early in neural specification.

EQUIVALENTS

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A plasmid or vector comprising the nucleic acid sequence of SEQ ID NO.: 4 or 20, or the complement of SEQ ID NO.: 4 or 20.

2. A cell transfected with a nucleic acid of SEQ ID NO.: 4 or 20, or the complement of SEQ ID NO.: 4 or 20.

3. An isolated nucleic acid molecule that comprises a nucleic acid sequence that encodes SEQ ID NO.: 8 or 24.

4. A plasmid or vector comprising a nucleic acid sequence that encodes SEQ ID NO.: 8 or 24.

5. A cell transfected with a nucleic acid that encodes SEQ ID NO.: 8 or 24.

6. An isolated nucleic acid molecule that comprises a nucleic acid sequence that encodes SEQ ID NO.: 8 or 24 having a non-functional, mutated or deleted destruction box sequence.

7. The isolated nucleic acid sequence of claim 6, wherein the isolated nucleic acid encodes a protein with a non-functional or deleted destruction box sequence that comprises a deletion of at least one of the amino acid Numbers 33–41.

8. The isolated nucleic acid of claim 6, wherein the nucleic acid encodes a protein with a mutated destruction box sequence comprising a substitution of the L at amino acid Number 36 with an A.

9. An isolated nucleic acid molecule that comprises:
a) a nucleic acid sequence of SEQ ID NO: 4 or 20; or
b) the complementary strand of a).

10. An isolated nucleic acid sequence that encodes SEQ ID NO.: 4 or 20, wherein the nucleic acid is RNA.

* * * * *

SEQUENCE LISTING

<160> NUMBER OF SEQ ID NOS: 48

<210> SEQ ID NO 1
<211> LENGTH: 651
<212> TYPE: DNA
<213> ORGANISM: xenopus

<400> SEQUENCE: 1

| | | | | | |
|---|---|---|---|---|---|
| atgaatagca | acatgaagca | gagatctgat | gtagagaacc | cttccatgtc | aattaagaac | 60 |
| tacattgtag | ataaaacaaa | tgaggcactt | gcaccaagaa | gaacacttaa | agtaatccag | 120 |
| caatctgcat | ctgggtgcct | tgttggaagg | accaaagagc | ctgctaaaaa | ttctacaaaa | 180 |
| agaaaactat | ggaatgatca | actgacttca | aaaaggcta | aagttgaagt | ggctgttgat | 240 |
| ccagaacacc | aggaaaacaa | ggattgccca | tctgaagcat | atgacctcat | ggtgaaagaa | 300 |
| accccaactt | gtctgtactg | gaaggatgtt | gcagaggaaa | gaagaaaggc | cctctatgaa | 360 |
| gcattacaag | aaaatgagaa | gctgcatcaa | gaaatagaac | tcaaagatga | agaaattgca | 420 |
| cgcttgaaac | aagaaaatga | tgaattaatg | gaacttgctg | gacatgtaca | gtacatggcg | 480 |
| aatatgattg | aaaggctcac | tggaaatgca | ccacaaagtc | ttgaagattt | aaagaatttg | 540 |
| gatttagaag | aagcaaggtt | tgaagatgaa | gcagaatcaa | ggattgaaga | tgaaactgat | 600 |
| atgactcagc | cctcaagttc | agatcagaac | atggataaac | aaactgtcta | g | 651 |

<210> SEQ ID NO 2
<211> LENGTH: 660
<212> TYPE: DNA
<213> ORGANISM: xenopus

<400> SEQUENCE: 2

| | | | | | |
|---|---|---|---|---|---|
| atgaatacca | acaagaagca | gagattggat | atggagaagc | ctaccatgtc | tattaagaac | 60 |
| tactttgtgg | ataaaacaaa | cgagtcccct | gcacccagaa | gaacacttaa | agtaatccag | 120 |
| ccatctgcat | ctggatgcct | tgttggaagg | accaaagagc | ctgttaaaaa | ttctacaaaa | 180 |
| agaaagctgt | ggaatgatca | gctgacttca | aaaaggcta | aagttgaagt | ggctgttgat | 240 |
| ccagaacaca | gggaaaacaa | agattgctca | tctgaagctt | atgaccttat | ggtgaaagaa | 300 |
| acaccaactt | gcctttactg | gaaggaggtt | gcagaggaac | gaagaaaggc | cctctatgaa | 360 |
| gcattacagg | aaaatgagaa | gctgcataaa | gaaatagaac | tcaaagatga | agaaattgca | 420 |
| cgtttgaaac | aagaaaatga | cgaattaatg | gaacttgctg | gcatgtaca | atacatggct | 480 |
| aatatgattg | aaaggctcac | tggaaatgct | ccacgaagtc | ttgaagactt | aaaggatttg | 540 |
| gatttggaag | aagcaagatt | tgaagatgaa | gcagacatgg | cagaagcaag | gattgaagat | 600 |
| gaaactgaca | tggctcggcc | ctctaattca | gatcagaata | tggatgcaca | tactgtctag | 660 |

<210> SEQ ID NO 3
<211> LENGTH: 621
<212> TYPE: DNA
<213> ORGANISM: mouse

<400> SEQUENCE: 3

| | | | | | |
|---|---|---|---|---|---|
| atgaatctca | gtatgaagca | gaagcaggag | ggagcccaag | agaatgtgaa | gaatagtcct | 60 |
| gtcccaagga | gaacgctgaa | gatgatccag | ccttctgcag | atggatctct | tgttggcaga | 120 |
| gaaaatgagt | tgccaaaagg | cttgttcaaa | aggaagcttt | gggatgacca | gctagcatct | 180 |
| cagacttcaa | gctgtggtcc | agaagctaat | gaaaataagg | atgttggaga | cctcacccag | 240 |

```
gaagcctttg atcttataag taaagagaac ccatcttctc agtattggaa agaagtggca    300
gagcagcgga ggaaagctct ctacgaagcg ctgaaagaga atgagaaact tcataaagaa    360
attgaacaaa aggacagtga gattgcccgc ctgagaaagg agaataaaga cttggcagaa    420
gtagctgagc acgtgcagta catggcggag gtaatcgaga ggctgagtaa tgaacctctg    480
gataactttg aatcaccgga tagtcaggaa tttgattctg aagaagaagc tgttgagtat    540
tcagaactgg aagactcagg agctgggacg tgtgctgaag actgtgtc ttcctccacg     600 gatgctaggc cgtgtacatg a                                              621

<210> SEQ ID NO 4
<211> LENGTH: 630
<212> TYPE: DNA
<213> ORGANISM: human

<400> SEQUENCE: 4
atgaatccca gtatgaagca gaaacaagaa gaaatcaaag agaatataaa gaatagttct    60
gtcccaagaa gaactctgaa gatgattcag ccttctgcat ctggatctct tgttggaaga    120
gaaaatgagc tgtccgcagg cttgtccaaa aggaaacatc ggaatgacca cttaacatct    180
acaacttcca gccctggggt tattgtccca gaatctagtg aaaataaaaa tcttggagga    240
gtcacccagg agtcatttga tcttatgatt aaagaaaatc catcctctca gtattggaag    300
gaagtggcag aaaaacggag aaaggcgctg tatgaagcac ttaaggaaaa tgagaaactt    360
cataaagaaa ttgaacaaaa ggacaatgaa attgcccgcc tgaaaaggga gaataaagaa    420
ctggcagaag tagcagaaca tgtacagtat atggcagagc taatagagag actgaatggt    480
gaacctctgg ataattttga atcactggat aatcaggaat tgattctga agaagaaact    540 gttgaggatt ctctagtgga agactcagaa attggcacgt gtgctgaagg aactgtatct    600
tcctctacgg atgcaaagcc atgtatatga                                    630

<210> SEQ ID NO 5
<211> LENGTH: 216
<212> TYPE: PRT
<213> ORGANISM: xenopus

<400> SEQUENCE: 5

Met Asn Ser Asn Met Lys Gln Arg Ser Asp Val Glu Asn Pro Ser Met
1               5                   10                  15

Ser Ile Lys Asn Tyr Ile Val Asp Lys Thr Asn Glu Ala Leu Ala Pro
            20                  25                  30

Arg Arg Thr Leu Lys Val Ile Gln Gln Ser Ala Ser Gly Cys Leu Val
        35                  40                  45

Gly Arg Thr Lys Glu Pro Ala Lys Asn Ser Thr Lys Arg Lys Leu Trp
    50                  55                  60

Asn Asp Gln Leu Thr Ser Lys Lys Ala Lys Val Glu Val Ala Val Asp
65                  70                  75                  80

Pro Glu His Gln Glu Asn Lys Asp Cys Pro Ser Glu Ala Tyr Asp Leu
                85                  90                  95

Met Val Lys Glu Thr Pro Thr Cys Leu Tyr Trp Lys Asp Val Ala Glu
            100                 105                 110

Glu Arg Arg Lys Ala Leu Tyr Glu Ala Leu Gln Glu Asn Glu Lys Leu
        115                 120                 125

His Gln Glu Ile Glu Leu Lys Asp Glu Glu Ile Ala Arg Leu Lys Gln
    130                 135                 140
```

Glu Asn Asp Glu Leu Met Glu Leu Ala Gly His Val Gln Tyr Met Ala
145                 150                 155                 160

Asn Met Ile Glu Arg Leu Thr Gly Asn Ala Pro Gln Ser Leu Glu Asp
                165                 170                 175

Leu Lys Asn Leu Asp Leu Glu Ala Arg Phe Glu Asp Glu Ala Glu
            180                 185                 190

Ser Arg Ile Glu Asp Glu Thr Asp Met Thr Gln Pro Ser Ser Ser Asp
            195                 200                 205

Gln Asn Met Asp Lys Gln Thr Val
        210                 215

<210> SEQ ID NO 6
<211> LENGTH: 219
<212> TYPE: PRT
<213> ORGANISM: xenopus

<400> SEQUENCE: 6

Met Asn Thr Asn Lys Lys Gln Arg Leu Asp Met Glu Lys Pro Thr Met
1               5                   10                  15

Ser Ile Lys Asn Tyr Phe Val Asp Lys Thr Asn Glu Ser Leu Ala Pro
            20                  25                  30

Arg Arg Thr Leu Lys Val Ile Gln Pro Ser Ala Ser Gly Cys Leu Val
            35                  40                  45

Gly Arg Thr Lys Glu Pro Val Lys Asn Ser Thr Lys Arg Lys Leu Trp
50                  55                  60

Asn Asp Gln Leu Thr Ser Lys Lys Ala Lys Val Glu Val Ala Val Asp
65                  70                  75                  80

Pro Glu His Arg Glu Asn Lys Asp Cys Ser Ser Glu Ala Tyr Asp Leu
                85                  90                  95

Met Val Lys Glu Thr Pro Thr Cys Leu Tyr Trp Lys Glu Val Ala Glu
            100                 105                 110

Glu Arg Arg Lys Ala Leu Tyr Glu Ala Leu Gln Glu Asn Glu Lys Leu
        115                 120                 125

His Lys Glu Ile Glu Leu Lys Asp Glu Glu Ile Ala Arg Leu Lys Gln
    130                 135                 140

Glu Asn Asp Glu Leu Met Glu Leu Ala Gly His Val Gln Tyr Met Ala
145                 150                 155                 160

Asn Met Ile Glu Arg Leu Thr Gly Asn Ala Pro Arg Ser Leu Glu Asp
                165                 170                 175

Leu Lys Asp Leu Asp Leu Glu Glu Ala Arg Phe Glu Asp Glu Ala Asp
            180                 185                 190

Met Ala Glu Ala Arg Ile Glu Asp Glu Thr Asp Met Ala Arg Pro Ser
        195                 200                 205

Asn Ser Asp Gln Asn Met Asp Ala His Thr Val
        210                 215

<210> SEQ ID NO 7
<211> LENGTH: 206
<212> TYPE: PRT
<213> ORGANISM: mouse

<400> SEQUENCE: 7

Met Asn Leu Ser Met Lys Gln Lys Gln Glu Gly Ala Gln Glu Asn Val
1               5                   10                  15

Lys Asn Ser Pro Val Pro Arg Arg Thr Leu Lys Met Ile Gln Pro Ser
            20                  25                  30

```
Ala Asp Gly Ser Leu Val Gly Arg Glu Asn Glu Leu Pro Lys Gly Leu
             35                  40                  45

Phe Lys Arg Lys Leu Trp Asp Asp Gln Leu Ala Ser Gln Thr Ser Ser
 50                  55                  60

Cys Gly Pro Glu Ala Asn Glu Asn Lys Asp Val Gly Asp Leu Thr Gln
 65                  70                  75                  80

Glu Ala Phe Asp Leu Ile Ser Lys Glu Asn Pro Ser Ser Gln Tyr Trp
                 85                  90                  95

Lys Glu Val Ala Glu Gln Arg Arg Lys Ala Leu Tyr Glu Ala Leu Lys
            100                 105                 110

Glu Asn Glu Lys Leu His Lys Glu Ile Glu Gln Lys Asp Ser Glu Ile
            115                 120                 125

Ala Arg Leu Arg Lys Glu Asn Lys Asp Leu Ala Glu Val Ala Glu His
        130                 135                 140

Val Gln Tyr Met Ala Glu Val Ile Glu Arg Leu Ser Asn Glu Pro Leu
145                 150                 155                 160

Asp Asn Phe Glu Ser Pro Asp Ser Gln Glu Phe Asp Ser Glu Glu Glu
                165                 170                 175

Ala Val Glu Tyr Ser Glu Leu Glu Asp Ser Gly Ala Gly Thr Cys Ala
            180                 185                 190

Glu Glu Thr Val Ser Ser Ser Thr Asp Ala Arg Pro Cys Thr
            195                 200                 205

<210> SEQ ID NO 8
<211> LENGTH: 209
<212> TYPE: PRT
<213> ORGANISM: human

<400> SEQUENCE: 8

Met Asn Pro Ser Met Lys Gln Lys Gln Glu Glu Ile Lys Glu Asn Ile
 1               5                  10                  15

Lys Asn Ser Ser Val Pro Arg Arg Thr Leu Lys Met Ile Gln Pro Ser
             20                  25                  30

Ala Ser Gly Ser Leu Val Gly Arg Glu Asn Glu Leu Ser Ala Gly Leu
             35                  40                  45

Ser Lys Arg Lys His Arg Asn Asp His Leu Thr Ser Thr Thr Ser Ser
 50                  55                  60

Pro Gly Val Ile Val Pro Glu Ser Ser Glu Asn Lys Asn Leu Gly Gly
 65                  70                  75                  80

Val Thr Gln Glu Ser Phe Asp Leu Met Ile Lys Glu Asn Pro Ser Ser
                 85                  90                  95

Gln Tyr Trp Lys Glu Val Ala Glu Lys Arg Arg Lys Ala Leu Tyr Glu
            100                 105                 110

Ala Leu Lys Glu Asn Glu Lys Leu His Lys Glu Ile Glu Gln Lys Asp
            115                 120                 125

Asn Glu Ile Ala Arg Leu Lys Lys Glu Asn Lys Glu Leu Ala Glu Val
        130                 135                 140

Ala Glu His Val Gln Tyr Met Ala Glu Leu Ile Glu Arg Leu Asn Gly
145                 150                 155                 160

Glu Pro Leu Asp Asn Phe Glu Ser Leu Asp Asn Gln Glu Phe Asp Ser
                165                 170                 175

Glu Glu Glu Thr Val Glu Asp Ser Leu Val Glu Asp Ser Glu Ile Gly
            180                 185                 190

Thr Cys Ala Glu Gly Thr Val Ser Ser Ser Thr Asp Ala Lys Pro Cys
```

195             200             205

Ile

<210> SEQ ID NO 9
<211> LENGTH: 105
<212> TYPE: DNA
<213> ORGANISM: xenopus

<400> SEQUENCE: 9
ctctatgaag cattacaaga aaatgagaag ctgcatcaag aaatagaact caaagatgaa      60
gaaattgcac gcttgaaaca agaaaatgat gaattaatgg aactt                    105

<210> SEQ ID NO 10
<211> LENGTH: 105
<212> TYPE: DNA
<213> ORGANISM: xenopus

<400> SEQUENCE: 10
ctctatgaag cattacagga aaatgagaag ctgcataaag aaatagaact caaagatgaa      60
gaaattgcac gtttgaaaca agaaaatgac gaattaatgg aactt                    105

<210> SEQ ID NO 11
<211> LENGTH: 105
<212> TYPE: DNA
<213> ORGANISM: mouse

<400> SEQUENCE: 11
ctctacgaag cgctgaaaga gaatgagaaa cttcataaag aaattgaaca aaaggacagt      60
gagattgccc gcctgagaaa ggagaataaa gacttggcag aagta                    105

<210> SEQ ID NO 12
<211> LENGTH: 105
<212> TYPE: DNA
<213> ORGANISM: human

<400> SEQUENCE: 12
ctgtatgaag cacttaagga aaatgagaaa cttcataaag aaattgaaca aaaggacaat      60
gaaattgccc gcctgaaaaa ggagaataaa gaactggcag aagta                    105

<210> SEQ ID NO 13
<211> LENGTH: 35
<212> TYPE: PRT
<213> ORGANISM: xenopus

<400> SEQUENCE: 13

Leu Tyr Glu Ala Leu Gln Glu Asn Glu Lys Leu His Gln Glu Ile Glu
 1               5                  10                  15

Leu Lys Asp Glu Glu Ile Ala Arg Leu Lys Gln Glu Asn Asp Glu Leu
            20                  25                  30

Met Glu Leu
        35

<210> SEQ ID NO 14
<211> LENGTH: 35
<212> TYPE: PRT
<213> ORGANISM: xenpus

<400> SEQUENCE: 14

Leu Tyr Glu Ala Leu Gln Glu Asn Glu Lys Leu His Lys Glu Ile Glu
 1               5                  10                  15

Leu Lys Asp Glu Glu Ile Ala Arg Leu Lys Gln Glu Asn Asp Glu Leu
             20                  25                  30

Met Glu Leu
        35

<210> SEQ ID NO 15
<211> LENGTH: 35
<212> TYPE: PRT
<213> ORGANISM: mouse

<400> SEQUENCE: 15

Leu Tyr Glu Ala Leu Lys Glu Asn Gly Lys Leu His Lys Glu Ile Glu
 1               5                  10                  15

Gln Lys Asp Ser Glu Ile Ala Arg Leu Arg Lys Glu Asn Lys Asp Leu
             20                  25                  30

Ala Glu Val
        35

<210> SEQ ID NO 16
<211> LENGTH: 35
<212> TYPE: PRT
<213> ORGANISM: human

<400> SEQUENCE: 16

Leu Tyr Glu Ala Leu Lys Glu Asn Gly Lys Leu His Lys Glu Ile Glu
 1               5                  10                  15

Gln Lys Asp Asn Glu Ile Ala Arg Leu Lys Lys Glu Asn Lys Glu Leu
             20                  25                  30

Ala Glu Val
        35

<210> SEQ ID NO 17
<211> LENGTH: 1047
<212> TYPE: DNA
<213> ORGANISM: xenopus

<400> SEQUENCE: 17
ggcacgagcc tgcagtggtc ttgtgcgtga aaagagcaga ggcttaagat gaatagcaac      60
atgaagcaga gatctgatgt agagaaccct tccatgtcaa ttaagaacta cattgtagat     120
aaaacaaatg aggcacttgc accaagaaga acacttaaag taatccagca atctgcatct     180
gggtgccttg ttggaaggac caaagagcct gctaaaaatt ctacaaaaag aaaactatgg     240
aatgatcaac tgacttcaaa aaggctaaa gttgaagtgg ctgttgatcc agaacaccag     300
gaaaacaagg attgcccatc tgaagcatat gacctcatgg tgaaagaaac cccaacttgt     360
ctgtactgga aggatgttgc agaggaaaga agaaaggccc tctatgaagc attacaagaa     420
aatgagaagc tgcatcaaga aatagaactc aaagatgaag aaattgcacg cttgaaacaa     480
gaaaatgatg aattaatgga acttgctgga catgtacagt acatggcgaa tatgattgaa     540
aggctcactg gaaatgcacc acaaagtctt gaagatttaa agaatttgga tttagaagaa     600
gcaaggtttg aagatgaagc agaatcaagg attgaagatg aaactgatat gactcagccc     660
tcaagttcag atcagaacat ggataaacaa actgtctagc ctgtgaacta ctgacttttt     720
taaaaaaaaa ttttttaaag tggccggtaa catttcgaaa gatcttctgc tcaatggaag     780
ctgaaaaagt aacattttat tagtccgtaa tgttgaaggg tttaagttca gtaagacctt     840
taactgcgaa gcttgacatc tgattaagga agttttagaa tttgctaact caatatttta     900

-continued

| | |
|---|---|
| agttgggtca cttgtctaac aaatactatg tatttattgt aaatgggtt cttttttaa | 960 |
| tttccagcct ttatgtgagg tgattgtaca tacttgaata aacttcagtt ttaagtatta | 1020 |
| aaaaaaacaa aaaaaaaaaa aaaaaaa | 1047 |

<210> SEQ ID NO 18
<211> LENGTH: 1064
<212> TYPE: DNA
<213> ORGANISM: xenopus

<400> SEQUENCE: 18

| | |
|---|---|
| ggctcgaggg aaggttttgt gtttgagagg agcggcaggc accaggttta atatgaatac | 60 |
| caacaagaag cagagattgg atatggagaa gcctaccatg tctattaaga actactttgt | 120 |
| ggataaaaca aacgagtccc ttgcacccag aagaacactt aaagtaatcc agccatctgc | 180 |
| atctggatgc cttgttggaa ggaccaaaga gcctgttaaa aattctacaa aaagaaagct | 240 |
| gtggaatgat cagctgactt caaaaaaggc taaagttgaa gtggctgttg atccagaaca | 300 |
| cagggaaaac aaagattgct catctgaagc ttatgacctt atggtgaaag aaacaccaac | 360 |
| ttgcctttac tggaaggagg ttgcagagga acgaagaaag gccctctatg aagcattaca | 420 |
| ggaaaatgag aagctgcata agaaatagaa ctcaaagat gaagaaattg cacgtttgaa | 480 |
| acaagaaaat gacgaattaa tggaacttgc tgggcatgta caatacatgg ctaatatgat | 540 |
| tgaaaggctc actggaaatg ctccacgaag tcttgaagac ttaaaggatt tggatttgga | 600 |
| agaagcaaga tttgaagatg aagcagacat ggcagaagca aggattgaag atgaaactga | 660 |
| catggctcgg ccctctaatt cagatcagaa tatggatgca catactgtct aggctgtgaa | 720 |
| ttgaccacat gagacttaaa gtggcctgaa acatatttaa agatgtcatg gtcagtggag | 780 |
| ggtggaaaca tgccattttg taattgtcca atgttttggg aagggtttaa tttcggtgaa | 840 |
| actgaccttaa aactacagaa cttgccatct gaaagttttt atctgctaaa tatttaagtt | 900 |
| ggtcacttga cagacaaata ctatgtattt ctttattgta aataggtttt tttaatgttc | 960 |
| cagccttttat gtgaggtgat tgtacatact tgaataaact tcagttttga acgtgttcta | 1020 |
| aacaaaaaaa aaaaaaaaa aaaaaaaaa aaaaaaaaa aaaa | 1064 |

<210> SEQ ID NO 19
<211> LENGTH: 1121
<212> TYPE: DNA
<213> ORGANISM: mouse

<400> SEQUENCE: 19

| | |
|---|---|
| cattgtgcgg ctctcacgct cgccgggaac tgagcattgc tgtctgtgag tccgagggcg | 60 |
| cgggagaccg agggcggggc gagtgcaact ccggccgcgg gatcgcgggc tggcccgaat | 120 |
| gcccggcctg cttctcagcc acggggagcc ggcctgggag cgacgattt gaagggtctg | 180 |
| caggttcggg tcgttctggc gtcgttgaat ccggtgtggt gccagggcct tgtgcggctc | 240 |
| tcacgctcgc cgggaactga gcattgctgt ctctgaaaaa tgaatctcag tatgaagcag | 300 |
| aagcaggagg gagcccaaga gaatgtgaag aatagtcctg tcccaaggag aacgctgaag | 360 |
| atgatccagc cttctgcaga tggatctctt gttggcagaa aaatgagtt gccaaaaggc | 420 |
| ttgttcaaaa ggaagctttg ggatgaccag ctagcatctc agacttcaag ctgtggtcca | 480 |
| gaagctaatg aaaataagga tgttggagac ctcacccagg aagcctttga tcttataagt | 540 |
| aaagagaacc catcttctca gtattggaaa gaagtggcag agcagcggag gaaagctctc | 600 |
| tacgaagcgc tgaaagagaa tgagaaactt cataaagaaa ttgaacaaaa ggacagtgag | 660 |

-continued

```
attgcccgcc tgagaaagga gaataaagac ttggcagaag tagctgagca cgtgcagtac      720
atggcggagg taatcgagag gctgagtaat gaacctctgg ataactttga atcaccggat      780
agtcaggaat ttgattctga agaagaagct gttgagtatt cagaactgga agactcagga      840
gctgggacgt gtgctgaaga gactgtgtct cctccacgg atgctaggcc gtgtacatga       900
ggtgtgggac gcactgccag cgttgccctt agtatagct cttggtaaac taactacacg       960
gtgcaagtgc tggaagccag gtttgaatcc tggggctatc actatgttaa atacagata     1020 gtgtgtattt ttaatccgtt ttatgtaaat agcattttca tttttgtcag tgtcagatat    1080
aaactgtata ttaaataaac ttcaatttcc tgttgaacat t                        1121
```

<210> SEQ ID NO 20
<211> LENGTH: 961
<212> TYPE: DNA
<213> ORGANISM: human

<400> SEQUENCE: 20

```
tcttctgtgc ttcaccatct acataatgaa tcccagtatg aagcagaaac aagaagaaat       60
caaagagaat ataaagaata gttctgtccc aagaagaact ctgaagatga ttcagccttc      120
tgcatctgga tctcttgttg aagagaaaa tgagctgtcc gcaggcttgt ccaaaaggaa      180
acatcggaat gaccacttaa catctacaac ttccagccct ggggttattg tcccagaatc      240
tagtgaaaat aaaaatcttg gaggagtcac ccaggagtca tttgatctta tgattaaaga      300
aaatccatcc tctcagtatt ggaaggaagt ggcagaaaaa cggagaaagg cgctgtatga      360
agcacttaag gaaaatgaga aacttcataa agaaattgaa caaaaggaca atgaaattgc      420
ccgcctgaaa aaggagaata agaactggc agaagtagca gaacatgtac agtatatggc      480
agagctaata gagagactga atggtgaacc tctggataat tttgaatcac tggataatca      540
ggaatttgat tctgaagaag aaactgttga ggattctcta gtggaagact cagaaattgg      600
cacgtgtgct gaaggaactg tatcttcctc tacggatgca aagccatgta tatgaaatgc      660
attaatattt gactgttgag aatttttactg ccgaagttta cctccactag ttctttgtag    720
cagagtacat aactacataa tgccaactct ggaatcaaat ttccttgttt gaatcctggg     780
accctattgc attaaagtac aaatactatg tatttttaat ctatgatggt ttatgtgaat    840
aggattttct cagttgtcag ccatgactta tgtttattac taaataaact tcaaactcct    900
gttgaacatt gtgtataact tagaataatg aaatataagg agtatgtgta gaaaaaaaaa    960
a                                                                         961
```

<210> SEQ ID NO 21
<211> LENGTH: 216
<212> TYPE: PRT
<213> ORGANISM: xenopus

<400> SEQUENCE: 21

```
Met Asn Ser Asn Met Lys Gln Arg Ser Asp Val Glu Asn Pro Ser Met
 1               5                   10                  15

Ser Ile Lys Asn Tyr Ile Val Asp Lys Thr Asn Glu Ala Leu Ala Pro
            20                  25                  30

Arg Arg Thr Leu Lys Val Ile Gln Gln Ser Ala Ser Gly Cys Leu Val
        35                  40                  45

Gly Arg Thr Lys Glu Pro Ala Lys Asn Ser Thr Lys Arg Lys Leu Trp
    50                  55                  60
```

Asn Asp Gln Leu Thr Ser Lys Lys Ala Lys Val Glu Ala Val Asp
65                  70                  75                  80

Pro Glu His Gln Glu Asn Lys Asp Cys Pro Ser Glu Ala Tyr Asp Leu
            85                  90                  95

Met Val Lys Glu Thr Pro Thr Cys Leu Tyr Trp Lys Asp Val Ala Glu
                100                 105                 110

Glu Arg Lys Ala Leu Tyr Glu Ala Leu Gln Glu Asn Glu Lys Leu
        115                 120                 125

His Gln Glu Ile Glu Leu Lys Asp Glu Ile Ala Arg Leu Lys Gln
    130                 135                 140

Glu Asn Asp Glu Leu Met Glu Leu Ala Gly His Val Gln Tyr Met Ala
145                 150                 155                 160

Asn Met Ile Glu Arg Leu Thr Gly Asn Ala Pro Gln Ser Leu Glu Asp
                165                 170                 175

Leu Lys Asn Leu Asp Leu Glu Glu Ala Arg Phe Glu Asp Glu Ala Glu
                180                 185                 190

Ser Arg Ile Glu Asp Glu Thr Asp Met Thr Gln Pro Ser Ser Ser Asp
            195                 200                 205

Gln Asn Met Asp Lys Gln Thr Val
    210                 215

<210> SEQ ID NO 22
<211> LENGTH: 219
<212> TYPE: PRT
<213> ORGANISM: xenopus

<400> SEQUENCE: 22

Met Asn Thr Asn Lys Lys Gln Arg Leu Asp Met Glu Lys Pro Thr Met
1               5                   10                  15

Ser Ile Lys Asn Tyr Phe Val Asp Lys Thr Asn Glu Ser Leu Ala Pro
                20                  25                  30

Arg Arg Thr Leu Lys Val Ile Gln Pro Ser Ala Ser Gly Cys Leu Val
            35                  40                  45

Gly Arg Thr Lys Glu Pro Val Lys Asn Ser Thr Lys Arg Lys Leu Trp
    50                  55                  60

Asn Asp Gln Leu Thr Ser Lys Lys Ala Lys Val Glu Ala Val Asp
65                  70                  75                  80

Pro Glu His Arg Glu Asn Lys Asp Cys Ser Ser Glu Ala Tyr Asp Leu
            85                  90                  95

Met Val Lys Glu Thr Pro Thr Cys Leu Tyr Trp Lys Glu Val Ala Glu
                100                 105                 110

Glu Arg Arg Lys Ala Leu Tyr Glu Ala Leu Gln Glu Asn Glu Lys Leu
        115                 120                 125

His Lys Glu Ile Glu Leu Lys Asp Glu Glu Ile Ala Arg Leu Lys Gln
    130                 135                 140

Glu Asn Asp Glu Leu Met Glu Leu Ala Gly His Val Gln Tyr Met Ala
145                 150                 155                 160

Asn Met Ile Glu Arg Leu Thr Gly Asn Ala Pro Arg Ser Leu Glu Asp
                165                 170                 175

Leu Lys Asp Leu Asp Leu Glu Glu Ala Arg Phe Glu Asp Glu Ala Asp
                180                 185                 190

Met Ala Glu Ala Arg Ile Glu Asp Glu Thr Asp Met Ala Arg Pro Ser
            195                 200                 205

Asn Ser Asp Gln Asn Met Asp Ala His Thr Val
    210                 215

```
<210> SEQ ID NO 23
<211> LENGTH: 206
<212> TYPE: PRT
<213> ORGANISM: mouse

<400> SEQUENCE: 23

Met Asn Leu Ser Met Lys Gln Lys Gln Glu Gly Ala Gln Glu Asn Val
 1               5                  10                  15

Lys Asn Ser Pro Val Pro Arg Arg Thr Leu Lys Met Ile Gln Pro Ser
            20                  25                  30

Ala Asp Gly Ser Leu Val Gly Arg Glu Asn Glu Leu Pro Lys Gly Leu
        35                  40                  45

Phe Lys Arg Lys Leu Trp Asp Asp Gln Leu Ala Ser Gln Thr Ser Ser
 50                  55                  60

Cys Gly Pro Glu Ala Asn Glu Asn Lys Asp Val Gly Asp Leu Thr Gln
 65                  70                  75                  80

Glu Ala Phe Asp Leu Ile Ser Lys Glu Asn Pro Ser Ser Gln Tyr Trp
                85                  90                  95

Lys Glu Val Ala Glu Gln Arg Arg Lys Ala Leu Tyr Glu Ala Leu Lys
            100                 105                 110

Glu Asn Glu Lys Leu His Lys Glu Ile Glu Gln Lys Asp Ser Glu Ile
        115                 120                 125

Ala Arg Leu Arg Lys Glu Asn Lys Asp Leu Ala Glu Val Ala Glu His
    130                 135                 140

Val Gln Tyr Met Ala Glu Val Ile Glu Arg Leu Ser Asn Glu Pro Leu
145                 150                 155                 160

Asp Asn Phe Glu Ser Pro Asp Ser Gln Glu Phe Asp Ser Glu Glu Glu
                165                 170                 175

Ala Val Glu Tyr Ser Glu Leu Gly Asp Ser Gly Ala Gly Thr Cys Ala
            180                 185                 190

Glu Glu Thr Val Ser Ser Ser Thr Asp Ala Arg Pro Cys Thr
        195                 200                 205

<210> SEQ ID NO 24
<211> LENGTH: 209
<212> TYPE: PRT
<213> ORGANISM: human

<400> SEQUENCE: 24

Met Asn Pro Ser Met Lys Gln Lys Gln Glu Glu Ile Lys Glu Asn Ile
 1               5                  10                  15

Lys Asn Ser Ser Val Pro Arg Arg Thr Leu Lys Met Ile Gln Pro Ser
            20                  25                  30

Ala Ser Gly Ser Leu Val Gly Arg Glu Asn Glu Leu Ser Ala Gly Leu
        35                  40                  45

Ser Lys Arg Lys His Arg Asn Asp His Leu Thr Ser Thr Thr Ser Ser
 50                  55                  60

Pro Gly Val Ile Val Pro Glu Ser Ser Glu Asn Lys Asn Leu Gly Gly
 65                  70                  75                  80

Val Thr Gln Glu Ser Phe Asp Leu Met Ile Lys Glu Asn Pro Ser Ser
                85                  90                  95

Gln Tyr Trp Lys Glu Val Ala Glu Lys Arg Arg Lys Ala Leu Tyr Glu
            100                 105                 110

Ala Leu Lys Glu Asn Glu Lys Leu His Lys Glu Ile Glu Gln Lys Asp
        115                 120                 125
```

```
Asn Glu Ile Ala Arg Leu Lys Lys Glu Asn Lys Glu Leu Ala Glu Val
        130                 135                 140
Ala Glu His Val Gln Tyr Met Ala Glu Leu Ile Glu Arg Leu Asn Gly
145                 150                 155                 160
Glu Pro Leu Asp Asn Phe Glu Ser Leu Asp Asn Gln Glu Phe Asp Ser
                165                 170                 175
Glu Glu Glu Thr Val Glu Asp Ser Leu Val Glu Asp Ser Glu Ile Gly
            180                 185                 190
Thr Cys Ala Glu Gly Thr Val Ser Ser Ser Thr Asp Ala Lys Pro Cys
        195                 200                 205
Ile
```

<210> SEQ ID NO 25
<211> LENGTH: 159
<212> TYPE: DNA
<213> ORGANISM: xenopus

<400> SEQUENCE: 25

```
gtaatccagc aatctgcatc tgggtgcctt gttggaagga ccaaagagcc tgctaaaaat    60
tctacaaaaa gaaaactatg gaatgatcaa ctgacttcaa aaaaggctaa agttgaagtg   120
gctgttgatc cagaacacca ggaaaacaag gattgccca                          159
```

<210> SEQ ID NO 26
<211> LENGTH: 159
<212> TYPE: DNA
<213> ORGANISM: xenopus

<400> SEQUENCE: 26

```
gtaatccagc catctgcatc tggatgcctt gttggaagga ccaaagagcc tgttaaaaat    60
tctacaaaaa gaaagctgtg gaatgatcag ctgacttcaa aaaaggctaa agttgaagtg   120
gctgttgatc cagaacacag ggaaaacaaa gattgctca                          159
```

<210> SEQ ID NO 27
<211> LENGTH: 147
<212> TYPE: DNA
<213> ORGANISM: mouse

<400> SEQUENCE: 27

```
atgatccagc cttctgcaga tggatctctt gttggcagag aaaatgagtt gccaaaaggc    60
ttgttcaaaa ggaagctttg ggatgaccag ctagcatctc agacttcaag ctgtggtcca   120
gaagctaatg aaaataagga tgttgga                                       147
```

<210> SEQ ID NO 28
<211> LENGTH: 156
<212> TYPE: DNA
<213> ORGANISM: human

<400> SEQUENCE: 28

```
atgattcagc cttctgcatc tggatctctt gttggaagag aaaatgagct gtccgcaggc    60
ttgtccaaaa ggaaacatcg gaatgaccac ttaacatcta caacttccag ccctgggtt   120
attgtcccag aatctagtga aaataaaaat cttgga                             156
```

<210> SEQ ID NO 29
<211> LENGTH: 53
<212> TYPE: PRT
<213> ORGANISM: xenopus

```
<400> SEQUENCE: 29

Val Ile Gln Gln Ser Ala Ser Gly Cys Leu Val Gly Arg Thr Lys Glu
 1               5                  10                  15
Pro Ala Lys Asn Ser Thr Lys Arg Lys Leu Trp Asn Asp Gln Leu Thr
             20                  25                  30
Ser Lys Lys Ala Lys Val Glu Val Ala Val Asp Pro Glu His Gln Glu
         35                  40                  45
Asn Lys Asp Cys Pro
     50

<210> SEQ ID NO 30
<211> LENGTH: 53
<212> TYPE: PRT
<213> ORGANISM: xenopus

<400> SEQUENCE: 30

Val Ile Gln Pro Ser Ala Ser Gly Cys Leu Val Gly Arg Thr Lys Glu
 1               5                  10                  15
Pro Val Lys Asn Ser Thr Lys Arg Lys Leu Trp Asn Asp Gln Leu Thr
             20                  25                  30
Ser Lys Lys Ala Lys Val Glu Val Ala Val Asp Pro Glu His Arg Glu
         35                  40                  45
Asn Lys Asp Cys Ser
     50

<210> SEQ ID NO 31
<211> LENGTH: 49
<212> TYPE: PRT
<213> ORGANISM: mouse

<400> SEQUENCE: 31

Met Ile Gln Pro Ser Ala Asp Gly Ser Leu Val Gly Arg Glu Asn Glu
 1               5                  10                  15
Leu Pro Lys Gly Leu Phe Lys Arg Lys Leu Trp Asp Asp Gln Leu Ala
             20                  25                  30
Ser Gln Thr Ser Ser Cys Gly Pro Glu Ala Asn Glu Asn Lys Asp Val
         35                  40                  45
Gly

<210> SEQ ID NO 32
<211> LENGTH: 52
<212> TYPE: PRT
<213> ORGANISM: human

<400> SEQUENCE: 32

Met Ile Gln Pro Ser Ala Ser Gly Ser Leu Val Gly Arg Glu Asn Glu
 1               5                  10                  15
Leu Ser Ala Gly Leu Ser Lys Arg Lys His Arg Asn Asp His Leu Thr
             20                  25                  30
Ser Thr Thr Ser Ser Pro Gly Val Ile Val Pro Glu Ser Ser Glu Asn
         35                  40                  45
Lys Asn Leu Gly
     50

<210> SEQ ID NO 33
<211> LENGTH: 9
<212> TYPE: PRT
<213> ORGANISM: human
```

<400> SEQUENCE: 33

Arg Arg Thr Leu Lys Val Ile Gln Pro
 1               5

<210> SEQ ID NO 34
<211> LENGTH: 20
<212> TYPE: PRT
<213> ORGANISM: Artificial Sequence
<220> FEATURE:
<223> OTHER INFORMATION: histidine tag

<400> SEQUENCE: 34

Met Gly Ser Ser His His His His His His Ser Ser Gly Leu Val Pro
 1               5                  10                  15

Arg Gly Ser His
            20

<210> SEQ ID NO 35
<211> LENGTH: 9
<212> TYPE: PRT
<213> ORGANISM: Artificial Sequence
<220> FEATURE:
<223> OTHER INFORMATION: mitotic cyclins
<221> NAME/KEY: VARIANT
<222> LOCATION: 2, 8
<223> OTHER INFORMATION: Xaa = Any Amino Acid

<400> SEQUENCE: 35

Arg Xaa Ala Leu Gly Val Ile Xaa Asn
 1               5

<210> SEQ ID NO 36
<211> LENGTH: 20
<212> TYPE: DNA
<213> ORGANISM: Artificial Sequence
<220> FEATURE:
<223> OTHER INFORMATION: primers

<400> SEQUENCE: 36
agcaacatga agcagagatc                                        20

<210> SEQ ID NO 37
<211> LENGTH: 20
<212> TYPE: DNA
<213> ORGANISM: Artificial Sequence
<220> FEATURE:
<223> OTHER INFORMATION: primers

<400> SEQUENCE: 37
aatcagatgt caagcttcgc                                        20

<210> SEQ ID NO 38
<211> LENGTH: 19
<212> TYPE: DNA
<213> ORGANISM: Artificial Sequence
<220> FEATURE:
<223> OTHER INFORMATION: primers

<400> SEQUENCE: 38
caacaagaag cagagattg                                         19

<210> SEQ ID NO 39
<211> LENGTH: 18
<212> TYPE: DNA
<213> ORGANISM: Artificial Sequence

```
<220> FEATURE:
<223> OTHER INFORMATION: primers

<400> SEQUENCE: 39
agcctagaca gtatgtgc                                                    18

<210> SEQ ID NO 40
<211> LENGTH: 20
<212> TYPE: DNA
<213> ORGANISM: Artificial Sequence
<220> FEATURE:
<223> OTHER INFORMATION: primers

<400> SEQUENCE: 40
attggattgt ggcacctcct                                                  20

<210> SEQ ID NO 41
<211> LENGTH: 20
<212> TYPE: DNA
<213> ORGANISM: Artificial Sequence
<220> FEATURE:
<223> OTHER INFORMATION: primers

<400> SEQUENCE: 41
ttggatctca gactcaacgg                                                  20

<210> SEQ ID NO 42
<211> LENGTH: 20
<212> TYPE: DNA
<213> ORGANISM: Artificial Sequence
<220> FEATURE:
<223> OTHER INFORMATION: primers

<400> SEQUENCE: 42
tacatctggg ctcttagcga                                                  20

<210> SEQ ID NO 43
<211> LENGTH: 19
<212> TYPE: DNA
<213> ORGANISM: Artificial Sequence
<220> FEATURE:
<223> OTHER INFORMATION: primers

<400> SEQUENCE: 43
caaatgaaag cgctgctgg                                                   19

<210> SEQ ID NO 44
<211> LENGTH: 20
<212> TYPE: DNA
<213> ORGANISM: Artificial Sequence
<220> FEATURE:
<223> OTHER INFORMATION: primers

<400> SEQUENCE: 44
gctggacatg taccagtaca                                                  20

<210> SEQ ID NO 45
<211> LENGTH: 20
<212> TYPE: DNA
<213> ORGANISM: Artificial Sequence
<220> FEATURE:
<223> OTHER INFORMATION: primers

<400> SEQUENCE: 45
tcacctcaca taaaggctgg                                                  20
```

```
<210> SEQ ID NO 46
<211> LENGTH: 22
<212> TYPE: DNA
<213> ORGANISM: Artificial Sequence
<220> FEATURE:
<223> OTHER INFORMATION: primers

<400> SEQUENCE: 46
ggatggattt gttgcaccag tc                                             22

<210> SEQ ID NO 47
<211> LENGTH: 21
<212> TYPE: DNA
<213> ORGANISM: Artificial Sequence
<220> FEATURE:
<223> OTHER INFORMATION: primers

<400> SEQUENCE: 47
cactctccga gctcacttct c                                              21

<210> SEQ ID NO 48
<211> LENGTH: 20
<212> TYPE: DNA
<213> ORGANISM: Artificial Sequence
<220> FEATURE:
<223> OTHER INFORMATION: primers

<400> SEQUENCE: 48
gtggccggta acatttcgaa                                                20
```